United States Patent
Burzio Eriz et al.

(10) Patent No.: US 10,457,943 B2
(45) Date of Patent: *Oct. 29, 2019

(54) ANTISENSE OLIGONUCLEOTIDES FOR TREATMENT OF CANCER STEM CELLS

(71) Applicant: Andes Biotechnologies Global, Inc., Burlingame, CA (US)

(72) Inventors: Luis O. Burzio Eriz, Santiago (CL); Veronica A. Burzio Menendez, Santiago (CL); Jaime E. Villegas Olavarria, Santiago (CL)

(73) Assignee: Andes Biotechnologies Global Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,535

(22) Filed: Nov. 29, 2017

(65) Prior Publication Data

US 2018/0171335 A1 Jun. 21, 2018

Related U.S. Application Data

(63) Continuation of application No. 14/775,654, filed as application No. PCT/US2014/029606 on Mar. 14, 2014, now Pat. No. 9,862,944.

(60) Provisional application No. 61/937,438, filed on Feb. 7, 2014, provisional application No. 61/790,072, filed on Mar. 15, 2013, provisional application No. 61/785,269, filed on Mar. 14, 2013.

(51) Int. Cl.
| | |
|---|---|
| *A61K 48/00* | (2006.01) |
| *C07H 21/04* | (2006.01) |
| *C12N 15/113* | (2010.01) |
| *A61K 31/7088* | (2006.01) |
| *A61K 45/06* | (2006.01) |
| *A61K 31/7105* | (2006.01) |
| *C12N 5/09* | (2010.01) |

(52) U.S. Cl.
CPC ........ *C12N 15/113* (2013.01); *A61K 31/7088* (2013.01); *A61K 31/7105* (2013.01); *A61K 45/06* (2013.01); *C12N 5/0693* (2013.01); *C12N 2310/113* (2013.01); *C12N 2320/30* (2013.01); *C12N 2320/31* (2013.01); *C12N 2501/65* (2013.01); *C12N 2501/999* (2013.01); *C12N 2510/00* (2013.01)

(58) Field of Classification Search
CPC .................... A61K 31/713; C12N 15/111
See application file for complete search history.

(56) References Cited

U.S. PATENT DOCUMENTS

| | | | |
|---|---|---|---|
| 3,687,808 A | 8/1972 | Merigan, Jr. et al. | |
| 5,093,246 A | 3/1992 | Cech et al. | |
| 5,194,599 A | 3/1993 | Froehler et al. | |
| 5,459,255 A | 10/1995 | Cook et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,527,899 A | 6/1996 | Froehler | |
| 5,539,082 A | 7/1996 | Nielsen et al. | |
| 5,541,306 A | 7/1996 | Agrawal et al. | |
| 5,550,111 A | 8/1996 | Suhadolnik et al. | |
| 5,552,540 A | 9/1996 | Haralambidis | |
| 5,563,253 A | 10/1996 | Agrawal et al. | |
| 5,565,555 A | 10/1996 | Froehler et al. | |
| 5,571,799 A | 11/1996 | Tkachuk et al. | |
| 5,587,361 A | 12/1996 | Cook et al. | |
| 5,587,469 A | 12/1996 | Cook et al. | |
| 5,594,121 A | 1/1997 | Froehler et al. | |
| 5,596,086 A | 1/1997 | Matteucci et al. | |
| 5,596,091 A | 1/1997 | Switzer | |
| 5,602,240 A | 2/1997 | Mesmaeker et al. | |
| 5,608,046 A | 3/1997 | Cook et al. | |
| 5,610,289 A | 3/1997 | Cook et al. | |
| 5,614,617 A | 3/1997 | Cook et al. | |
| 5,618,704 A | 4/1997 | Sanghvi et al. | |
| 5,623,070 A | 4/1997 | Cook et al. | |
| 5,625,050 A | 4/1997 | Beaton et al. | |
| 5,633,360 A | 5/1997 | Bischofberger et al. | |
| 5,645,985 A | 7/1997 | Froehler et al. | |
| 5,646,269 A | 7/1997 | Matteucci et al. | |
| 5,663,312 A | 9/1997 | Chaturvedula | |

(Continued)

FOREIGN PATENT DOCUMENTS

| | | |
|---|---|---|
| WO | WO-98/55495 A2 | 12/1998 |
| WO | WO-98/55495 A3 | 12/1998 |

(Continued)

OTHER PUBLICATIONS

Ahmed, N. et al. (Sep. 25, 2013). "Getting to know ovarian cancer ascites: opportunities for targeted therapy-based translational research," *Front Oncol.* 3(Article 256):1-12.

Chen, K. et al. (Jun. 2013, e-pub. May 20, 2013). "Understanding and targeting cancer stem cells: therapeutic implications and challenges," *Acta. Pharmacol. Sin.* 34(6):732-740.

Clarke, M. F. et al. (Oct. 1, 2006, e-pub. Sep. 21, 2006). "Cancer stem cells—perspectives on current status and future directions: AACR Workshop on cancer stem cells," *Cancer Res.* 66(19):9339-9344.

(Continued)

*Primary Examiner* — Amy H Bowman
(74) *Attorney, Agent, or Firm* — Mintz Levin Cohn Ferris Glovsky and Popeo P.C.

(57) ABSTRACT

The invention provides oligonucleotides complementary to a non-coding chimeric mitochondrial RNA as well as compositions and kits comprising the same, and their use in treating and preventing metastasis or relapse of a cancer in an individual previously treated for cancer with a therapy. The invention also provides oligonucleotides complementary to a non-coding chimeric mitochondrial RNA as well as compositions and kits comprising the same, and their use in treating a refractory cancer (e.g., a refractory HPV-associated cancer).

19 Claims, 15 Drawing Sheets

Specification includes a Sequence Listing.

(56) References Cited

U.S. PATENT DOCUMENTS

| | | | |
|---|---|---|---|
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,714,331 | A | 2/1998 | Buchardt et al. |
| 5,719,262 | A | 2/1998 | Buchardt et al. |
| 5,721,218 | A | 2/1998 | Froehler |
| 5,763,588 | A | 6/1998 | Matteucci et al. |
| 5,792,608 | A | 8/1998 | Swaminathan et al. |
| 5,830,653 | A | 11/1998 | Froehler et al. |
| 6,005,096 | A | 12/1999 | Matteucci et al. |
| 7,399,845 | B2 | 7/2008 | Seth et al. |
| 8,318,686 | B2 | 11/2012 | Burzio et al. |
| 8,614,095 | B2 | 12/2013 | Radovanovic et al. |
| 8,895,719 | B2 | 11/2014 | Burzio et al. |
| 9,862,944 | B2 | 1/2018 | Burzio Eriz et al. |
| 2004/0224389 | A1 | 11/2004 | Bellgrau et al. |
| 2006/0241033 | A1 | 10/2006 | Burzio et al. |
| 2010/0292099 | A1 | 11/2010 | Dreyfus et al. |
| 2012/0325090 | A1 | 12/2012 | Takahashi |
| 2015/0064700 | A1 | 3/2015 | Burzio et al. |
| 2016/0138109 | A1 | 5/2016 | Villota Arcos et al. |
| 2016/0304971 | A1 | 10/2016 | Burzio et al. |

FOREIGN PATENT DOCUMENTS

| | | |
|---|---|---|
| WO | WO-98/55495 C1 | 12/1998 |
| WO | WO-2005/001030 A2 | 1/2005 |
| WO | WO-2005/001030 A3 | 1/2005 |
| WO | WO-2007/46511 A1 | 4/2007 |
| WO | WO-2014/153206 A2 | 9/2014 |
| WO | WO-2014/153206 A3 | 9/2014 |

OTHER PUBLICATIONS

Chihara, N. et al. (2011). "Mitochondrial DNA alterations in colorectal cancer cell lines," *J Nippon Med Sch* 78(1):13-21.

De Sanjosé, S. et al. (Nov. 2013, e-pub. Jul. 22, 2013). "Worldwide human papillomavirus genotype attribution in over 2000 cases of intraepithelial and invasive lesions of the vulva," *Eur. J. Cancer* 49(16):3450-3461.

Ding, Z. et al. (Sep. 15, 2000). "Human papillomavirus type 16-immortalized endocervical cells selected for resistance to cisplatin are malignantly transformed and have a multidrug resistance phenotype," *Int. J. Cancer* 87(6):818-823.

Domingo-Domenech, J. et al. (Sep. 11, 2012). "Suppression of acquired docetaxel resistance in prostate cancer through depletion of notch- and hedgehog-dependent tumor-initiating cells," *Cancer Cell* 22(3):373-388.

Elbashir, S. M. et al. (May 24, 2001). "Duplexes of 21-nucleotide RNAs mediate RNA interference in cultured mammalian cells," *Nature* 411(6836):494-498.

Englisch, U. et al. (Jun. 1991). "Chemically Modified Oligonucleotides as Probes and Inhibitors," *Angewandte Chemie International Edition* 30(6):613-629.

Fan, X. et al. (May-Jun. 2012, e-published Sep. 16, 2010). "Effective enrichment of prostate cancer stem cells from spheres in a suspension culture system," *Urol Oncol* 30(3):314-318. (abstract only).

Feng, D. et al. (Nov. 2009). "Identification and characterization of cancer stem-like cells from primary carcinoma of the cervix uteri," *Oncol. Rep.* 22(5):1129-1134.

Harousseau, J.L. (Aug. 5, 2009). Maintenance therapy in multiple myeloma, *Hematol. Rep.* 1(2) (e12):65-69.

Haseloff, J. et al. (Oct. 15, 1989). "Sequences required for self-catalysed cleavage of the satellite RNA of tobacco ringspot virus," *Gene* 82(1):43-52.

International Search Report dated Aug. 21, 2014, for PCT Patent Application No. PCT/US2014/029606 filed on Mar. 14, 2014, four pages International Search Report dated Nov. 17, 2014, for PCT Application No. PCT/US2014/029602, filed on Mar. 14, 2014, 6 pages.

Kroschwitz, J. I. ed. (1990). "Polynucleotides" *Concise Encyclopedia of Polymer Science and Engineering*, John Wiley & Sons, Inc.: NY, pp. 858-859.

Kyle, R. A. et al. (Mar. 15, 2008). "Multiple myeloma," *Blood* 111(6):2962-2972.

Landerer, E. et al. (Aug. 2011, e-published Feb. 24, 2011). "Nuclear localization of the mitochondrial ncRNAs in normal and cancer cells," *Cell Oncol* 34(4):297-305.

Liao, J. et al. (Jan. 2014). "Ovarian cancer spheroid cells with stem cell-like properties contribute to tumor generation, metastasis and chemotherapy resistance through hypoxia-resistant metabolism," *PloS One* 9(1):e84941.

Liu, J. et al. (Feb. 2013, e-published Nov. 29, 2012). "Spheroid body-forming cells in the human gastric cancer cell line MKN-45 possess cancer stem cell properties," *Int J Oncol* 42(2):453-459.

Lu, P. Y. et al. (Jun. 2003). "siRNA-mediated antitumorigenesis for drug target validation and therapeutics," *Curr. Opin. Mol. Ther.* 5(3):225-234.

Mani S. A. et al. (May 16, 2008). "The epithelial-mesenchymal transition generates cells with properties of stem cells," *Cell* 133(4):704-715.

McManus, M. T. et al. (Oct. 2002). "Gene silencing in mammals by small interfering RNAs," *Nat. Rev. Genet.* 3(10):737-747.

Mukhopadhyay, P. et al. (Nov. 12, 2013). "Heterogeneity of functional properties of Clone 66 murine breast cancer cells expressing various stem cell phenotypes," *PloS One* 8(11) (e78725) pp. 1-15

Muñoz, N. et al. (Feb. 6, 2003). "Epidemiologic classification of human papillomavirus types associated with cervical cancer," *N. Engl. J. Med.* 348(6):518-527.

Nielsen, P. E. et al. (Dec. 6, 1991). "Sequence-selective recognition of DNA by strand displacement with a thymine-substituted polyamide," *Science* 254(5037):1497-1500.

Ohata, H. et al. (Oct. 1, 2012, e-pub. Sep. 20, 2012). "Induction of the stem-like cell regulator CD44 by Rho kinase inhibition contributes to the maintenance of colon cancer-initiating cells," *Cancer Res.* 72(19):5101-5110.

Perantoni, A. O. (1998). "Carcinogenesis" Chapter 3 in *The Biological Basis of Cancer*, McKinnell, R. G. et al. eds., Cambridge University Press: Cambridge, UK., p. 79-114.

Ponti, D. et al. (Jul. 1, 2005). "Isolation and in Vitro propagation of tumorigenic breast cancer cells with stem/progenitor cell properties," *Cancer Res.* 65(13):5506-5511.

Rossi, J. J. (May 1, 1994). "Practical ribozymes. Making ribozymes work in cells," *Curr. Biol.* 4(5):469-471.

Sanghvi, Y. S. (1993). "Heterocyclic Base Modifications in Nucleic Acids and Their Applications in Antisense Oligonucleotides" Chapter 15 in *Antisense Research and Applications*, Crooke, S. T. et al. eds., CRC Press, Inc.: Boca Raton, FL, pp. 273-288.

Singh, S. K. et al. (Sep. 15, 2003). "Identification of a cancer stem cell in human brain tumors," *Cancer Res.* 63(18):5821-5828.

Tjalma, W. A. et al. (Feb. 15, 2013, e-pub. Jul. 24, 2012). "Differences in human papillomavirus type distribution in high-grade cervical intraepithelial neoplasia and invasive cervical cancer in Europe," *Int. J. Cancer* 132(4):854-867.

Tjalma, W. A. et al. (Jan. 2012). "Don't forget HPV-45 in cervical cancer screening," *Am. J. Clin. Pathol.* 137(1):161-163.

Varas, M. et al. (Nov. 2011). "Abstract B181:A lentivirus-encoding shRNA targeting a noncoding mitochondrial RNA inhibits melanoma tumor growth and metastasis in a mouse model in vivo," Molecular Cancer Therapeutics 10:11 Supplement, Abstract B181.

Wacheck, V. et al. (2003). "Small interfering RNA targeting bcl-2 sensitizes malignant melanoma," *Oligonucleotides* 13(5):393-400.

Walboomers, M. et al. (Sep. 1999). "Human papillomavirus is a necessary cause of invasive cervical cancer worldwide," *J. Pathol.* 189(1):12-19.

Written Opinion dated Aug. 21, 2014, for PCT Patent Application No. PCT/US2014/029606 filed on Mar. 14, 2014, four pages.

Written Opinion dated Nov. 17, 2014, for PCT Application No. PCT/US2014/029602, filed on Mar. 14, 2014.

(56) References Cited

OTHER PUBLICATIONS

Zaug, A. J. et al. (May 11, 1984). "A labile phosphodiester bond at the ligation junction in a circular intervening sequence RNA," *Science* 224(4649):574-578.

Zhang, S. et al. (Jun. 1, 2008). "Identification and characterization of ovarian cancer-initiating cells from primary human tumors," Cancer Res. 68(11):4311-4320.

Figure 10
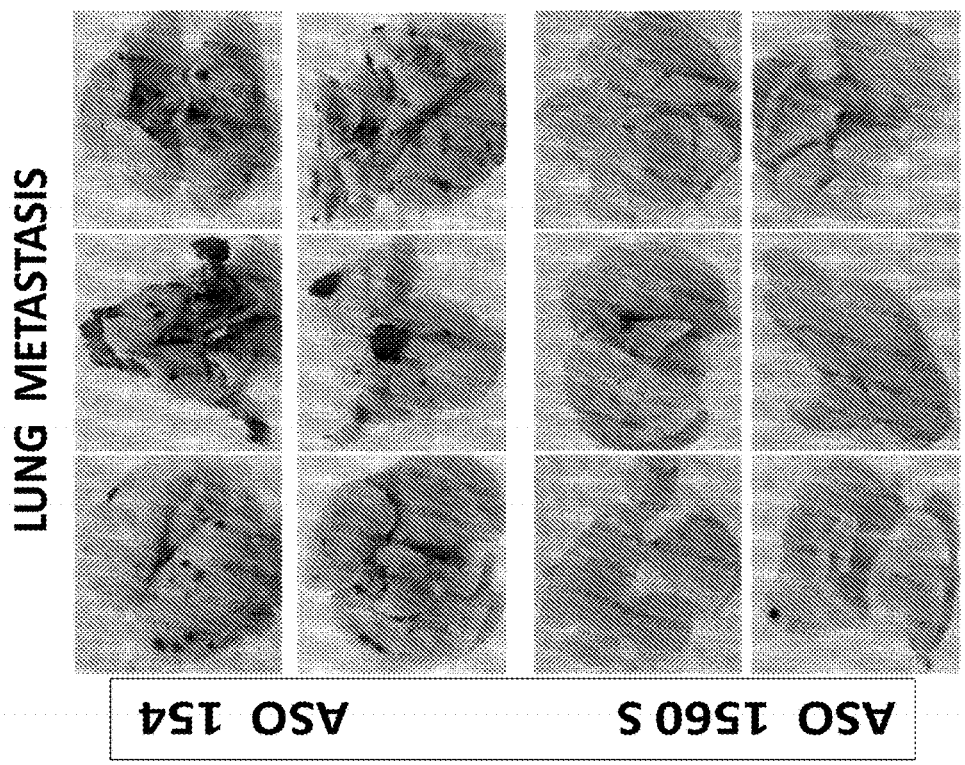
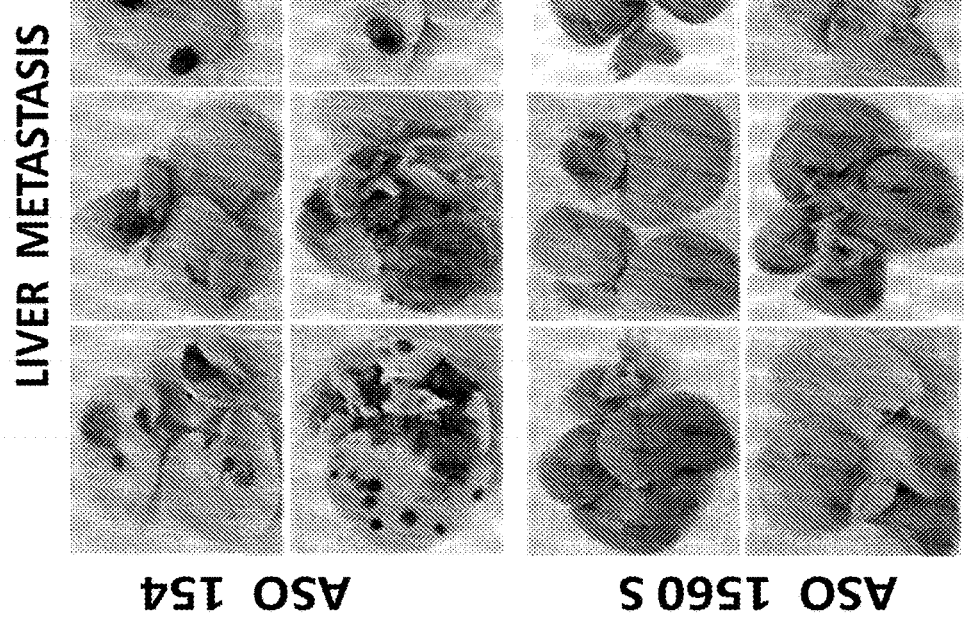

ANTISENSE OLIGONUCLEOTIDES FOR TREATMENT OF CANCER STEM CELLS

CROSS-REFERENCE TO RELATED APPLICATIONS

This application is a continuation of U.S. patent application Ser. No. 14/775,654, filed Sep. 11, 2015, which is a National Phase filing under 35 U.S.C. § 371 of International Application No. PCT/US2014/029606, filed Mar. 14, 2014, which claims the priority benefit of U.S. Provisional Patent Application Ser. No. 61/785,269, filed Mar. 14, 2013, U.S. Provisional Patent Application Ser. No. 61/790,072, filed Mar. 15, 2013, and U.S. Provisional Patent Application Ser. No. 61/937,438, filed Feb. 7, 2014, the entire contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 051738-503C01USSeqList.txt, original date created: Dec. 18, 2015, size: 63 KB).

FIELD OF THE INVENTION

This invention relates to oligonucleotides complementary to a non-coding chimeric mitochondrial RNA and their use in methods of treating and preventing metastasis or relapse of a cancer in an individual previously treated for cancer. The invention also relates to oligonucleotides complementary to a non-coding chimeric mitochondrial RNA and their use in treating a refractory cancer (e.g., a refractory HPV associated cancer) in an individual.

BACKGROUND OF THE INVENTION

Cancer is a cellular malignancy whose unique trait, loss of normal control of cell cycle, results in unregulated growth, lack of differentiation, and ability to invade other tissues and metastasize. Carcinogenesis is a multi-step process by which a normal cell is transformed in a malignant cell (McKinnell et al., "The Biology Basis of Cancer", Ch. 3, 1998). The etiology of cancer is complex and includes alteration of the cell cycle regulation, chromosomal abnormalities and chromosomes breakage. Infectious agents (e oncogenic viruses), chemicals, radiation (e.g., ultraviolet or ionizing radiation) and immunological disorders are thought to be the major causes of carcinogenesis (McKinnell et al., "The Biological Basis of Cancer, Ch. 3, 1998).

Recent evidence supports the view that tumors are organized in a hierarchy of heterogeneous cell populations with different biological properties. Two models have been proposed to account for this heterogeneity within tumors and for tumor growth. One such model is based on cancer stem cells (CSCs) which are thought to be responsible for aspects of cancer such as initiation, progression, metastasis, and recurrence. See Chen et al., *Acta Pharmacol Sin.*, 34(6): 732-740, 2013; Ponti et al., *Cancer Res*, 65(13):5506-11, 2005; Singh et al., *Cancer Res*, 63:5821-5828, 2003; and Feng et al., *Oncology Reports*, 22:1129-1134, 2009. Although CSCs generally represent a very small population of the overall tumor population, they are generally regarded as a self-renewing initiation subpopulation of tumor cells or a small population of cancer cells that are capable of giving rise to new tumors. CSCs have been identified in a number of cancers including, but not limited to, breast, brain, blood, liver, kidney, cervical, ovarian, colon, and lung cancers among others. See Ponti et al., *Cancer Res*, 65(13):5506-11, 2005; Feng et al., *Oncology Reports*, 22:1129-1134, 2009; Zhang et al., *Cancer Res*, 68(11):4311:4320, 2008; Singh et al., *Cancer Res*, 63:5821-5828, 2003; Clarke et al., *Cancer Res*, 66:9339, 2006; Sendurai et al., *Cell*, 133:704, 2008; Ohata et al., *Cancer Ides*, 72:5101, 2012; and Mukhopapadhyay et al., *Plos One*, 8(11):e78725, 2013).

Surgical resection of tumor(s) or metastases arising from a primary tumors) followed by systemic administration of anti-cancer therapy is the established clinical protocol for treatment of several cancers. Although successful for treatment of some cancer types, a well-known complication of cancer treatment is the survival of residual tumor cells or CSCs that are not effectively removed which can result in relapse after remission, with the cancer returning at the primary site of tumor formation or at distant sites due to metastasis. Recently, it was found that CSCs may also contribute to relapse after remission due to resistance to chemotherapy. See Domingo-Domenech et al., *Cancer Cell*, 22(3):373, 2012. Therefore, there is a need for development of therapeutic agents that can target cells which contribute to relapse and metastasis (e.g., CSCs). Discovery of such therapeutic agents may allow for the development of treatment useful for preventing, recurrence of cancer after remission (i.e., relapse) or preventing the spread of the primary tumour to secondary sites (i.e., metastasis). See Clarke et al., *Cancer Res*, 66:9339, 2006.

All references cited herein, including patent applications, patent publications, and scientific literature, are herein incorporated by reference as if each individual reference were specifically and individually indicated to be incorporated by reference.

SUMMARY OF THE INVENTION

The invention provided herein discloses, inter alia, methods for suppressing metastasis of a cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In some embodiments, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In one aspect, the invention provided herein discloses, methods for preventing relapse of cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In yet another aspect, the invention provided herein discloses, methods for the treatment of metastatic cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4. SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the metastatic cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In yet another aspect, the invention provided herein discloses, methods for the treatment of a refractory cancer (e.g., a refractory HPV-associated cancer) in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In another aspect, the invention herein provides kits comprising one or more oligonucleotide complementary to an antisense non-coding chimeric mitochondrial RNA (ASncmtRNA) molecule or a sense non-coding chimeric mitochondrial RNA (SncmtRNA) molecule and instructions for practicing any method disclosed herein.

BRIEF DESCRIPTION OF THE DRAWINGS

FIG. 10 depicts the presence of tumor relapse metastatic black nodules in the lung and livers of the mice treated with Control Oligo 154 but not in the lungs and livers mice treated with ASO 1560S.

DETAILED DESCRIPTION

Figure 1:
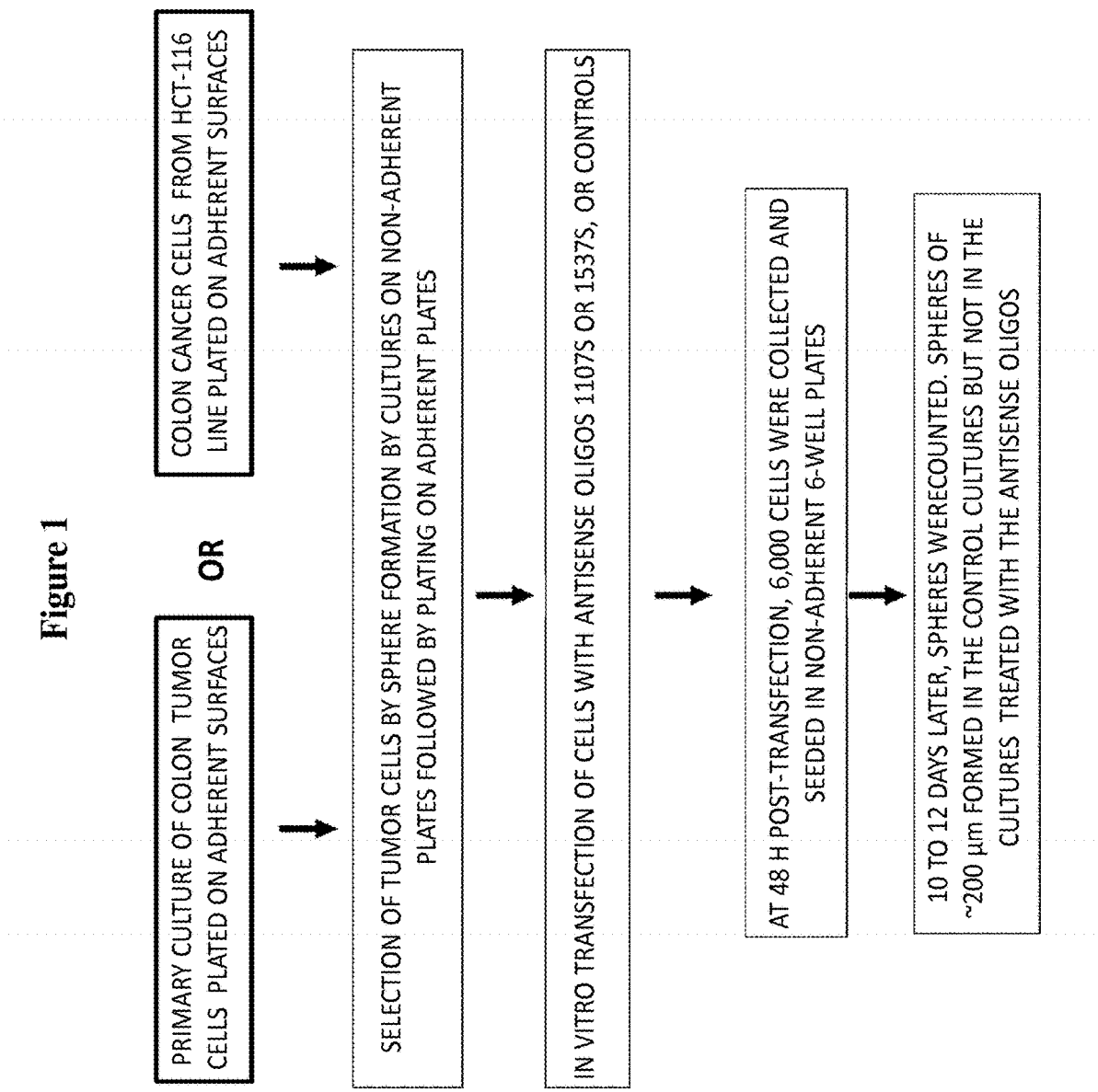
FIG. 1 depicts a general scheme of the experimental procedure and the assay utilized herein to measure the effect of antisense oligonucleotides targeted to ASncmtRNA on the number of spheres formed in colon cancer cells, based on the specific ability of cancer stem cells to form these spheroid bodies.

The invention provided herein discloses, inter alia, compositions comprising one or more oligonucleotide complementary to an antisense non-coding chimeric mitochondrial RNA (ASncmtRNA) molecule or a sense non-coding chimeric mitochondrial RNA (SncmtRNA) molecule and uses thereof for suppressing metastasis of a cancer in an individual. In certain embodiments, the invention provides compositions comprising one or more oligonucleotide complementary to an ASncmtRNA molecule or a SncmtRNA molecule and uses thereof for treating or preventing relapse of a cancer in an individual. In certain embodiments, the invention provides compositions comprising one or more oligonucleotide complementary to an ASncmtRNA molecule or a SncmtRNA molecule and uses thereof for treating metastatic cancer in an individual. In certain embodiments, the invention provides compositions comprising one or more oligonucleotide complementary to an ASncmtRNA molecule or a SncmtRNA molecule and uses thereof for treating a refractory cancer (e.g., a refractory HPV-associated cancer) in an individual. In some of the embodiments herein, the individual has been previously treated for cancer with a therapy (e.g., chemotherapy, radiation therapy, surgery or combinations thereof).

I. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); PCR: The Polymerase Chain Reaction, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987). Other useful references include Harrison's *Principles of Internal Medicine* (McGraw Hill; J. Isseleacher et al., eds.), Dubois' *Lupus Erythematosus* (5th ed.; D. J. Wallace and B. H. Hahn, eds.

II. Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting.

As used herein, the singular form "a". "an", and "the" includes plural references unless indicated otherwise. Thus, for example, reference to "an oligonucleotide" optionally includes a combination of two or more such oligonucleotides, and the like.

It is understood that aspects and embodiments of the invention described herein include "comprising," "consisting," and "consisting essentially of" aspects and embodiments.

An "isolated" nucleic acid molecule (e.g., "isolated oligonucleotide") is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells.

As used herein, the term "oligonucleotide complementary to an antisense non-coding chimeric mitochondrial RNA" or "oligonucleotide complementary to a sense non-coding chimeric mitochondrial RNA" refers to a nucleic acid having sufficient sequence complementarity to a target antisense non-coding chimeric mitochondrial RNA or a target sense non-coding chimeric mitochondrial RNA, respectively. An oligonucleotide "sufficiently complementary" to a target antisense non-coding chimeric mitochondrial RNA or a target sense non-coding chimeric mitochondrial RNA means that the oligonucleotide has a sequence sufficient to hybridize with the chimeric mitochondrial RNA molecules to form a stable duplex.

The term "oligonucleotide" refers to a short polymer of nucleotides and/or nucleotide analogs. An "oligonucleotide composition" of the invention includes any agent, compound or composition that contains one or more oligonucleotides, and includes, e.g., compositions comprising both single stranded and/or double stranded (ds) oligonucleotides, including, e.g., single stranded RNA, single stranded DNA, DNA/DNA and RNA/DNA hybrid oligonucleotides, as well as derivatized/modified oligonucleotides thereof. Such "oligonucleotide compositions" may also include amplified oligonucleotide products, e.g., polymerase chain reaction (PCR) products. An "oligonucleotide compositions" of the invention may also include art-recognized compositions designed to mimic the activity of oligonucleotides, such as peptide nucleic acid (PNA) molecules.

The phrase "corresponds to" or "sequence corresponding to" as it relates to RNA described herein (e.g., ASncmtRNA), indicates that the RNA has a sequence that is identical to or substantially the same as an RNA, or an RNA encoded by an analogous DNA, described herein. For example, an ASncmtRNA that corresponds to SEQ ID NO:4 indicates that the ASncmtRNA has a sequence that is identical to or substantially the same as the RNA of SEQ ID NO:203 or the RNA encoded by the analogous DNA of SEQ ID NO:4.

"Percent (%) nucleic acid sequence identity" or "percent (%) complementary" with respect to a reference nucleotide sequence (e.g., SncmtRNA sequence or ASncmtRNA sequence) is defined as the percentage of nucleic acid residues in a candidate sequence (e.g., oligonucleotide sequence) that are identical with the nucleic acid residues in the reference nucleotide sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

$$100 \text{ times the fraction } X/Y$$

where X is the number of nucleic acid residues scored as identical matches by the sequence in that program's alignment of A and B, and where Y is the total number of nucleic acid residues in B. It will be appreciated that where the length of nucleic acid sequence A is not equal to the length of nucleic acid sequence B, the % nucleic acid sequence identity of A to B will not equal the % nucleic acid sequence identity of B to A.

A "disorder" or "disease" is any condition that would benefit from treatment with a substance/molecule or method of the invention. This includes chronic and acute disorders or diseases including those pathological conditions which predispose the mammal to the disorder in question. In one embodiment, the disorder or disease is cancer. In another embodiment, the disorder or disease is metastatic cancer.

The term "cancer" refers to or describes the physiological condition in mammals that is typically characterized by unregulated cell growth/proliferation. Examples of cancer include but are not limited to, lymphoma, blastoma, sarcoma, and leukemia.

The terms "metastatic cancer" or "cancer metastasis" refer to a primary cancer capable of metastasis or cancer which has spread (i.e., metastasized) from a primary cancer, primary cancerous tissue or primary cancerous cells (e.g., cancer stem cells) from one part of of the body to one or more other parts of the body to form a secondary cancer or secondary cancers. Metastatic cancer or cancer metastasis also refer to locally advanced cancer that has spread from a primary cancer to nearby tissue(s) or lymph node(s). Metastatic cancer includes tumors that are defined as being high grade and/or high stage, for example tumors with a Gleason score of 6 or higher in prostate cancer are more likely to metastasize. Metastatic cancer also refers to tumors defined by one or more molecular markers that correlate with the metastasis.

The terms "relapsed cancer", "relapse of a cancer", "cancer relapse", or "tumor relapse" refer to the return or reappearance of cancer after a period of improvement. Typically the period of improvement is after administration of a therapy that resulted in the decrease of or disappearance of signs and symptoms of cancer. The period of improvement can be the decrease or disappearance of all signs and symptoms of cancer. The period of improvement can also be the decrease or disappearance of some, but not all, signs and symptoms of cancer. In some embodiments, the relapsed cancer is a cancer that has become unresponsive or partially unresponsive to a drug or a therapy. For example and without limitation, relapsed cancer includes cancer in patients whose first progression occurs in the absence of any treatment following successful treatment with a drug or a therapy; cancer in patients who progress on a treatment, or within 60 days of the treatment; and cancer in patients who progress while receiving treatment.

The terms "cancer stem cell", "cancer stem cells" or "CSCs" as used herein refer to a subpopulation of tumor cells or cancer cells. Cancer stem cells possess characteristics associated with normal stem cells, such as the ability to give rise to different cell types found in a particular cancer or tumor. Cancer stem cells have the capacity to drive the production or formation of a tumor or tumors through self-renewal and/or differentiation. Cancer stem cells have been identified in a number of cancers including, but not limited to, breast, brain, blood, liver, kidney, cervical, ovarian, colon, and lung cancers among others.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or suppressing metastasis, decreasing the rate of disease progression, amelioration or palliation of the disease state, and remission or improved prognosis. In some embodiments, oligonucleotides described herein are used to prevent or suppress metastasis. An individual is successfully "treated", for example, using an oligonucleotide of the invention if the individual shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth or tumor relapse; and/or relief to some extent, one or more of the symptoms associated with the specific cancer; reduced morbidity and mortality, and improvement in quality of life issues.

As used herein, the term "prevention" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, oligonucleotides described herein are used to prevent or suppress metastasis.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of cancer (e.g., metastatic cancer), as known in the art. An individual having one or more of these risk factors has a higher probability of developing the disorder than an individual without one or more of these risk factors.

An "individual" or "subject" can be a vertebrate, a mammal, or a human. Mammals include, but are not limited to, farm animals (such as cows), sport animals, pets (such as horses), primates, mice and rats. Individuals also include companion animals including, but not limited to, dogs and cats. In one aspect, an individual is a human.

A "healthcare professional," as used herein, can include, without limitation, doctors, nurses, physician assistants, lab technicians, research scientists, clerical workers employed by the same, or any person involved in determining, diagnosing, aiding in the diagnosis or influencing the course of treatment for the individual.

An "effective amount" refers to an amount of therapeutic compound, such as an oligonucleotide or other anticancer therapy, administered to an individual, either as a single dose or as part of a series of doses, which is effective to produce a desired therapeutic or prophylactic result.

A "therapeutically effective amount" is at least the minimum concentration required to effect a measurable improvement of a particular disorder. A therapeutically effective amount herein may vary according to factors such as the disease state, age, sex, and weight of the patient, and the ability of the oligonucleotide to elicit a desired response in the individual. A therapeutically effective amount may also be one in which any toxic or detrimental effects of the oligonucleotide are outweighed by the therapeutically beneficial effects. In the case of cancer, the therapeutically effective amount of the oligonucleotide may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the oligonucleotide may prevent growth and/or kill existing cancer cells, it may be cytostatic and/or cytotoxic.

A "prophylactically effective amount" refers to an amount effective, at the dosages and for periods of time necessary, to achieve the desired prophylactic result. For example, a prophylactically effective amount of the oligonucleotides of the present invention is at least the minimum concentration that prevents or attenuates the development of at least one symptom of metastatic cancer.

Administration "in combination with" one or more further therapeutic agents includes simultaneous (concurrent) and consecutive administration in any order.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "package insert" is used to refer to instructions customarily included in commercial packages of therapeutic products, that contain information about the indications, usage, dosage, administration, contraindications and/or warnings concerning the use of such therapeutic products.

The term "about" as used herein refers to the usual error range for the respective value readily known to the skilled person in this technical field.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Oligonucleotides and Other Anti-Cancer Therapies

Human cells express a number of unique chimeric mitochondrial RNA molecules. These molecules are non-coding (i.e., they are not known to serve as a template for the translation of a protein) and comprise the 16S mitochondrial ribosomal RNA covalently linked at the 5' end to an inverted repeat sequence. Chimeric mitochondrial RNA molecules are found in two forms: sense and antisense.

The sense chimeric non-coding mitochondrial RNA (SncmtRNA) molecule corresponds to the 16S mitochondrial ribosomal RNA transcribed from the "H-strand" of the circular mitochondrial genome. Covalently linked to the 5' end of this RNA molecule is a nucleotide sequence or inverted repeat sequence corresponding to an RNA transcribed from the "L-strand" of the mitochondrial 16S gene. The size of the inverted repeat sequence in the SncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, or 800 nucleotides or more to between about 100-200, 150-250, 200-300, 250-350, 400-500, 450-550, 500-600, 550-650, 600-700, 650-750, or 700-800 nucleotides or more, including any number in between these values. In one embodiment, the inverted repeat sequence in the SncmtRNA corresponds to a fragment of 815 nucleotides of the RNA transcribed from the L-strand of the 16S gene of the mitochondrial genome. In another embodiment, the inverted repeat sequence in the SncmtRNA corresponds to a fragment of 754 nucleotides of the RNA transcribed from the L-strand of the 16S gene of the mitochondrial genome. In still another embodiment, the inverted repeat sequence in the SncmtRNA corresponds to a fragment of 694 nucleotides of the RNA transcribed from the L-strand of the 16S gene of the mitochondrial genome. In another embodiment, the SncmtRNA corresponds to SEQ ID NO: 1. SEQ ID NO:2, or SEQ ID NO:3. In another embodiment, the SncmtRNA comprises a sequence selected from the group consisting of SEQ ID NO:200, SEQ ID NO:201, and SEQ ID NO:202.

The antisense chimeric non-coding mitochondrial RNA (ASncmtRNA) molecule corresponds to the 16S mitochondrial ribosomal RNA transcribed from the "L-strand" of the circular mitochondrial genome. Covalently linked to the 5' end of this RNA molecule is a nucleotide sequence or the inverted repeat sequence corresponding to an RNA transcribed from the "H-strand" of the mitochondrial 16S gene. The size of the inverted repeat sequence in the ASncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800 nucleotides or more to between about 100-200, 150-250, 200-300, 250-350, 400-500, 450-550, 500-600, 550-650, 600-700, 650-750, or 700-800 or more, including any number in between these values. In another embodiment, the ASncmtRNA corresponds to SEQ ID NO:4, SEQ ID NO:5, or SEQ ID NO:6. In another embodiment, the ASncmtRNA comprises a sequence selected from the group consisting of SEQ ID NO:203, SEQ ID NO:204, and SEQ ID NO:205.

Further information related to chimeric mitochondrial RNA molecules can be found in U.S. Pat. No. 8,318,686, the disclosure of which is incorporated by reference herein in its entirety.

In one aspect, the invention provides one or more oligonucleotide complementary to an ASncmtRNA molecule or a SncmtRNA molecule, wherein the oligonucleotide is able to hybridize with the chimeric mitochondrial RNA molecules to form a stable duplex for use in a method disclosed herein. In some aspects, provided herein are methods for suppressing metastasis of a cancer in an individual using one or more oligonucleotides described herein. In some aspects, provided herein are methods for treating or preventing relapse of a cancer in an individual. In some aspects, provided herein are methods for treating metastatic cancer in an individual. In some embodiments herein, the individual has been previously treated for cancer with a therapy (e.g., chemotherapy, radiation therapy, surgery or combinations thereof). In some embodiments, the one or more oligonucleotide complementary to an ASncmtRNA molecule or a SncmtRNA molecule described herein has or more of the following characteristics when used in a method disclosed herein: (1) hybridizes with the chimeric mitochondrial RNA molecules (i.e., an ASncmtRNA molecule or a SncmtRNA molecule) to form a stable duplex; (2) hybridizes with the chimeric mitochondrial RNA molecules expressed by tumor cells and inhibits, arrests, kills or abolishes tumor cells; (3) hybridizes with the chimeric mitochondrial RNA molecules expressed by cancer stem cells (CSCs) and inhibits, arrests, kills or abolishes CSCs; (4) suppresses metastasis of a cancer in an individual (e.g., an individual previously treated for cancer with a therapy); (5) treats or prevents relapse of a cancer in an individual (e.g., an individual previously treated for cancer with a therapy); (6) treats metastatic cancer in an individual (e.g., an individual previously treated for cancer with a therapy); and (7) prolongs overall survival in an individual previously treated for cancer with a therapy (e.g., chemotherapy, radiation therapy, surgery or combinations thereof).

In one aspect, the oligonucleotides for use in any of the methods described herein can be complementary to a SncmtRNA molecule and/or to an ASncmtRNA molecule disclosed herein. Without being bound to theory, it is believed that the complementary oligonucleotides bind to the ncmtRNAs and interfere with their cellular functions. As used herein, an oligonucleotide sequence is "complementary" to a portion of an ncmtRNA, as referred to herein, if the oligonucleotide possesses a sequence having sufficient complementarity to be able to hybridize with the ncmtRNA to form a stable duplex. The ability to hybridize will depend on both the degree of complementarity and the length of the oligonucleotide. Generally, the longer the hybridizing oligonucleotide, the more base mismatches with an ncmtRNA it may contain and still form a stable duplex. In some aspects, the one or more oligonucleotide used according to the methods disclosed herein is at least 8 (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more) base pairs in length. Those skilled in the art can ascertain a tolerable degree of mismatch by use of standard procedures to determine the melting point of the hybridized complex. In some embodiments, the one or more oligonucleotide is at least 85% (such as at least 86%, 87%, 88%, 89%, 90%, 91%, 92%, 93%, 94%, 95%, 96%, 97%, 98%, 99%, or 100%) complementary to a SncmtRNA molecule and/or to a ASncmtRNA molecule disclosed herein. In some embodiments, the complementary oligonucleotide is an antisense oligonucleotide. In one embodiment, the one or more oligonucleotide is complementary to one or more ncmtRNA encoded by a nucleic acid sequence selected from the group consisting of SEQ ID NOs: 1-6. In some embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198. In some embodiments, the one or more oligonucleotide comprises a nucleic acid sequence selected from the group consisting of SEQ ID NOs:36, 197 and 198.

a. Oligonucleotide Modifications

The naturally occurring internucleoside linkage of RNA and DNA is a 3' to 5 phosphodiester linkage. The oligonucleotides (e.g., an antisense oligonucleotide) used for suppressing metastasis of a cancer, treating or preventing relapse of a cancer, or treating metastatic cancer according to any of the methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases present in bodily fluids.

Oligonucleotides (e.g., an antisense oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known in the art.

In one embodiment, oligonucleotides (e.g., an antisense oligonucleotide) targeted to a SncmtRNA molecule and/or to an ASncmtRNA molecule disclosed herein comprise one or more modified internucleoside linkages. In some embodiments, the modified internucleoside linkages are phosphorothioate linkages.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific, though nonlimiting, examples of oligonucleotides (e.g., an antisense oligonucleotide) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also be employed. Various salts, mixed salts and free acid forms are also included. Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones: amide backbones; and others having mixed N, O, S and $CH_2$ component parts.

In other embodiments, both the sugar and the interucleoside linkage, i.e., the backbone, of the nucleotide units are replaced with novel groups. The base units are maintained for hybridization with an appropriate nucleic acid target compound. One such oligomeric compound, an oligonucleotide mimetic is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 254:1497-1500, 1991.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified oligonucleotides (e.g., antisense oligonucleotides) complementary to SncmtRNA and/or ASncmtRNA used as anticancer therapies in combination with any of the methods disclosed herein (e.g., method of suppressing metastasis of a cancer) may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

The oligonucleotides (e.g., antisense oligonucleotides) for use in the methods disclosed herein (e.g., method of suppressing metastasis of a cancer) can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O (CH$_2$)$_2$—OCH$_3$ (2'-O-methoxyethyl or 2'-MOE) substituent group; and bicyclic modified sugars (BNAs), having a 4'-(CH$_2$)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In other embodiments, the bicyclic sugar moiety comprises a bridge group between the 2' and the 4'-carbon atoms. In certain such embodiments, the bridge group comprises from 1 to linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

Oligonucleotides (e.g., antisense oligonucleotides) for use in any of the methods disclosed herein (e.g., method of suppressing metastasis of a cancer) may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as an ncmtRNA).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (I H-pyrimido[5,4-b][1,4]benzothiazin-2(3H)-one), O-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B. ed., CRC Press, 1993.

Representative United States patents that teach the preparation of certain of the above noted modified nucleobases as well as other modified nucleobases include, but are not limited to, U.S. Pat. Nos. 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, each of which is herein incorporated by reference.

b. Ribozymes

In another embodiment of the invention, ribozymes can be used to interfere with the ncmtRNA molecules described herein to induce cell death in proliferative cells associated with mestastasis (e.g., CSCs). The sequence of the ribozyme can be designed according to the sequence of the ASncmtRNA (for example, a sequence corresponding to SEQ ID NO:4, SEQ ID NO:5, or SEQ ID NO:6, or a sequence comprising SEQ ID NO:203, SEQ ID NO:204, or SEQ ID NO:205) or the SncmtRNA (for example, a sequence corresponding to SEQ ID NO: 1, SEQ ID NO:2, or SEQ ID NO:3, or a sequence comprising SEQ ID NO:200, SEQ ID NO:202, or SEQ ID NO:203) to cleave specific regions of the transcript. Ribozymes are enzymatic RNA molecules capable of catalyzing the specific cleavage of RNA (Rossi, *Curr. Biology* 4:469-471, 1994). The mechanism of ribozyme action involves sequence specific hybridization of the ribozyme molecule to complementary target RNA, followed by an endonucleolytic cleavage. The composition of ribozyme molecules must include one or more sequences complementary to the RNA, and must include the well-known catalytic sequence responsible for RNA cleavage, and described in U.S. Pat. No. 5,093,246, the disclosure of which is incorporated by reference herein in its entirety. As such, within the scope of the invention, hammerhead ribozyme molecules can be engineered that specifically and efficiently catalyze endonucleolytic cleavage of the ASncmtRNA or SncmtRNA molecules disclosed herein. The construction and production of hammerhead ribozymes is well known in the art and it was described (Haseloff et al., *Gene*, 82:43-52, 1989). Ribozymes of the present invention can also include RNA endoribonucleases (Zaug et al., *Science*, 224:574-578, 1984). In some embodiments, a ribozyme described herein can be used in any method described herein. In some embodiments, a method of suppressing metastasis of a cancer in an individual comprises administering to the individual an effective amount of one or more ribozyme described herein. In some embodiments, a method for treating or preventing relapse of cancer in an individual comprises administering to the individual an effective amount of one or more ribozyme described herein. In some embodiments, a method for treating metastatic cancer in an individual comprises administering to the individual an effective amount of one or more ribozyme described herein. In some embodiments, a method for treating a refractory cancer (e.g., a refractory HPV-associated cancer) in an individual comprises administering to the individual an effective amount of one or more ribozyme described herein. In some embodiments, the individual has been previously treated for cancer with a therapy (e.g., chemotherapy, radiation therapy, surgery or combinations thereof).

c. RNA Interference

In another aspect, interference with the function of the ASncmtRNA and/or SncmtRNA molecules disclosed herein for use in any of the methods disclosed herein (e.g., method of suppressing metastasis of a cancer) can be achieved by RNA interference or RNA silencing. RNA interference (RNAi) has emerged as a novel and promising approach for gene silencing in mammalian cells (Elbashir et al., *Nature* 411:494-498, 2001; McManus et al., *Nature Rev.* Genet. 3:737-747, 2002). Synthetically synthesized double stranded RNA molecules of about 8 to 40 (such as about 10 to 36, 14 to 32, 18-28, or 22-24) base pairs (bp) or at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length hybridize specifically to their complementary target RNA, leading to degradation of the RNA. Several different genes have been silenced successfully by small interfering RNA or siRNA (Lu et al., *Curr. Opin. Mol. Ther.* 5:225-234, 2003; Wacheck et al., *Oligonucleotides* 13:393-400, 2003). Therefore, synthetic double stranded RNA targeted to the ASncmtRNA and/or SncmtRNA molecules disclosed herein can be used to degrade these transcripts and induce cancer cell death (e.g., CSC death). Those familiar in the art will understand that the sequence of the siRNA has to be complementary to any region of the ASncmtRNA and/or SncmtRNA molecules (such as complementary to any one of a sequence corresponding to SEQ ID NO:1. SEQ ID NO:2, SEQ ID NO:3, SEQ ID NO:4, SEQ ID NO:5, and/or SEQ ID NO:6, or complementary to any one of a sequence comprising SEQ ID NO:200, SEQ ID NO:201, SEQ ID NO:202, SEQ ID NO:203, SEQ ID NO:204, and/or SEQ ID NO:205). In some embodiments, an RNA described herein can be used in any method described herein. In some embodiments, a method of suppressing metastasis of a cancer in an individual comprises administering to the individual an effective amount of one or more RNA described herein. In some embodiments, a method for treating or preventing relapse of cancer in an individual comprises administering to the individual an effective amount of one or more RNA described herein. In some embodiments, a method for treating metastatic cancer in an individual comprises administering to the individual an effective amount of one or more RNA described herein. In some embodiments, a method for treating a refractory cancer (e.g., a refractory HPV-associated cancer) in an individual comprises administering to the individual an effective amount of one or more RNA described herein. In some embodiments, the individual has been previously treated for cancer with a therapy (e.g., chemotherapy, radiation therapy, surgery or combinations thereof).

d. Oligonucleotide Delivery

In one embodiment, a recombinant vector can be used for delivering one or more oligonucleotides (such as any of the oligonucleotides disclosed herein) complementary to a sense and/or antisense chimeric non-coding mitochondrial RNA molecule to the individual. This can include both systemic delivery and delivery localized to a particular region of the body (such as, the bone marrow). Any vector capable of enabling recombinant production of one or more oligonucleotides complementary to a sense or antisense chimeric ncmtRNA molecule and/or which can deliver one or more oligonucleotides complementary to a sense or antisense chimeric ncmtRNA molecule into a host cell is contemplated herein. The vector can be either RNA or DNA, either prokaryotic or eukaryotic, and typically is a virus or a plasmid. The vector can be part of a DNA vaccine or used as part of any other method for delivering a heterologous gene for expression in a host cell that is known to one having skill in the art. Recombinant vectors are capable of replicating when transformed into a suitable host cell. Viral vectors infect a wide range of non-dividing human cells and have been used extensively in live vaccines without adverse side effects. A viral vector (such as, but not limited to, an adenoviral vector or an adeno-associated viral (AAV) vector (e.g. AAV-1, AAV-2, AAV-3, AAV-4, AAV-5, AAV-6, etc. or hybrid AAV vectors comprising the same) is an example of a vector for use in the present methods for delivering one or more oligonucleotides complementary to a sense or antisense chimeric ncmtRNA molecule to cancer cells (such as a plasmocyte; see, e.g. U.S. Patent Application Publication No. 2004/0224389, the disclosure of which is incorporated by reference herein, or a CSC). In some embodiments, a recombinant vector (e.g., a viral vector) described herein can be used in any method described herein. In some embodiments, a method of suppressing metastasis of a cancer in an individual comprises administering to the individual an effective amount of a recombinant vector (e.g., a viral vector) comprising one or more oligonucleotide described herein. In some embodiments, a method for treating or preventing relapse of cancer in an individual comprises administering to the individual an effective amount of a recombinant vector (e.g., a viral vector) comprising one or more oligonucleotide described herein. In some embodiments, a method for treating metastatic cancer in an individual comprises administering to the individual an effective amount of a recombinant vector (e.g., a viral vector) comprising one or more oligonucleotide described herein. In some embodiments, a method for treating a refractory cancer (e.g., a refractory HPV-associated cancer) in an individual comprises administering to the individual an effective amount of a recombinant vector (e.g., a viral vector) comprising one or more oligonucleotide described herein. In some embodiments, the individual has been previously treated for cancer with a therapy (e.g., chemotherapy, radiation therapy, surgery or combinations thereof).

In another aspect, one or more oligonucleotides (such as any of the oligonucleotides disclosed herein) complementary to a sense and/or antisense chimeric non-coding mitochondrial RNA molecule is encapsulated within a microcarrier for deliver to an individual. In certain embodiments, a mixture of different oligonucleotides (such as any of the oligonucleotides disclosed herein) complementary to a sense and/or antisense chimeric non-coding mitochondrial RNA molecule may be encapsulated with a microcarrier, such that the microcarrier encapsulates more than one oligonucleotide species. In some embodiments, the one or more oligonucleotides (such as any of the oligonucleotides disclosed herein) complementary to a sense and/or antisense chimeric non-coding mitochondrial RNA molecule encapsulated within the microcarrier comprises a nucleic acid sequence selected from the group consisting of SEQ ID NOs:7-198. In some embodiments, the one or more oligonucleotides (such as any of the oligonucleotides disclosed herein) complementary to a sense and/or antisense chimeric non-coding mitochondrial RNA molecule encapsulated within the microcarrier comprises a nucleic acid sequence selected from the group consisting of SEQ ID NOs:36, 197 and 198.

Methods of encapsulating oligonucleotides in microcarriers are well known in the art, and described, for example, International application WO98/55495. Colloidal dispersion systems, such as microspheres, beads, macromolecular complexes, nanocapsules and lipid-based system, such as oil-in-water emulsions, micelles, mixed micelles and liposomes can provide effective encapsulation of oligonocelotides within microcarrier compositions. The encapsulation composition may further comprise any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Other Anti-Cancer Therapies

In some aspects, any of the methods of treatment described herein can comprise administering one or more additional anti-cancer therapies to the individual. In some embodiments, the one or more anti-cancer therapy is selected from the group consisting of chemotherapy, radiation therapy, and surgery. Chemotherapy and anti-cancer agents are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used herein. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type TI inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are *vinca* alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some aspects, the anti-cancer agent can be selected from remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, gefitinib (Iressa®), taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, or etoposide.

In other embodiments, the anti-cancer agent can be selected from bortezomib, cyclophosphamide, dexamethasone, doxorubicin, interferon-alpha, lenalidomide, melphalan, pegylated interferon-alpha, prednisone, thalidomide, or vincristine.

In some aspects, the one or more anti-cancer therapy is radiation therapy. As used herein, the term "radiation therapy" refers to the administration of radiation to kill cancerous cells. Radiation interacts with molecules in the cell such as DNA to induce cell death. Radiation can also damage the cellular and nuclear membranes and other organelles. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray. Radiation also contemplated herein includes, for example, the directed delivery of radioisotopes to cancer cells. Other forms of DNA damaging factors are also contemplated herein such as microwaves and UV irradiation.

Radiation may be given in a single dose or in a series of small doses in a dose-fractionated schedule. The amount of radiation contemplated herein ranges from about 1 to about 100 Gy, including, for example, about 5 to about 80, about 10 to about 50 Gy. or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted. When the radiation comprises use of radioactive isotopes, the isotope may be conjugated to a targeting agent, such as a therapeutic antibody, which carries the radionucleotide to the target tissue (e.g., tumor tissue). Suitable radioactive isotopes include, but are not limited to, astatine$^{211}$, $^{14}$carbon, $^{51}$chromium, $^{36}$chlorine, $^{57}$iron, $^{58}$cobalt, copper$^{67}$, $^{152}$Eu, gallium$^{67}$, ^hydrogen, iodine$^{123}$, iodine$^{131}$, indium$^{111}$, $^{59}$ion, $^{32}$phosphorus, rhenium$^{186}$, $^{75}$selenium, $^{35}$sulphur, technicium$^{99m}$, and/or yttrium °.

Surgery described herein includes resection in which all or part of a cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of precancers or normal tissues is also contemplated herein.

Stem Cell Transplantation and Ex Vivo Treatment of Autologous Hematopoietic Stem Cells In other aspects, any of the methods of treatment described herein can include either autologous or allogenic stem cell transplantation therapy. In recent years, high-dose chemotherapy with autologous hematopoietic stem-cell transplantation has become the preferred treatment for certain cancers such as multiple myeloma, non-Hodgkin lymphoma, Hodgkin lymphoma, and leukemia. While not curative, this procedure does prolong overall survival and complete remission. Prior to stem-cell transplantation, patients receive an initial course of induction chemotherapy. The most common induction regimens used today are thalidomide-dexamethasone, bortezomib based regimens, and lenalidomide-dexamethasone (Kyle & Rajkumar, *Blood*, 111 (6): 2962-72, 2008). For example, autologous peripheral stem cell transplantation is useful for up to 50% of multiple myeloma patients. Despite a low mortality rate, problems with such transplant therapy include the inability to eradicate the tumor and the difficulty in the removal of myeloma cells and their precursors from the stem cell collection used for transplantation.

Allogenic transplant (the transplantation of a healthy person's stem cells into the affected individual), is another therapy option for treating certain cancers such as multiple myeloma, non-Hodgkin lymphoma, Hodgkin lymphoma, and leukemia but is less frequently used as it may not provide a cure. For example, most studies evaluating its use in multiple myeloma patients demonstrate long-term disease-free survival of 10-20%, with a significant fraction of patients developing relapse.

When included as a treatment for suppressing or preventing metastasis according to any of the methods disclosed herein, autologous stem cell transplantation can also include the step of treating the hematopoietic stem-cells and/or bone marrow to be transplanted into the affected individual with any of the anti-cancer agents disclosed herein, prior to transplantation into the affected individual. In one embodiment, hematopoietic stem-cells and/or bone marrow for use in autologous stem cell transplantation can be treated with an effective amount of one or more oligonucleotides (e.g., antisense oligonucleotides) sufficiently complementary to an ASncmtRNA or SncmtRNA molecule (e.g., any of the ASncmtRNA and/or SncmtRNA molecules disclosed herein) to form a stable duplex prior to transplantation into the affected individual. In another embodiment, the one or more oligonucleotide is sufficiently complementary to one or more ncmtRNA encoded by a nucleic acid sequence selected from the group consisting of SEQ ID NOs: 1-6, to form a stable duplex. In other embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198.

It has been shown that autologous transplantation of bone marrow or hematological stem cells can also be used to treat several forms of hematological cancers (such as, but not limited to, multiple myeloma, leukemia and lymphoma). Accordingly, in some aspects, when included as a treatment for a hematological cancer, provided herein is a method of performing autologous stem cell transplantation which includes the step of treating the hematopoietic stem-cells and/or bone marrow to be transplanted into the affected individual with any of the anti-cancer agent disclosed herein, prior to transplantation into the affected individual. In one embodiment, hematopoietic stem-cells and/or bone marrow for use in autologous stem cell transplantation in an individual with a hematological cancer can be treated with an effective amount of one or more oligonucleotides (e.g., antisense oligonucleotides) sufficiently complementary to an ASncmtRNA molecule or SncmtRNA molecule (e.g., any of the ASncmtRNA and/or SncmtRNA molecules disclosed herein) to form a stable duplex prior to transplantation into the affected individual. In another embodiment, the one or more oligonucleotide is sufficiently complementary to one or more ncmtRNA encoded by a nucleic acid sequence selected from the group consisting of SEQ 1D NOs:1-6, to form a stable duplex. In other embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198.

IV. Compositions

Any of the anti-cancer agents (such as oligonucleotide-based agents) disclosed herein can be administered in the form of compositions (e.g., pharmaceutical compositions). These compounds can be administered by systemic administration or local administration through various routes. The route(s) of administration useful in a particular application are apparent to one of skill in the art. Routes of administration include but are not limited to oral, rectal, cerebrospinal, transdermal, subcutaneous, topical, transmucosal, nasopharangeal, pulmonary, intravenous, intramuscular, and intranasal. In some embodiments, the administration is a local administration. In some embodiments, the local administration is selected from the group consisting of administration into an organ, into a cavity, into a tissue, and subcutaneous administration. In some embodiments, the administration is systemic administration. In some embodiments, the systemic administration is intravenous or intraperitoneal administration. These compounds are effective as both injectable and oral compositions. Such compositions are prepared in a manner well known in the pharmaceutical art and comprise at least one active compound. The compositions herein may also contain more than once active compound as necessary for the particular indication being treated, preferably those with complementary activities that do not adversely affect each other. When employed as oral compositions, the oligonucleotides, and other anti-cancer agents disclosed herein, are protected from acid digestion in the stomach by a pharmaceutically acceptable protectant.

This invention also includes pharmaceutical compositions which contain, as the active ingredient, one or more of the anti-cancer agents disclosed herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, in preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any one of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The anti-cancer agents (such as oligonucleotide-based agents) disclosed herein are effective over a wide dosage range and are generally administered in a therapeutically effective amount. It will be understood, however, that the amount of the anti-cancer agents actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient anticancer therapy is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the anticancer therapies (such as an oligonucleotide) from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Parenteral routes of administration include but are not limited to direct injection into a central venous line, intravenous, intramuscular, intraperitoneal, intradermal, or subcutaneous injection. Oligonucleotide (e.g., an oligonucleotide and microcarrier formulation) formulations suitable for parenteral administration are generally formulated in USP water or water for injection and may further comprise pH buffers, salts bulking agents, preservatives, and other pharmaceutically acceptable excipients. Oligonucleotide(s), for example as oligonucleotide microcarrier complexes or encapsulates, for parenteral injection may be formulated in pharmaceutically acceptable sterile isotonic solutions such as saline and phosphate buffered saline for injection.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

V. Methods of Treatment

A. Methods for Suppressing or Preventing Metastasis of a Cancer

In one aspect, provided herein is one or more oligonucleotide (or composition thereof) for use in suppressing or preventing metastasis of a cancer in an individual. In another aspect, provided herein is one or more oligonucleotide (or compositions thereof) for use in combination with at least one therapy for suppressing or preventing metastasis of a cancer in an individual. In any of the aspects, herein, the individual may have been previously treated for cancer with a therapy.

In some aspects, the invention provides a method for suppressing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

In some aspects, the invention provides a method for preventing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing or preventing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

As non-limiting examples, a method for suppressing or preventing metastasis of cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

B. Methods for Treating or Preventing Relapse of a Cancer

In other aspects, provided herein is one or more oligonucleotide (or compositions thereof) for use in treating or preventing relapse of a cancer in an individual. In some embodiments, the individual has responded to initial treatment and is in remission.

In some aspects, the invention provides a method for treating or preventing relapse of cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating or preventing relapse of cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

As non-limiting examples, a method for treating or preventing relapse of a cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In other embodiments, a "maintenance schedule" may be used in which one or more maintenance oligonucleotide-based (such as antisense-based) therapies are administered less frequency than in the original treatment administered prior to remission, such as once per week or once every two weeks. The maintenance schedule can be continued either for a fixed period of time, generally about 1 or about 2 years, or indefinitely as long as the patient is continuing to show no signs of progressive disease and is tolerating the treatment without significant toxicity.

C. Methods for Treating Metastatic Cancer

In yet other aspects, provided herein is one or more oligonucleotide (or compositions thereof) for use in treating metastatic cancer (such as relapsed metastatic cancer) in an individual.

In some aspects, the invention provides a method for the treatment of metastatic cancer (such as relapsed metastatic cancer) in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating metastatic cancer (such as relapsed metastatic cancer) in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

As non-limiting examples, a method for the treatment of metastatic cancer (such as relapsed metastatic cancer) according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In another embodiment, the therapeutically effective amount of said one or more oligonucleotide (or compositions thereof) is administered as part of a salvage therapy in treating an individual wherein the cancer has become refractory to other treatment for cancer. In some embodiments, the individual relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine.

Without being bound by theory, it is believed that CSCs give rise to the relapse and/or metastasis of a cancer following treatment of the primary tumor. In some aspects, methods of treatment as described herein (e.g., a method for suppressing or preventing metastasis of a cancer, etc.) eliminates or supresses cancer stem cells. In some embodiments, the oligonucleotides disclosed herein can kill or inhibit cancer stem cells (CSCs) to suppress metastasis, prevent metastasis or prevent relapse of a cancer in an individual. In some embodiments, the individual has been previously treated for cancer with a therapy. In one embodiment, the oligonucleotides disclosed herein can kill or inhibit cancer stem cells (CSCs) that are resistant to treatment (e.g., chemotherapy). In one embodiment, treatment of an individual with any one or more oligonucleotide disclosed herein (e.g., an oligonucleotide complementary to an ASncmtRNA molecule) non-selectively inhibits, arrests, kills, or abolishes the CSCs in the individual. In one embodiment, any one or more oligonucleotide disclosed herein (e.g., an oligonucleotide complementary to an ASncmtRNA molecule) reduces the number of CSCs in the individual as compared to an individual not administered the oligonucleotide. In a further embodiment, the individual has been previously treated for cancer with a therapy.

In any embodiments of the methods herein, any one or more oligonucleotide disclosed herein (e.g., an oligonucleotide complementary to an ASncmtRNA molecule) inhibits tumor growth and/or metastasis in the individual as compared to an individual not administered the oligonucleotide.

In any of the embodiments of the methods herein (e.g., a method for suppressing or preventing metastasis of a cancer, a method for treating or preventing relapse of a cancer, a method for treating metaststic cancer, etc.), the cancer may be a solid cancer or a non-solid cancer. In any of the embodiments herein, the cancer is a solid cancer. Examples of solid cancers contemplated herein include, without limitation, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, brain cancer, cervical cancer, ovarian cancer, liver cancer, sarcoma, bladder cancer, hepatoma, breast cancer, colon cancer, colorectal cancer, endometrial or uterine carcinoma, oralpharyngeal cancer, salivary gland carcinoma, renal cancer, liver cancer, prostate cancer, vulval cancer, thyroid cancer, hepatic carcinoma, gastric cancer, melanoma, and various types of head and neck cancer.

In some embodiments, the cancer is associated with a human papilloma virus (HPV) infection, also referred to herein as "HPV-associated cancer", such as in cervical cancer, oralpharyngeal cancer, and head and neck cancer. For example, one of the most important risk factors for development of cervical cancer is an HPV infection. Over 100 strains of HPV have been identified, however, only a subset are classified as high-risk (16, 18, 31, 33, 35, 39, 45, 51, 52, 56, 58, 59, 68, 73, and 82) or probable high-risk (26, 53, and 66) types for the development of cancer (Munoz et al., NEJM, 348:518-527, 2003). Of these HPV types. HPV16 and HPV18 are reported to cause nearly 70% of all cervical cancer cases while HPV 31 and 35 cause another 10% of cervical cancer cases. See Walboomers et al., J Pathol., 189(1): 12-9, 1999. HPV-associated cancer can involve one or more of the following steps: (1) initial HPV infection, (2) persistent HPV infection, (3) transforming HPV infection, in the presence or absence of integration of HPV DNA into the host cell genome, (4) development of precancerous lesions, (5) development of at least one primary tumor, and (6) development of invasive cancer (e.g., metastatic cancer).

In some instances, the HPV-associated cancer is resistant to chemotherapeutic agents regularly used for the treatment of cancer. For example, HPV 16-immortalized cervical cells can develop resistance to cisplatin, paclitaxel, actinomycin D, doxrubucin, etoposide, and 5-fluorouracil which presents a major obstacle in cancer treatment. See Ding et al., Int J Cancer, 15:87(6)818-23, 2000. In some embodiments herein, provided herein is one or more oligonucleotide (or compositions thereof) for use in suppressing metastasis of a cancer in an individual wherein the cancer is resistant to a chemotherapeutic agent, and wherein the cancer is an HPV-associated cancer. In some embodiments herein, provided herein is one or more oligonucleotide (or compositions thereof) for use in treating or preventing relapse of a cancer in an individual, wherein the cancer is resistant to a chemotherapeutic agent, and wherein the cancer is an HPV-associated cancer. In some embodiments herein, provided herein is one or more oligonucleotide (or compositions thereof) for use in treating metastatic cancer (such as relapsed metastatic cancer) in an individual, wherein the metastatic cancer is resistant to a chemotherapeutic agent, and wherein the metastatic cancer is an HPV-associated cancer. In some embodiments herein, provided herein is one or more oligonucleotide (or compositions thereof) for use in treating a refractory cancer in an individual. In some embodiments, the refractory cancer is a refractory HPV-associated cancer. In some embodiments, the refractory HPV-associated cancer is resistant to a chemotherapeutic agent. As used herein, the term "refractory cancer" refers to a cancer (e.g., an HPV-associated cancer) that does not respond to treatment, for example, a cancer that is resistant at the beginning of treatment (e.g., treatment with a chemotherapeutic agent) or a cancer that may become resistant during treatment. In some embodiments, the chemotherapeutic agent is selected from the group consisting of cisplatin, paclitaxel, actinomycin D, doxrubucin, etoposide, and 5-fluorouracil. In some embodiments, the chemotherapeutic agent is cisplatin. In some of the embodiments herein, the HPV-associated cancer (e.g., a refractory HPV-associated cancer) is from an infection with one or more HPV strains selected from the group consisting of HPV 16, HPV 18, HPV 31 and HPV 45. In some of the embodiments herein, the HPV-associated cancer (e.g., a refractory HPV-associated cancer) is from an infection with the HPV strain HPV 45. In some embodiments, the one or more oligonucleotide is complementary to the SncmtRNA molecule encoded by a nucleotide sequence selected from the group consisting of SEQ ID NO: 1, SEQ ID NO:2, and SEQ ID NO:3. In some embodiments, the one or more oligonucleotide is complementary to the ASncmtRNA molecule encoded by a nucleotide sequence selected from the group consisting of SEQ ID NO:4, SEQ ID NO:5, and SEQ ID NO:6. In some embodiments, the one or more oligonucleotide comprises a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198.

In some embodiments, provided herein is one or more oligonucleotide (or compositions thereof) for use in treating a refractory cancer in an individual. In some embodiments, the refractory cancer is resistant to a chemotherapeutic agent. In some embodiments, the chemotherapeutic agent is cisplatin. In some embodiments, the refractory cancer is a solid cancer disclosed herein. For example, the refractory solid cancer may be one or more of bladder cancer, brain cancer, breast cancer, cervical cancer (e.g., a refractory HPV-associated cervical cancer), colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In some embodiments, the refractory cancer is a non-solid cancer disclosed herein. For example, the refractory cancer may be one or more of multiple myeloma, leukemia, or lymphoma.

In any of the embodiments herein, the cancer is a non-solid cancer. "Non-solid cancer" refers to a hematological malignancy involving abnormal growth and/or metastasis of a blood cell. Examples of non-solid cancers contemplated herein include, without limitation, multiple myeloma, acute myeloid leukemia, acute lymphoblastic leukemia, chronic myelogenous leukemia, chronic lymphocytic leukemia, acute nonlymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, undifferentiated cell leukemia, idiopathic myelofibrosis, lymphoma (such as Non-Hodgkin's lymphoma, and Hodgkin's lymphoma), and myelodysplastic syndrome.

The methods disclosed herein can be practiced in an adjuvant setting. "Adjuvant setting" can refers to a clinical setting in which an individual has had a history of cancer, and generally (but not necessarily) been responsive to therapy, which includes, but is not limited to, surgery (such as surgical resection), radiotherapy, and chemotherapy. However, because of their history of the cancer (such as melanoma or colon cancer), these individuals are considered at risk of development of cancer. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease (cancer) when first treated.

The present invention is accordingly directed to methods for inhibiting the symptoms or conditions (disabilities, impairments) associated with cancer (e.g., metastatic cancer or relapsed cancer) as described in detail below. As such, it is not required that all effects of the condition be entirely prevented or reversed, although the effects of the presently disclosed methods likely extend to a significant therapeutic benefit for the individual. As such, a therapeutic benefit is not necessarily a complete prevention or cure for the condition, but rather, can encompass a result which includes reducing or preventing the symptoms that result from cancer (e.g., metastatic cancer or relapsed cancer), reducing or preventing the occurrence of such symptoms (either quantitatively or qualitatively), reducing the severity of such symptoms or physiological effects thereof, and/or enhancing the recovery of the individual after experiencing cancer (e.g., metastatic cancer or relapsed cancer) symptoms.

Specifically, the therapies (e.g., one or more oligonucleotide) of the present invention, when administered to an individual, can treat or prevent one or more of the symptoms or conditions associated with cancer (e.g., metastatic cancer or relapsed cancer) and/or reduce or alleviate symptoms of or conditions associated with this disorder. As such, protecting an individual from the effects or symptoms resulting from cancer (e.g., metastatic cancer or relapsed cancer) includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such individual in those who have been treated with the methods of the present invention as compared to those that have not. For example, the at least one clinical or biological score, value, or measure used to evaluate such an individual is the capability of cells (e.g., cancer stem cells) taken from a primary tumor, a secondary tumor, a biopsy, or ascites fluid of an individual to form spheres in a sphere formation assay. Methods for purifying cells such as cancer stem cells from tumors or other biological samples are well known in the art such as in U.S. Pat. No. 8,614,095, the disclosure of which is incorporated by reference herein in its entirety. In an exemplary sphere formation assay, a tumor is surgically removed from a subject and minced with a scalpel into fragments of approximately 2 to 3 mm3. The fragments are washed with a buffer (e.g., PBS) and then incubated with buffer containing sodium hypochlorite. The tumor tissue fragments are washed with buffer and digested with PBS and digested with a medium containing one or more of collagenase I, collagenase IV, dispase, hyaluronidase and DNAase. The cell suspension is centrifuged and the pellet is suspended in buffer containing βFGF and EGF. The cells are washed to remove serum and suspended in medium supplemented with human EGF, human βFGF, B27 supplement without vitamin A, hydrocortisone, insulin, and N2 supplement. The cells are subsequently cultured in non-adherent plates. After 10 days in culture, spheres of 100 to 200 μm in diameter are obtained and counted. The spheres can be further expanded clonally, or injected into a subject to observe the capability of tumor formation. In some embodiments, an individual that has received an effective amount of one or more oligonucleotide (or compositions thereof) disclosed herein, alone or in combination with at least one therapy disclosed herein, has reduced sphere formation as compared to an individual not treated with the oligonucleotides of the present invention.

VI. Articles of Manufacture or Kits

In another aspect, an article of manufacture or kit is provided which comprises one or more oligonucleotide described herein. The article of manufacture or kit may further comprise instructions for use of the one or more oligonucleotide in the methods of the invention. Accordingly, in certain embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for suppressing metastasis of a cancer, preventing or treating relapse of a cancer, and/or treating metastatic cancer in an individual comprising administering to the individual an effective amount of the one or more oligonucleotide. In certain embodiments, the individual has been previously treated for cancer with a therapy (e.g., chemotherapy, radiation therapy, surgery, or combinations thereof). In some embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for treating a refractory cancer (e.g., a refractory HPV-associated cancer) in an individual comprising administering to the individual an effective amount of the one or more oligonucleotide.

The article of manufacture or kit may further comprise a container. Suitable containers include, for example, bottles, vials (e.g., dual chamber vials), syringes (e.g., single or dual chamber syringes), IV bags, and test tubes. The container may be formed from a variety of materials such as glass or plastic. The container holds the composition (e.g., pharmaceutical formulation).

The article of manufacture or kit may further comprise a label or package insert, which is on, or associated with the container and may indicate directions for reconstitution and/or use of the composition (e.g., pharmaceutical formulation). The label may further indicate that the formulation is useful or intended for intravenous, subcutaneous, or other modes of administration for suppressing metastasis of a cancer, preventing or treating relapse of a cancer, and/or treating metastatic cancer in an individual. In other embodiments, the label may further indicate that the formulation is useful or intended for intravenous, subcutaneous, or other modes of administration for treating a refractory cancer (e.g., a refractory HPV-associated cancer) in an individual. The container holding the formulation may be a single-use vial or a multi-use vial which allows for repeat administrations (e.g., from 2-6 administrations) of the reconstituted composition (e.g., pharmaceutical formulation). The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture of kit described herein optionally further comprises a container comprising a second therapeutic composition (e.g., an anti-cancer agent). For example, the article of manufacture or kit can comprise one or more oligonucleotide as a first composition (e.g., a first pharmaceutical composition) and an anti-cancer agent as a second composition (e.g., a second pharmaceutical composition). In some embodiments, the kit further comprises instructions for use of the one or more oligonucleotide in combination with the anti-cancer agent in the methods of the invention. An exemplary anti-cancer agents may be remicade, docetaxel celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda. CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and/or etoposide.

VII. Additional Exemplary Embodiments

The present application in some embodiments provides a method of treatment for a refractory cancer in an individual comprising administering to the individual an effective amount of one or more oligonucleotide complementary to an antisense non-coding chimeric mitochondrial RNA (ASnc-mtRNA) molecule or a sense non-coding chimeric mitochondrial RNA (SncmtRNA) molecule, wherein the oligonucleotide is able to hybridize with the chimeric mitochondrial RNA molecules to form a stable duplex.

In some embodiments according to (or as applied to) any of the embodiments above, the oligonucleotide is sufficiently complementary to a human non-coding chimeric mitochondrial RNA molecule comprising: a) an antisense 16S mitochondrial ribosomal RNA covalently linked at its 5' end to the 3' end of a polynucleotide with an inverted repeat sequence or b) a sense 16S mitochondrial ribosomal RNA covalently linked at its 5' end to the 3' end of a polynucleotide with an inverted repeat sequence.

In some embodiments according to (or as applied to) any of the embodiments above, the oligonucleotide is complementary to the ASncmtRNA molecule encoded by a nucleotide sequence selected from the group consisting of SEQ ID NO:4, SEQ ID NO:5, and SEQ ID NO:6.

In some embodiments according to (or as applied to) any of the embodiments above, the oligonucleotide is at least 85% complementary to the ASncmtRNA molecule encoded by a nucleotide sequence selected from the group consisting of SEQ ID NO:4, SEQ ID NO:5, and SEQ ID NO:6.

In some embodiments according to (or as applied to) any of the embodiments above, the one or more oligonucleotide comprises a nucleotide sequence selected from the group consisting of SEQ ID NOs:7-198.

In some embodiments according to (or as applied to) any of the embodiments above, the one or more oligonucleotide comprises a nucleic acid sequence selected from the group consisting of SEQ ID NOs:36, 197 and 198.

In some embodiments according to (or as applied to) any of the embodiments above, the oligonucleotide is administered in combination with at least one anti-cancer agent.

In some embodiments according to (or as applied to) any of the embodiments above, the oligonucleotide and the at least one anti-cancer agent is administered sequentially.

In some embodiments according to (or as applied to) any of the embodiments above, the oligonucleotide and the at least one anti-cancer agent is administered simultaneously.

In some embodiments according to (or as applied to) any of the embodiments above, the oligonucleotide is administered in combination with a radiation therapy.

In some embodiments according to (or as applied to) any of the embodiments above, the oligonucleotide is administered in combination with surgery.

In some embodiments according to (or as applied to) any of the embodiments above, the individual has been previously treated for cancer with a therapy comprising chemotherapy, radiation therapy, surgery, or combinations thereof.

In some embodiments according to (or as applied to) any of the embodiments above, the refractory cancer is a refractory HPV-associated cancer.

In some embodiments according to (or as applied to) any of the embodiments above, the refractory HPV-associated cancer is one or more selected from the group consisting of: cervical cancer, oralpharyngeal cancer, and head and neck cancer.

In some embodiments according to (or as applied to) any of the embodiments above, the refractory HPV-associated cancer is resistant to a chemotherapeutic agent.

In some embodiments according to (or as applied to) any of the embodiments above, the chemotherapeutic agent is one or more selected from the group consisting of: cisplatin, paclitaxel, actinomycin D, doxrubucin, etoposide, and 5-fluorouracil.

In some embodiments according to (or as applied to) any of the embodiments above, the refractory HPV-associated cancer is from an infection with one or more HPV strains selected from the group consisting of: HPV 16, HPV 18, HPV 31 and HPV 45.

In some embodiments according to (or as applied to) any of the embodiments above, the oligonucleotide reduces the number of cancer stem cells in the individual as compared to an individual not administered the oligonucleotide.

In some embodiments according to (or as applied to) any of the embodiments above, the oligonucleotide inhibits tumor growth and/or metastasis in the individual as compared to an individual not administered the oligonucleotide.

The invention will be more fully understood by reference to the following examples. The examples, which are intended to be purely exemplary of the invention, should not be construed as limiting the scope of the invention in any way. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Treatment of HCT-116 Colon Cancer Cells and Primary Cultures of Human Colon Cancer Cells with Antisense Oligonucleotides Complementary to Antisense Non-Coding Chimeric Mitochondrial RNA Abolished Sphere Formation In this study, the ability of cells, from both the HCT-116 colon cancer cell line and primary cultures of human colon cancer cells derived from patients, to form spheroid bodies following treatment with antisense oligonucleotides directed to antisense non-coding chimeric mitochondrial RNA (ASncmtRNA) was determined. The assay utilized measured the numbers of spheroid bodies, also referred to herein as spheres, based on the specific ability of cancer stem cells to form these spheroid bodies.

Materials and Methods
Experimental Scheme:

FIG. 1 demonstrates a general scheme of the experimental procedure and the assay utilized herein to measure the effect of antisense oligonucleotides targeted to ASncmtRNA on the number of spheres formed in colon cancer cells, based on the specific ability of cancer stem cells to form these spheroid bodies. Sphere formation was measured in HCT-116 colon cancer cells and primary cultures of human colon cancer cells derived from patients.

Primary Cultures of Human Cancer Cells:

Biopsies of colon cancer were received post-surgery and with corresponding informed consent of each patient. Pieces of tumors of about 500 mm3 were transferred to sterile tubes of 50 ml containing DMEM medium. High-Glucose, GlataMax™ (GIBCO), 10% FCS (Biological Industries), Fungizone® 1×, 2× antibiotic-antimycotic mix and gentamicin 25 µg/ml (Invitrogen). The biopsies were processed within 2 to 3 h post-surgery.

In order to disaggregate the tumor, a piece of colon tumor was minced with a scalpel into fragments of approximately 2 to 3 mm3. The fragments were washed twice with PBS and then incubated for 20 minutes with PBS containing 0.5% sodium hypochlorite. The fragments were washed three times with PBS and digested with RPMI medium (Invitrogen) containing 1 mg/ml collagenase 1, 2 mg/ml collagenase IV, 1 mg/ml dispase, 20 µg/ml hyaluronidase and 2000 U/ml DNAase. The mix was incubated at 37° C. for 60 min and with constant stirring. Next, the cell suspension was centrifuged at 200×g for 5 minutes and the pellet was suspended in PBS and centrifuged again a 200×g for 5 minutes. The pellet was resuspended in DMEM/F12 containing 1×N2 supplement, 10 ng/ml βFGF and 20 ng/ml EGF, for the formation of spheres.

Culture of HCT-116 Cells:

HCT-116 cells were cultured according to standard protocols. HCT-116 cells obtained from ATCC were grown in DMEM medium containing penicillin, gentamicin and fungizone, with 10% FCS, at 37° C. and with 5% CO2.

Selection of Tumor Cells by Sphere Formation and Adherence to Coated Plates:

Cells derived from colon cancer tumors or HCT-116 cultures were collected and washed to remove serum and suspended in serum-free DMEM/F12 supplemented with 100 IU/ml penicillin, 100 µg/ml streptomycin, 20 ng/ml human EGF, 20 ng/ml human βFGF, 2% B27 supplement without vitamin A, hydrocortisone, insulin (Lonza) and N2 supplement (Invitrogen, Carlsbad, Calif., USA). The cells were subsequently cultured in non-adherent plates (Corning Inc., Corning, N.Y., USA) at a density of about 5,000 cells/well or 1×105 cells in T25 flasks (Corning Inc. T25 3815). After 10 days in culture, spheres of 100 to 200 µm in diameter were obtained. The medium containing the spheres were filtered using a 70 µm nylon filter to eliminate single cells. The spheres were collected and dissociated with trypsin-EDTA and mechanically disrupted with a pipette. The cells were then centrifuged to remove the enzyme, washed once with DMEM medium containing 105 CFS and plated in adherent plates coated with collagen I (Gibco) and cultured at 37° C. and 5% CO2 as described before.

Cell Transfection and Antisense Oligonucleotides:

Antisense oligonucleotides (ASOs) used in this study were synthesized by IDT (Integrated DNA Technologies, USA), Invitrogen or Biosearch Inc. with 100% phosphorothioate (PS) internucleosidic linkages. For transfection, cells were seeded into 12-well plates (Nunc) at 50,000 cells/well. The next day, cells selected from colon cancer tumors or from HCT-116 cultures (see Selection of tumor cells by sphere formation and adherence to coated plates) were transfected with the antisense oligonucleotides (ASO 1107S: 5'-GTCCTAAACTACCAAACC-3' (SEQ ID NO:197) or ASO 1537S: 5'-CACCCACCCAAGAACAGG-3' (SEQ ID NO:36), depending on the cell type) or a control oligonucleotide (Control Oligo 154: 5'-AGGTGGAGTGGATTGGGG-3' (SEQ ID NO: 199)) at a final concentration of 100 to 200 nM (depending on the cell type) using Lipofectamine 2000 (Invitrogen) according to the manufacturer's directions. In addition, a subset of cells were left untreated or in the presence of only Lipofectamine 2000. Transfection was for 48 hours under normal culture conditions.

Sphere Formation Assay:

At 48 hours post transfection, the cells were harvested, counted and 5,000 to 6,000 cells were cultured in non-adherent 6-well plates (Corning Inc., Corning, N.Y., USA) as described before (described supra). After 10 days in culture, spheres of 100 to 200 µm in diameter were obtained and counted.

Results

Figure 2:
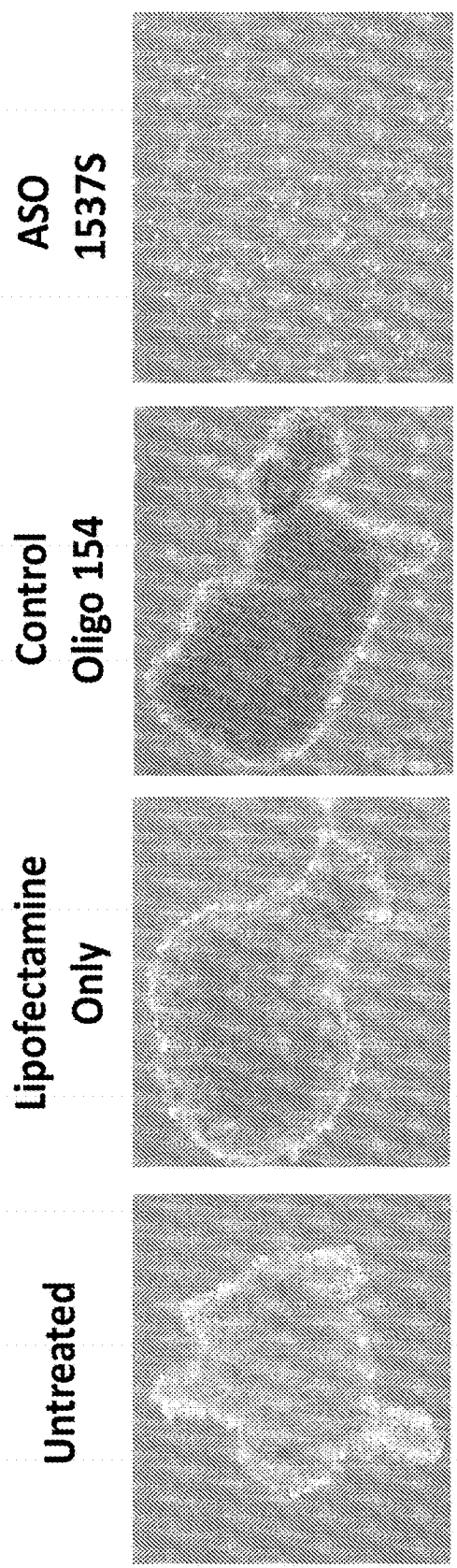
FIG. 2 depicts representative examples of spheres formed in primary colon tumor cancer cells following no treatment, treatment with only Lipofectamine, treatment with a control oligonucleotide (Control Oligo 154), or treatment with an antisense oligonucleotide (ASO) targeted to ASncmtRNA (ASO 1537S). Treatment with the ASO 1537S abolished the formation of spheres.

Sphere formation was unchanged in primary cultures of colon tumor cells following no treatment, treatment with only Lipofectamine, or treatment with Control Oligo 154. But sphere formation was abolished in these primary cells following treatment with ASO 1537S (FIG. 2).

Figure 3:
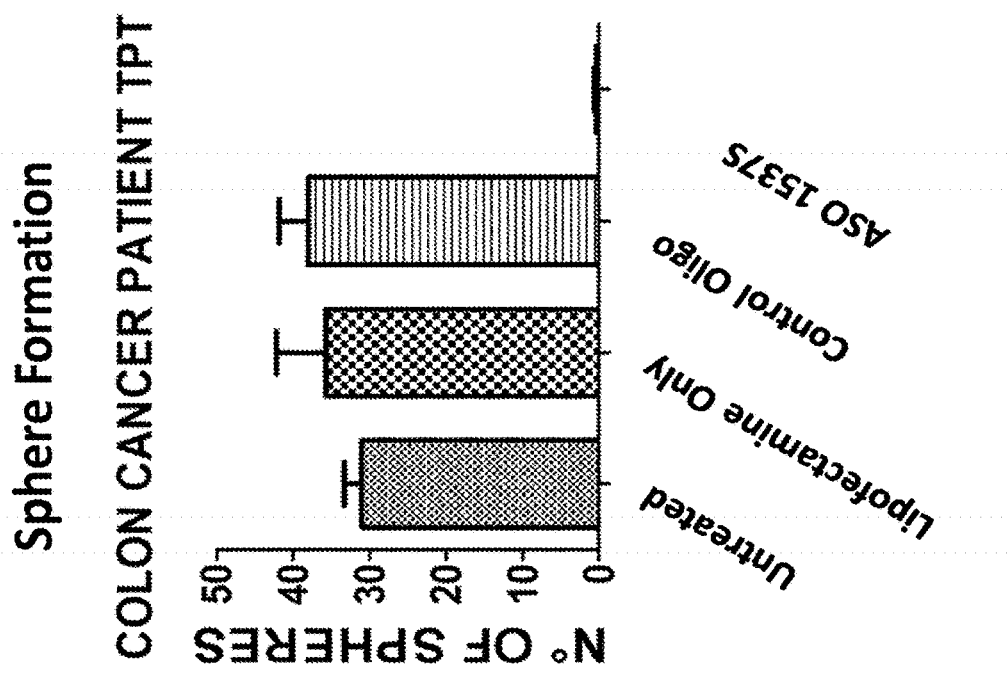
FIG. 3 depicts a quantification of the capacity of primary colon tumor cells to form spheres. Approximately 0.6% of the total number of cells seeded were able to form spheres. Cells transfected with ASO 1537S were unable to form spheres.

A primary culture of a colon tumor (patient TPT; 50,000 cells) was used to quantify sphere formation and evaluate the effect of transfection with ASO 1537S on the capacity of these cells to form spheres. The three groups of control cells (untreated, treated with Lipofectamine only, or treated with Control Oligo 154) formed spheres (30 to 37 spheres) equivalent to approximately 0.6% of the total number of cells seeded. Cells transfected with ASO 1537S were unable to form spheres (FIG. 3).

Figure 4:
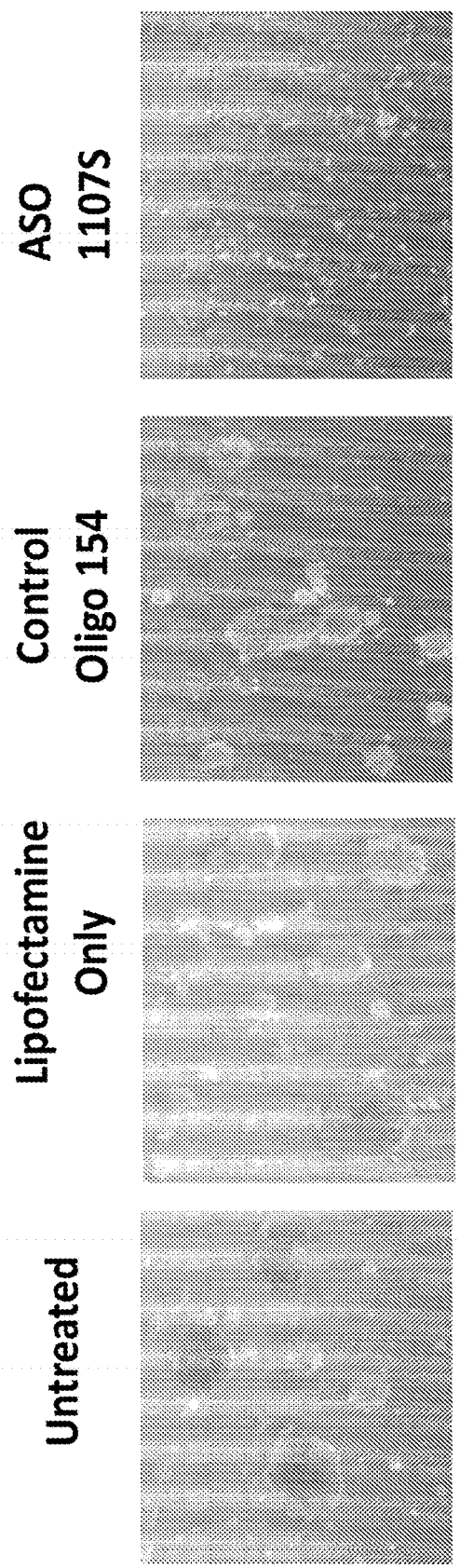
FIG. 4 depicts representative examples of spheres formed in cells from the HCT-116 colon cancer cell line following no treatment, treatment with only Lipofectamine, treatment with a control oligonucleotide (Control Oligo 154), or treatment with an antisense oligonucleotide targeted to ASncmtRNA (ASO 1107S). Treatment with ASO 1107S abolished the formation of spheres.

Sphere formation was unchanged in cells from the HCT-116 colon tumor cell line following no treatment, treatment with only Lipofectamine, or treatment with Control Oligo 154. However, sphere formation was abolished in these cells following treatment with ASO 1107S (FIG. 4).

Figure 5:
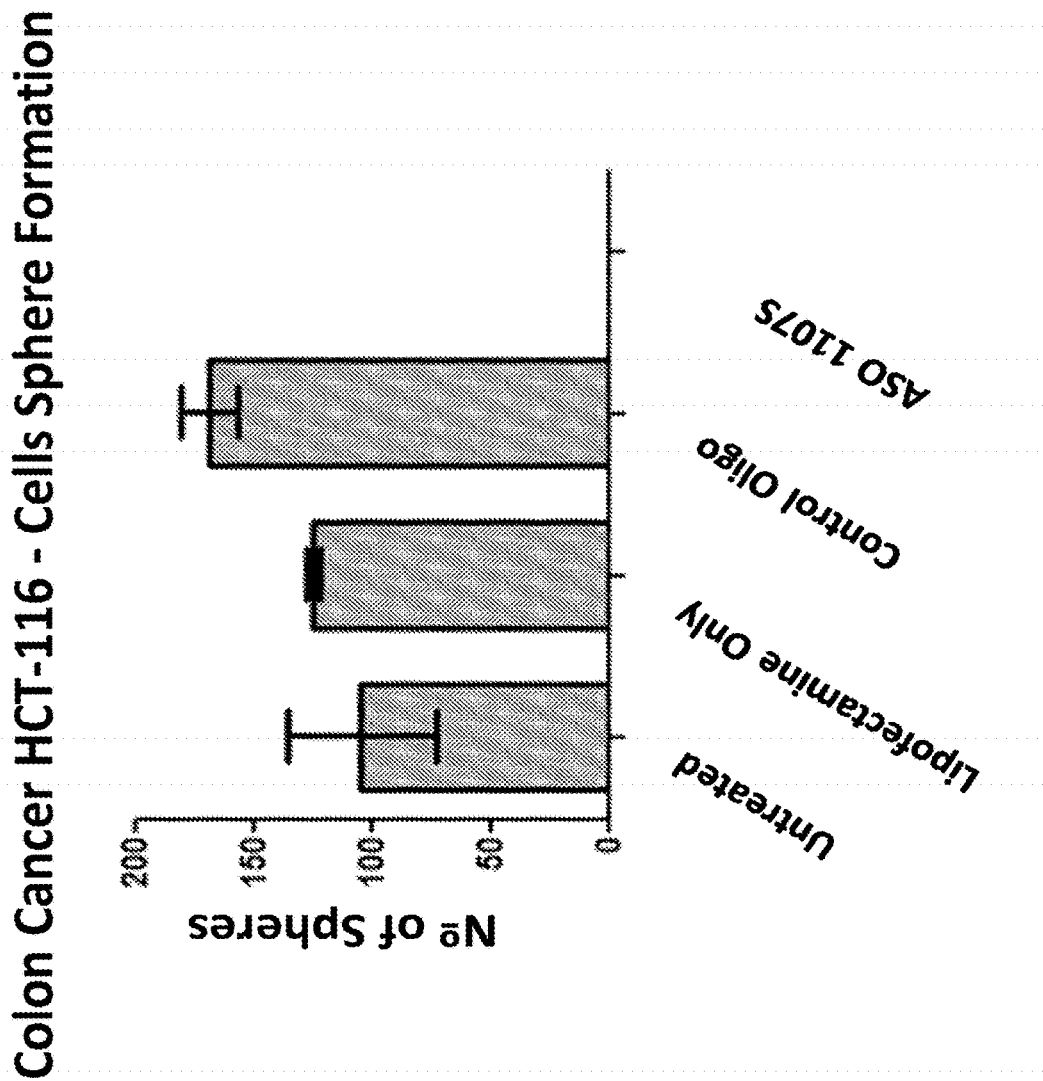
FIG. 5 depicts a quantification of the capacity of HCT-116 colon cancer cells to form spheres. Approximately 0.3% of the total number of cells seeded were able to form spheres. Cells transfected with ASO 1107S were unable to form spheres.

The colon tumor cell line HCT-116 was used to quantify sphere formation and evaluate the effect of transfection with ASO 1107S on sphere formation. The three groups of control cells (untreated, treated with Lipofectamine only, or treated with Control Oligo 154) formed spheres (100 to 160 spheres), equivalent to 0.3% of the total amount of cells seeded (in this representative example 50,000 cells in 125 flasks). However, cells transfected with ASO 1107S were not able to form spheres (FIG. 5).

Taken together, these results show that groups left untreated, treated with only Lipofectamine, or transfected with a control oligonucleotide retained the ability to form spheres. In contrast, primary colon tumor cells or HCT-116 colon cancer cells transfected with antisense oligonucleotides lost their ability to form spheres. These results indicate that the antisense oligonucleotides were able to kill cancer stem cells as indicated by the lack of sphere formation upon treatment. Furthermore, these results also indicate that only a fraction of all cells seeded were able to form spheres.

Example 2: Treatment of a Cervical Cancer Cell Line and Primary Cultures of Human Uterine Cervical Cancer Cells with Antisense Oligonucleotides Complementary to Antisense Non-Coding Chimeric Mitochondrial RNA Abolished Sphere Formation The ability of cervical cells from the SiHa cervical cancer cell line (transformed with Human Papillomavirus 16 or HPV 16) and from primary cultures of human uterine cervical cancer cells derived from patients to form spheroid bodies following treatment with antisense oligonucleotides directed to antisense non-coding chimeric mitochondrial RNA (ASncmtRNA) was determined. The assay utilized measured the numbers of spheroid bodies, also referred to herein as spheres, which are formed by cancer stem cells.

Figure 6:
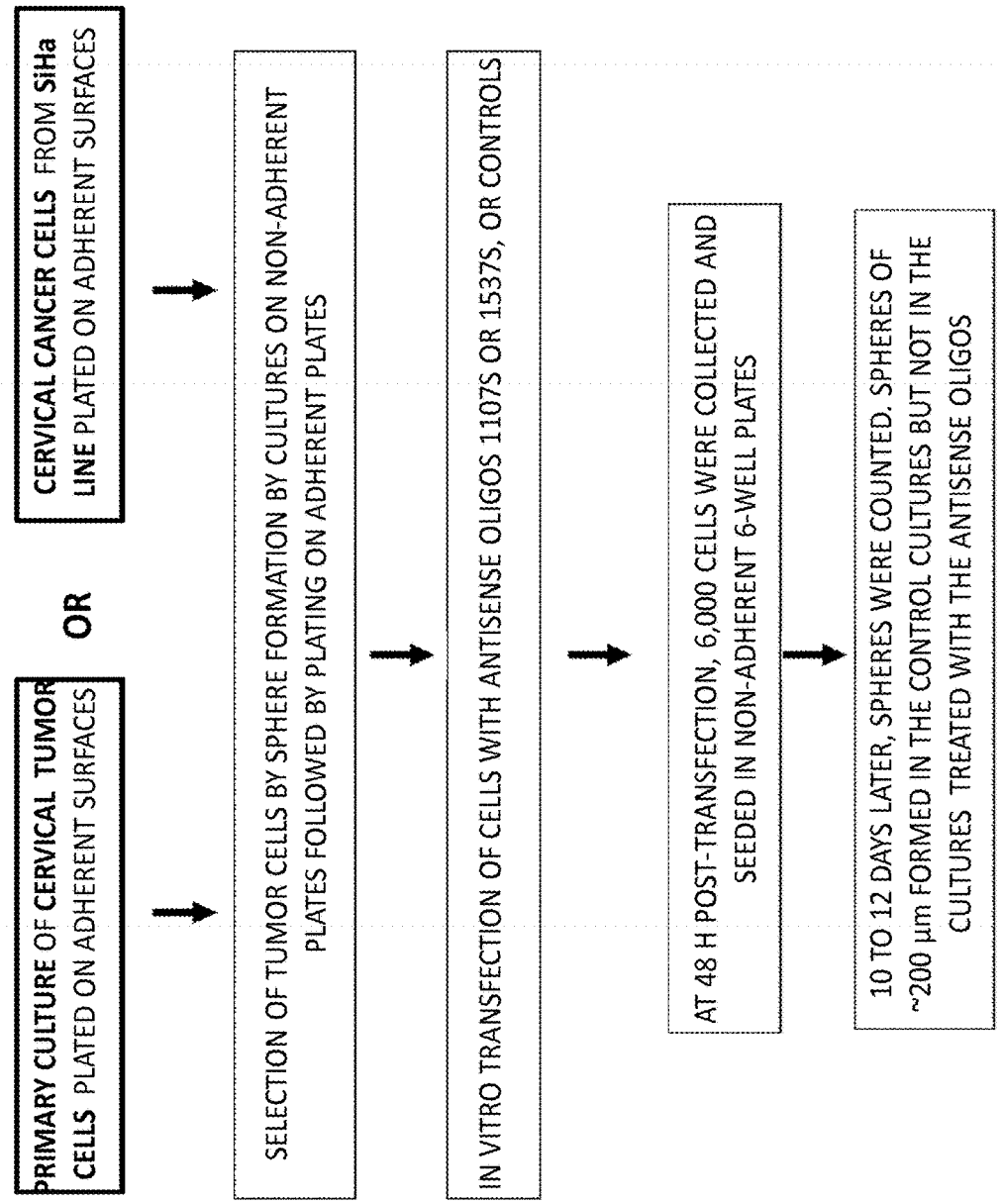
FIG. 6 depicts a general scheme of the experimental procedure and the assay utilized herein to measure the effect of antisense oligonucleotides targeted to ASncmtRNA on the number of spheres formed by the cervical cancer SiHa cell line and primary culture cells of cervical tumors. The assay is based on the ability of cancer stem cells to form spheres, also referred to herein as spheroid bodies.

Materials and Methods
Experimental Scheme:

The experimental procedure and assay utilized herein measured the effect of antisense oligonucleotides that were targeted to ASncmtRNA on the number of spheres formed by cervical cancer cells (FIG. 6). Sphere formation was measured in the SiHa cervical cancer cell line and primary cultures of human cervical cancer cells derived from patients (CerCa). CerCa 1, CerCa 2 and CerCa 3 (transformed with Human Papillomavirus 45) were obtained from patient biopsies.

Culture of SiHa Cells:

SiHa cells were grown in DMEM, "High Glucose", GlutaMAX™, containing penicillin, gentamicin and fungizone, with 10% FCS at 37° C. and with 5% C02.

Primary Cultures of Human Cancer Cells:

Biopsies of uterine cervical cancer were received post-surgery and with the corresponding informed consent of each patient. Pieces of tumors of about 500 mm3 were transferred to 50 ml, sterile tubes containing DMEM medium. High-Glucose, GlataMax™ (GIBCO), 10% FCS (Biological Industries). Fungizone® 1×, 2× antibiotic-antimycotic mix and gentamicin 25 µg/ml (Invitrogen). The biopsies were processed within 2 to 3 hours post-surgery.

In order to disaggregate the tumor, the tissue sample was placed on a 10 cm Petri dish with 10 ml of sterile PBS (Gibco) and sliced with a scalpel into small pieces (1-3 mm3). The pieces were transferred to 6 cm dishes together with 2 ml of medium containing 0.5% Colagenase I, 0.5% Colagenase II, 0.5% Colagenase IV (GIBCO), 0.5% hialorunidase (AppliChem), 0.1% Dispase (GIBCO), 0.05% DNase (AppliChem), 0.1% BSA (Rockland), antibiotic-antimycotic 2× mix (GIBCO) and Fungizone® 2× (GIBCO). The fragments were incubated at 37° C. for 30 min and the cell suspension was centrifuged at 300×g for 5 minutes. The pellet was suspended in 5 ml MEGM™ medium containing 20 ng/ml of hEGF 20, hydrocortisone, insulin. GA-1000 (Lonza), 0.5×B-27 without vitamin A (Invitrogen), 20 ng/ml of FGFb (Invitrogen) and 5% CFB. The cells were cultured in a T25 flask coated with collagen (BD Bioscience) at 37° C. and with 5% CO2. The medium was changed every 48 hours.

Selection of Tumor Cells by Sphere Formation and Adherence to Coated Plates:

About 1×105 cells resuspended in MEGM™ medium supplemented with 20 ng/ml of hEGF, hydrocortisone, insulin, GA-1000 (Lonza), 0.5×B-27 without vitamin A (Invitrogen), 20 ng/ml of FGFb (Invitrogen) without CFS were seeded on ultra-low adherence plates (Corning). Ten days later, the spheres were counted under phase microscopy, collected and filtered using a nylon mesh of 70 µm to discard single cells. The spheres were recovered from the filter and seeded on 6-well plates (Corning) previously coated with collagen type I (Gibco) and cultured as described above. Three human primary cultures of cervical tumors, CerCa 1, CerCa 2 and CerCa 3, were isolated.

Human Papillomavirus (HPV) Genotyping:

The different primary cultures were analyzed with the PGMY09/11 Linear Array (Roche). The presence of HPV 16 was detected in CerCa 1 and CerCa 2 primary cell cultures while HPV 45 was detected in the CerCa 3 primary cell culture.

Cell Transfection and Antisense Oligonucleotides:

Antisense oligonucleotides (ASOs) used in this study were synthesized by IDT (Integrated DNA Technologies, USA), Invitrogen or Biosearch Inc. with 100% phosphorothioate (PS) internucleosidic linkages. For transfection, cells were seeded into 12-well plates (Nunc) at 5000 cells/well. The next day, cells selected from cervical cancer tumors or from SiHa cells (See Selection of Tumor Cells by Sphere Formation and Adherence to Coated Plates) were transfected with an antisense oligonucleotide (ASO 1537S: 5'-CAC-CCACCCAAGAACAGG-3' (SEQ ID NO:36), depending of the cell type) or a control oligonucleotide 154 (ASO-C: 5'-AGGTGGAGTGGATTGGGG-3'(SEQ ID NO: 199)) at a final concentration of 100 nM (SiHa cells) or 200 nM (CerCa cells) using Lipofectamine 2000 (Invitrogen) according to the manufacturer's directions. In addition, a subset of cells were left untreated (NT), transfected in the presence of Lipofectamine 2000 (LIPO) only, or incubated with 45 uM cisplatin (CISP). Transfection was conducted for 72 hours under normal culture conditions.

Sphere Formation Assay:

At 72 hours post transfection, the cells were harvested, counted and 5,000 to 6,000 cells were cultured in non-adherent 6-well plates (Corning Inc., Corning, N.Y., USA) as described above. After 10 days in culture, spheres of 100 to 200 µm in diameter were obtained and counted.

Results

Figure 7:
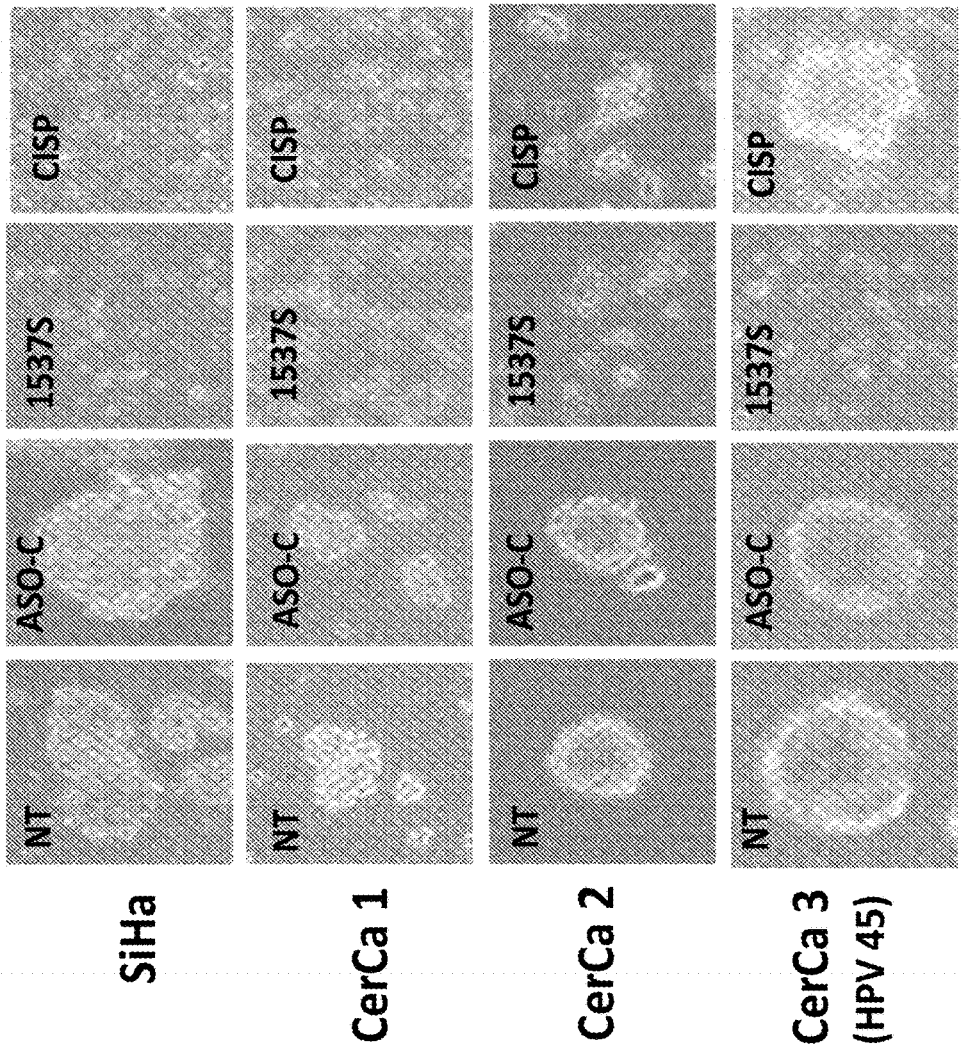
FIG. 7 depicts representative examples of spheres formed by the cervical cancer SiHa cell line and primary culture cells of cervical tumors following no treatment (NT), treatment with a control oligonucleotide (Control Oligo 154: ASO-C), or treatment with an antisense oligonucleotide targeted to ASncmtRNA (ASO 1537S) or treatment with 45 μM cisplatin (CISP). Treatment with the ASO 1537S abolished the formation of spheres. The CerCa 3 cells obtained from primary culture, which is infected with HPV 45, is resistant to treatment with cisplatin as compared to two other cells obtained from primary culture, which are infected with HPV 16.
Figure 8:
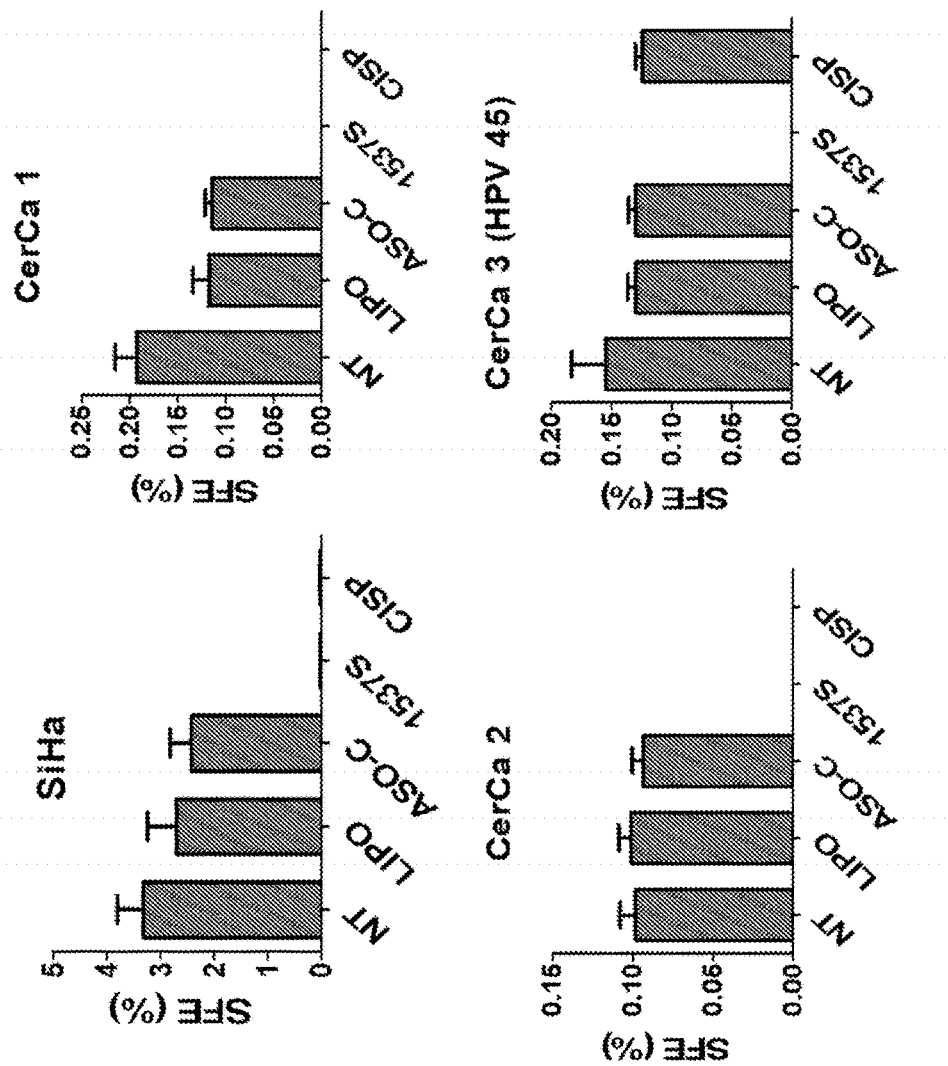
FIG. 8 depicts quantification of sphere formation by the SiHa cell cell line and primary cervical tumor cells (CerCa 1, CerCa 2 and CerCa 3) with or without treatment. Cells transfected with ASO 1537S were unable to form spheres. The CerCa 3 primary culture infected with HPV 45 was resistant to treatment with cisplatin but not to treatment with ASO 1537S.

Sphere formation was unchanged in primary cultures of cervical tumor cells following no treatment (NT), treatment with only Lipofectamine (LIPO), or treatment with control oligonucleotide 154 (ASO-C). In contrast, sphere formation was abolished in SiHa, CerCa 1, CerCa 2 and CerCa 3 primary cultures following treatment with ASO 1537S (FIG. 7 and FIG. 8). Sphere formation of SiHa, CerCa 1 and CerCa 2 cells (all infected with HPV 16) was also abolished when cells were treated with the drug cisplatin (CISP) (45 µM) (FIG. 7 and FIG. 8) while no effect was observed in CerCa 3 cells (infected with HPV 45) treated with cisplatin.

Taken together, these results show that cervical cancer primary cultures (CerCa 1, CerCa 2 and CerCa 3 cells) and the cell line SiHa left untreated, treated with only Lipofectamine, or transfected with a control oligonucleotide retained the ability to form spheres. In contrast, primary cervical tumor cells or SiHa cells transfected with antisense oligonucleotides targeted to the antisense non-coding chimeric mitochondrial RNA (ASncmtRNA) molecules or sense non-coding chimeric mitochondrial RNA (SncmtRNA) molecule, lost their ability to form spheres whether HPV 16 or HPV 45 positive. These results indicate that the antisense oligonucleotides were able to kill cervical cancer stem cells as indicated by the lack of sphere formation upon treatment. Moreover, treatment with the anti-cancer drug cisplatin abolished sphere formation of SiHa, CerCa 1 and CerCa 2 cells (all HPV 16 positive) but not CerCa 3 that is infected with HPV 45 (FIG. 7 and FIG. 8). Therefore, these results indicate that the antisense oligonucleotides are able to kill cervical cancer stem (CerCa 3 cells) resistant to cisplatin treatment. See Tjalme et al., *Am. J. Clin. Pathol.*, 137:161, 2012; de Sanjosé et al., *Eur J Cancer.*, 49(16): 3450, 2013; Tjalma et al., *Int J Cancer.*, 132(4):854, 2013.

Example 3: Treatment of Mice with Antisense Oligonucleotides Complementary to the Antisense Non-Coding Chimeric Mitochondrial RNA Following Surgery to Remove Intradermal Melanoma Tumors Prevented Relapse of Tumor Growth and Metastasis in the Lungs and Liver One common clinical protocol for melanoma includes surgical resection follow by systemic administration of drugs. Similar protocols are used in the practice of other tumors. In the melanoma model presented in this representative example, B16F10 melanoma cells (100,000 cells in 200 µl of saline) were injected subcutaneously on the back of C57BL/6 mice. About 11 to 12 days post-cell injection, tumors between 700 to 1.000 mm3 developed (a 1,000 mm3 tumor in mice is considered equivalent to a 3,000 cc3 tumor in humans). At this time, mice were randomly divided in two groups (Control Oligo ASO 154 and ASO 1560S (SEQ ID NO: 198)) with similar tumor volume. Tumors were surgically resected under anesthesia and the wound washed once with 250 µl containing 100 µg of ASO 1560S or ASO 154. After surgical suture, a bolus of 200 µl saline containing 100 µg of ASO 154 or ASO 1560S was applied into the cavity left by the tumor. Three days post-surgery, mice received on alternative days, 3 intravenous (FIG. 9; 1st, 3rd, 5th arrows on timeline) or 3 intraperitoneal (FIG. 9; 2nd, 4th, 6th arrows on timeline) injections of 250 µl saline containing 100 µg of either ASO 1560S or ASO 154. Tumor growth was measured twice a week with a caliper.

Figure 9:
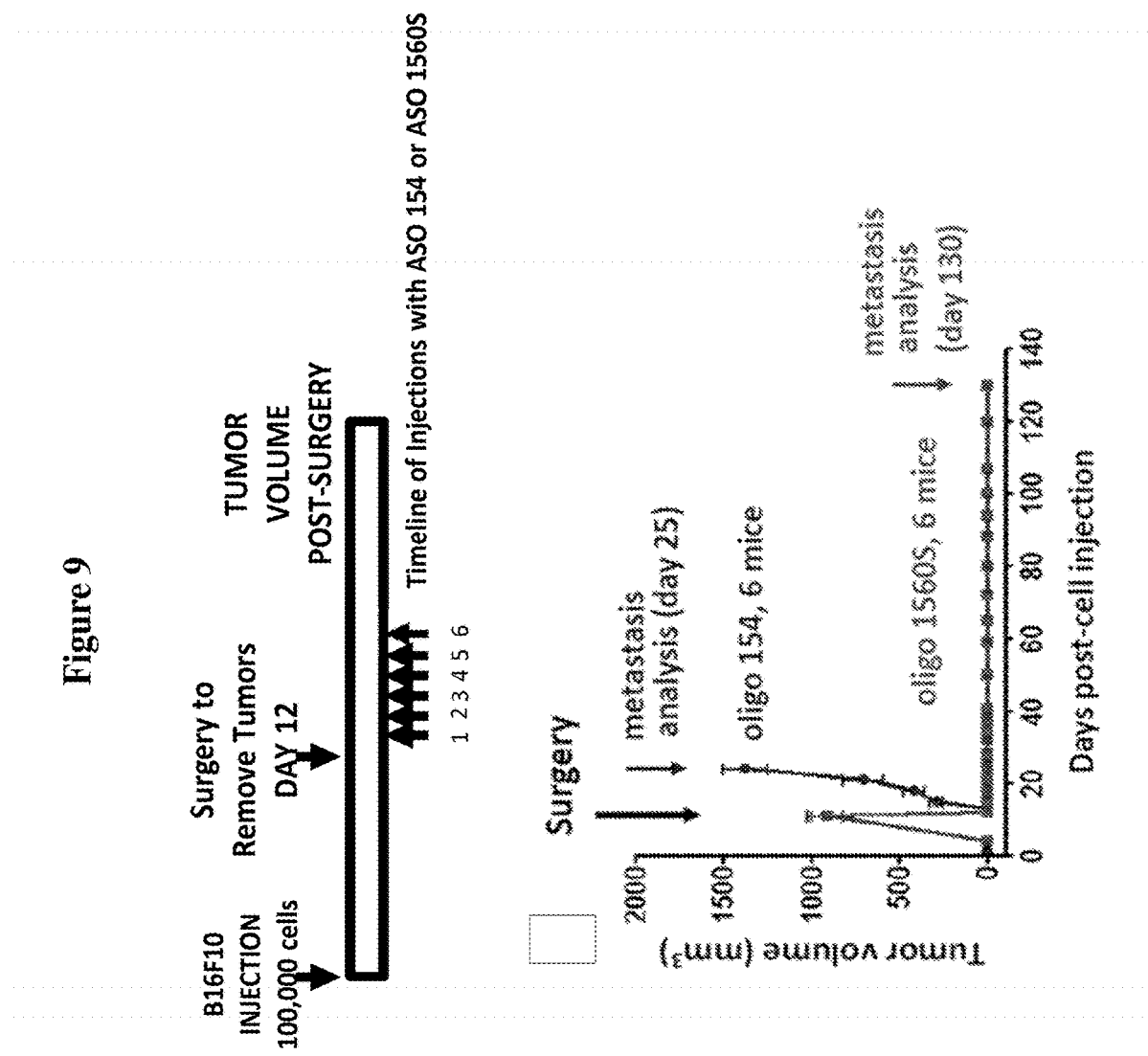
FIG. 9 depicts the absence of tumor relapse and the absence of metastatic nodules in the lungs and liver of mice treated with ASO 1560S (squares) but not Control Oligo 154 (circles) following the surgical removal of intradermal melanoma tumors.

Relapse of tumor growth in mice treated with ASO 154 was observed about 3 days post-surgery and tumor volume of about 1,500 mm3 was reached on about the 25th day post-cell injection (FIG. 9). These mice were euthanized under anesthesia, and the tumor and other organs were fixed and saved for further studies. No relapse was observed in mice treated with ASO 1560S targeted to the mouse ASncmtRNAs. At 130 days post-cell injection, mice appeared healthy without the presence of detectable tumors and were euthanized to collect organs. Livers and lungs were analyzed for the presence of metastatic nodules.

Control mice (treated with Control Oligo ASO 154) showed the presence of cancer relapse and metastatic black nodules in the lung and liver. In contrast, the lungs and livers of the mice treated with ASO 1560S lacked the presence of metastatic nodules demonstrating that ASO 1560S prevented or suppressed cancer relapse (FIG. 10).

Figure 11:
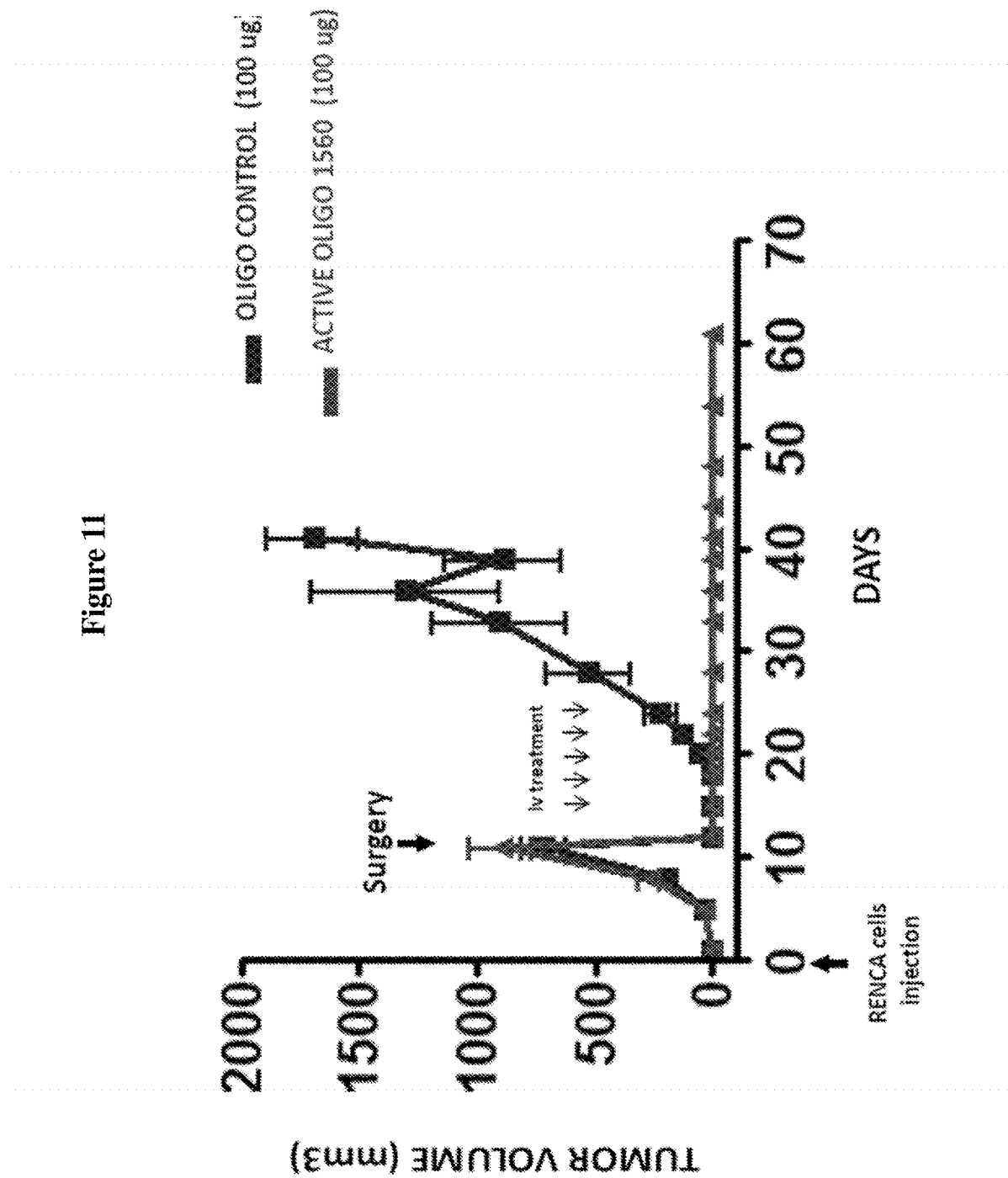
FIG. 11 depicts the absence of tumor relapse and complete survival of mice treated with ASO 1560S (triangles) but not Control ASO 154 (squares) following surgical removal of intradermal kidney carcinoma tumors.

Example 4: Intravenous Treatment of Mice with Antisense Oligonucleotides Complementary to the Antisense Non-Coding Chimeric Mitochondrial RNA Following Surgery to Remove Intradermal Kidney Tumors Resulted in Absence of Tumor Relapse and Complete Survival 100,000 RENCA cells (ATCC® CRL-2947™ *Mus musculus* kidney renal adenocarcina) were injected subcutaneously at day 0. At day 12, tumors of an average size of 800 mm3 were removed and the site of the tumor was washed with 100 µg of Control Oligo ASO 154 (4 animals) or ASO1560S (5 animals) in 200 µl, both formulated in liposomes. The animals were sutured and intravenously injected at the site of the removed tumor with 100 µg of ASO 154 (FIG. 11, squares) or ASO 1560S (FIG. 11, triangles), both formulated in liposomes, in 250 µl. No further treatment was given. At day 40, (30 days post-surgery), all the control animals had died with tumors of an average size of 1,200 mm3 and extensive metastasis, while all animals treated with ASO 1560S had no tumors and were still alive at day 61 (FIG. 11).

Figure 12:
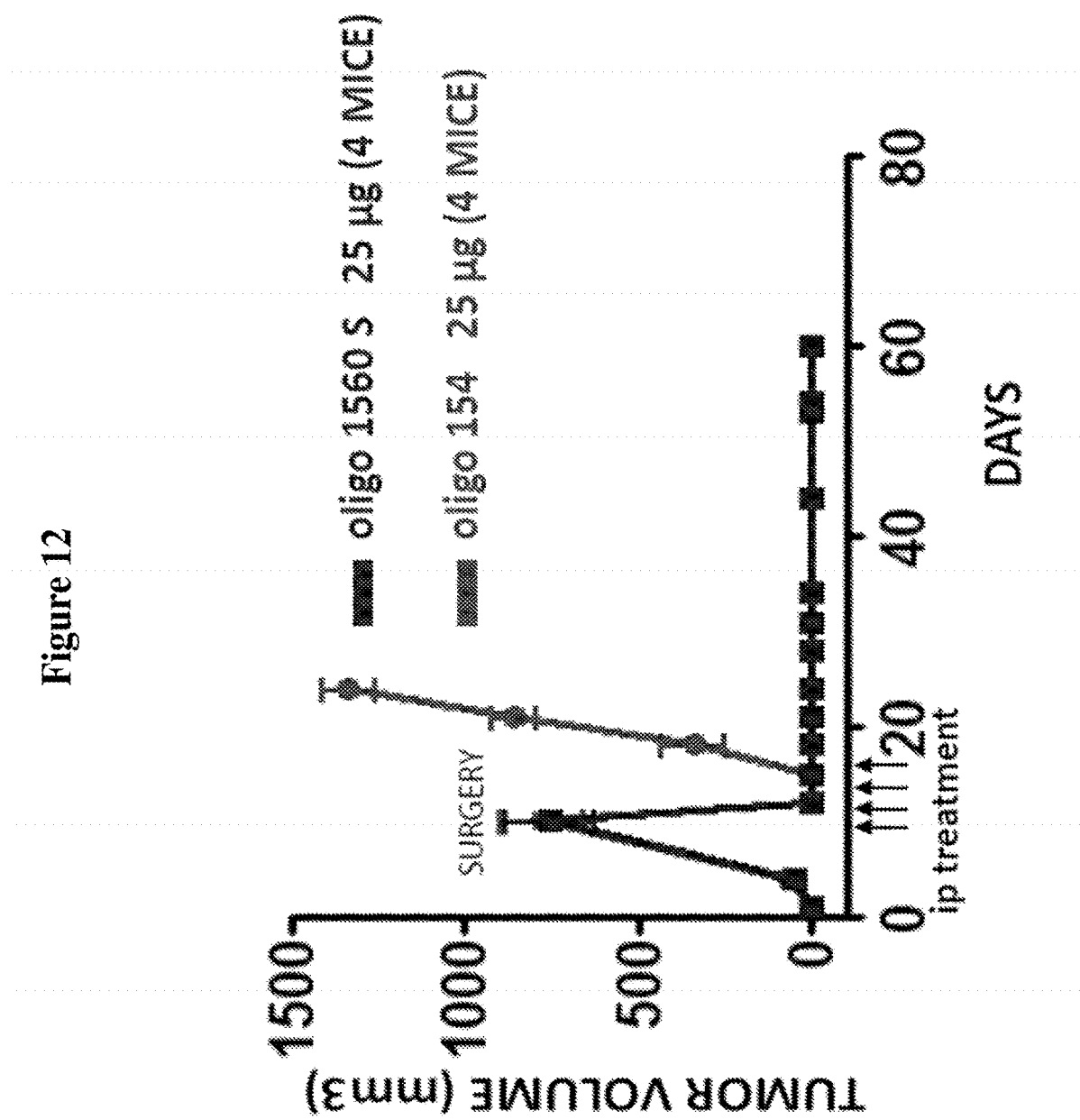
FIG. 12 depicts the absence of relapse in and survival of mice treated with ASO 1560S (squares) but not Control ASO 154 (circles) following surgical removal of intradermal kidney carcinoma tumors.

Example 5: Intraperitoneal Treatment of Mice with Antisense Oligonucleotides Complementary to the Antisense Non-Coding Chimeric Mitochondrial RNA Following Surgery to Remove Intradermal Kidney Tumors Resulted in Absence of Tumor Relapse and Complete Survival 100,000 RENCA cells (ATCC® CRL-2947™ *Mus musculus* kidney renal adenocarcina) were injected subcutaneously on day 0 in 8 mice. On day 11, tumors had an average size of 800 mm3. Tumors of all animals were removed by surgery and divided in 2 groups. The wound of the control group was washed once with Control Oligo ASO 154 before suturing and the wound of the treated group was washed with ASO 1560S before suturing. Post-suture, a bolus of 250 µl was intraperiotoneally injected in the place of where tumor had grown: the control group was injected with ASO 154 and the treated group with ASO 1560S. On days 13, 15, 17 and 19, intraperitoneal injections of 25 µg ASO 154 (FIG. 12, circles) or 25 µg ASO 1560S (FIG. 12, squares) formulated in liposomes were injected in a volume of 250 µl. On days 14, 16 and 18, the mice were injected intravenously with the same protocol. On day 22, all control animals had tumors larger than 1,200 mm3 and were sacrificed. On day 60, all animals treated with ASO 1560S had no tumors and were still alive (FIG. 12).

Example 6: Treatment of Mice with Antisense Oligonucleotides Complementary to the Antisense Non-Coding Chimeric Mitochondrial RNA Following Surgery to Remove Intradermal Melanoma Tumors Resulted in Absence of Tumor Relapse and Complete Survival B16F10 melanoma cells (100.000 cells in 200 µl of RPMI medium) were injected into mice subcutaneously on day 0. On day 11, surgery was carried out to remove tumors. The tumor volumes varied from approximately 800 to 1200 mm3. The wound was washed once. Post-suture one bolus of 250 µl of oligo in liposomes was injected in the tumor site. On days 13, 15, 17, 19 and 21, a dose of 25 µg control ASO 154 naked (FIG. 13, squares), 25 µg of control ASO 154 in liposomes (FIG. 13, circles), or 50 µg of ASO 154 in liposomes (FIG. 13, triangles), each in a volume of 250 µl, was intraperitoneally injected in the mice. Other groups of mice (6 mice per group) were injected in a similar manner as described above with 50 µg of ASO 1560 naked, 25 µg of ASO 1560S in liposomes or 50 µg of ASO 1560S in liposomes (FIG. 13, diamonds).

Figure 13:
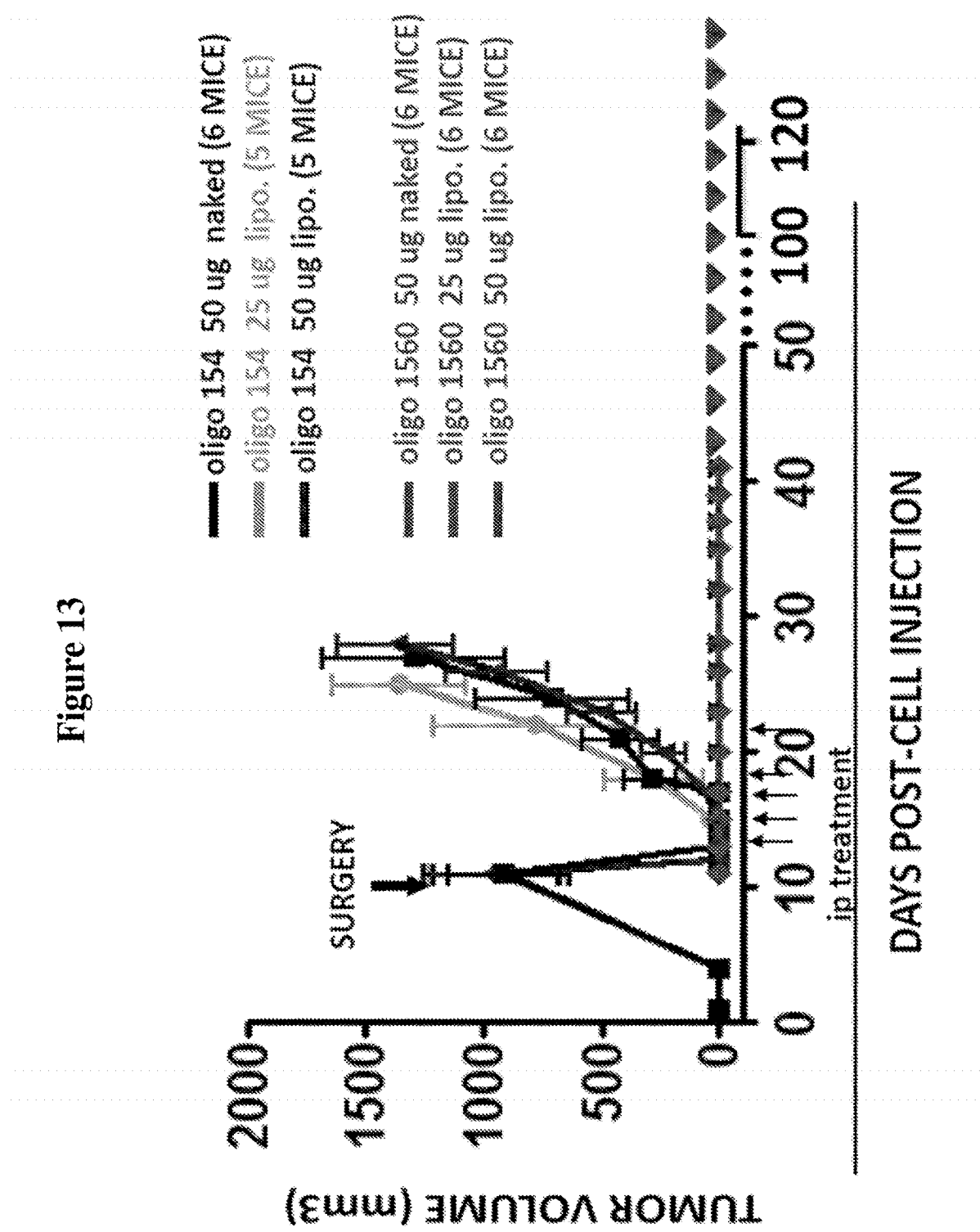
FIG. 13 depicts the absence of tumor relapse and complete survival of mice treated with ASO 1560S but not Control ASO 154 following surgical removal of intradermal melanoma carcinoma tumors.

Compared to mice treated with a control oligonucleotide, post-surgery treatment with 25 and 50 µg intraperitoneal injections of ASO 1560S resulted in the absence of the intradermal melanoma tumor relapse and complete survival (FIG. 13).

Figure 14:
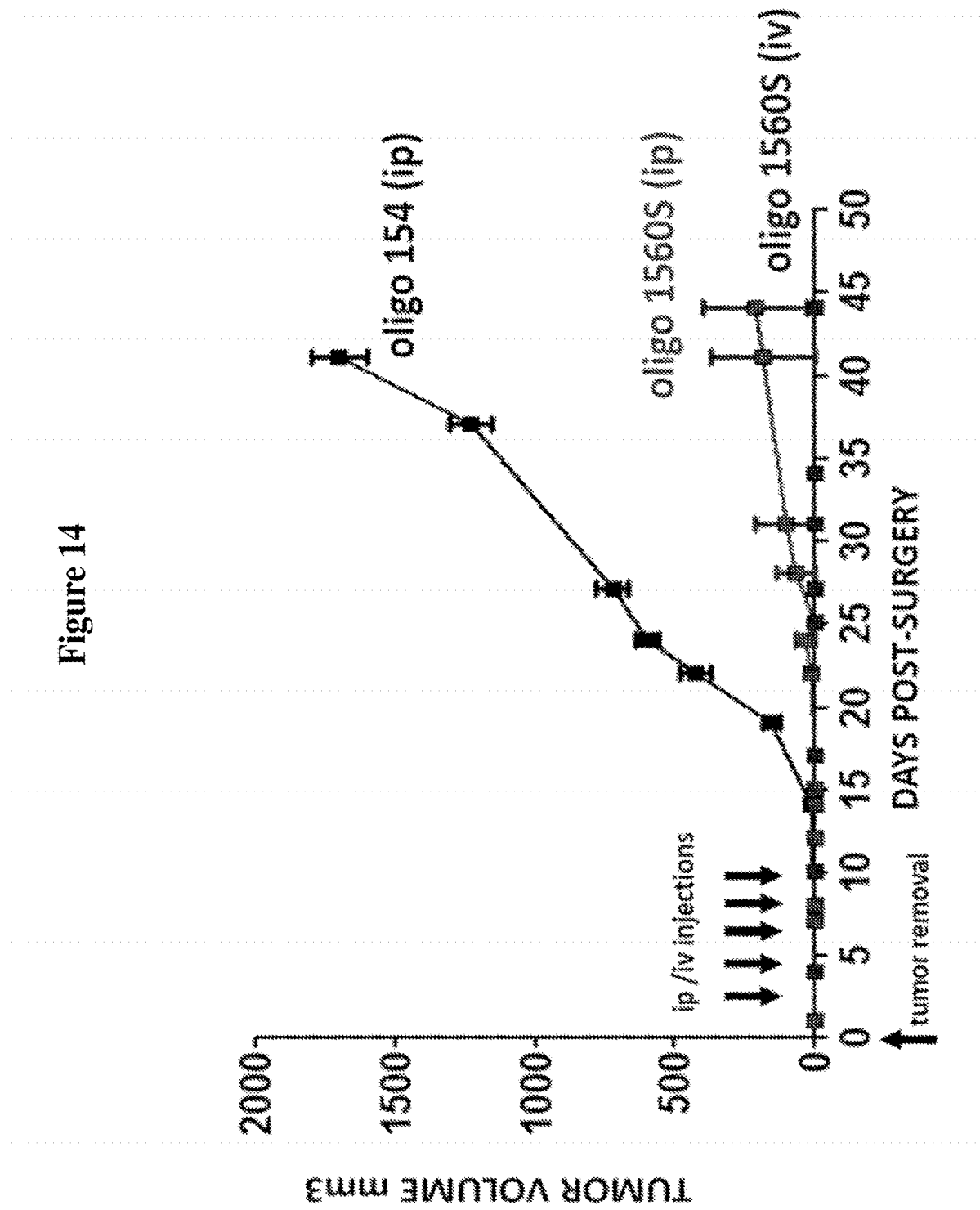
FIG. 14 depicts the absence of tumors and complete survival of mice treated with ASO 1560S but not Control ASO 154 following surgical removal of subcutaneous bladder carcinoma tumors. ip indicates intraperitoneal administration and iv indicates intravenous administration.

Example 7: Intraperitoneal or Intravenous Treatment of Mice with Antisense Oligonucleotides Complementary to the Antisense Non-Coding Chimeric Mitochondrial RNA Following Surgery to Remove Subcutaneous Bladder Carcinoma Tumors Resulted in Absence of Tumor and Complete Survival Twelve mice were injected subcutaneously with a 100,000 MB49 cells (mouse bladder cancer cells). After 15 days mice had tumors of an average diameter of 800 mm3. Tumors were surgically removed (day 0) and a bolus of 200 µl containing 100 µg of ASO 154 (control) or ASO 1560S (active drug) was injected at the site of the surgery. Three days post-surgery mice were divided in 2 groups and treated intraperitoneally or intravenously with 100 µl injections containing ASO 154 (control group) or ASO 1560S (treated group) as indicated in FIG. 14. Only one mouse treated intraperitoneally with ASO 1560S developed a tumor. All the mice treated intravenously with ASO 1560S remained without tumors and experienced full survival. Control animals treated with Control Oligo ASO 154 were sacrificed at day 41 (FIG. 14).

Example 8: Treatment of Rag −/− Mice with Antisense Oligonucleotides Complementary to the Antisense Non-Coding Chimeric Mitochondrial RNA Following Tumor Removal of a Human Melanoma Resulted in Significant Elimination of Tumor Relapse and a Large Increase in Survival Rag −/− mice were injected with 5 million human A375 melanoma cells. Approximately at 34 days post cell-injection, all mice developed tumors of about 700 mm3. Mice were subjected to tumor removal surgery and divided randomly in two groups.

Group 1 (control): the wound was washed with 50 µg of Control Oligo 154 (6 mice in group) in a volume of 200 µl. Group 2 (therapy): the wound was washed with 50 µg of ASO 1537S (8 mice in group) (Sequence of the oligonucleotide provided in Example 1) in 200 µl. After suturing, a bolus of 250 µl containing 50 µg of Control Oligo 154 (6 control mice) or 250 µl containing 50 µg of ASO Oligo 1537S was applied (8 therapy mice). Two days later mice received 6 injections with Control Oligo 154 or ASO Oligo 1537S every other day. The first injection was intraperitoneal and the second injection was in the tail vein.

Figure 15:
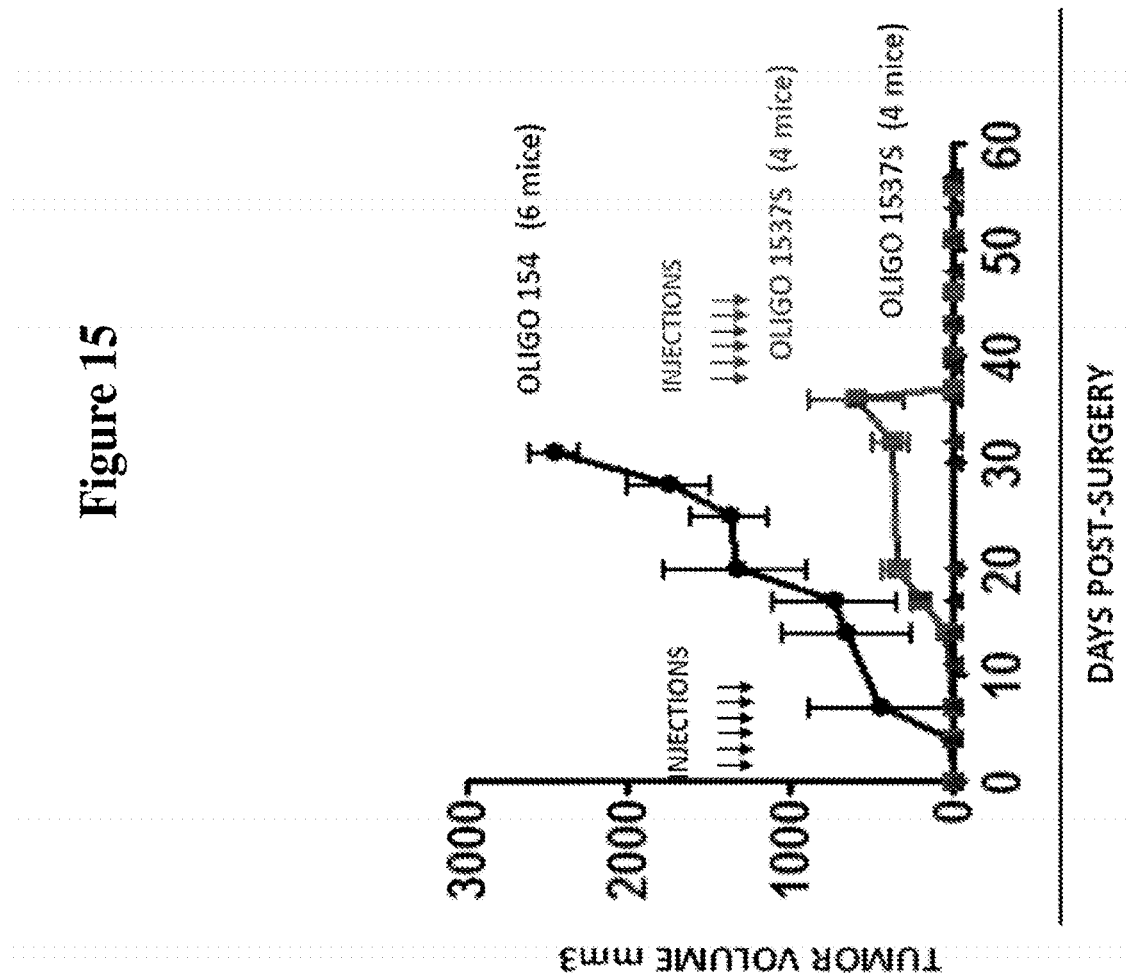
FIG. 15 depicts the reduction in tumors and increase in survival of Rag −/− mice treated with ASO 1537S but not Control ASO 154 following the removal of a human A375 melanoma tumor.

On day 30 after surgery, the 6 mice treated with Control Oligo 154 had tumors on the order of 2000 mm3 and were sacrificed (FIG. 15, circles). On day 57 after surgery, 4 out of the 8 mice receiving ASO Oligo 1537S were without tumors (FIG. 15, triangles). On day 17 post surgery, 4 out of the 8 mice receiving ASO Oligo 1537S began to show small tumors that grew slowly which at day 36 reached a size of about 500 mm3 (FIG. 15, squares). These mice were again subjected to surgery to remove the tumors, and subsequently 2 mice died. The other 2 mice were subjected to the same therapeutic protocol (alternating 3 injections intraperitoneal and 3 injections intravenous) with 50 µg of ASO Oligo 1537S in 250 µl (FIG. 15).

SEQUENCES

<210> SEQ ID NO 1
<211> LENGTH: 2374
<212> TYPE: DNA
<213> ORGANISM: Homo sapiens
<400> SEQUENCE: 1

```
  60    tctaatactg gtgatgctag aggtgatgtt tttggtaaac aggcggggta agatttgccg
 120    agttcctttt acttttttta acctttcctt atgagcatgc ctgtgttggg ttgacagtga
 180    gggtaataat gacttgttgg ttgattgtag atattgggct gttaattgtc agttcagtgt
 240    tttaatctga cgcaggctta tgcggaggag aatgttttca tgttacttat actaacatta
 300    gttcttctat agggtgatag attggtccaa ttgggtgtga ggagttcagt tatatgtttg
 360    ggatttttta ggtagtgggt gttgagcttg aacgctttct taattggtgg ctgcttttag
 420    gcctactatg ggtgttaaat ttttactct ctctacaagg ttttttccta gtgtccaaag
 480    agctgttcct ctttggacta acagttaaat ttacaagggg atttagaggg ttctgtgggc
 540    aaatttaaag ttgaactaag attctatctt ggacaaccag ctatcaccag gctcggtagg
```

| | SEQUENCES |
|---|---|
| 600 | tttgtcgcct ctacctataa atcttcccac tattttgcta catagacggg tgtgctcttt |
| 660 | tagctgttct taggtagctc gtctggtttc gggggtctta gctttggctc tccttgcaaa |
| 720 | gttatttcta gttaattcat tatgcagaag gtataggggt tagtccttgc tatattatgc |
| 780 | ttggttataa ttttcatct ttcccttgcg gtactatatc tattgcgcca ggtttcaatt |
| 840 | tctatcgcct atactttatt tgggtaaatg gtttggctaa acctagcccc aaacccactc |
| 900 | caccttacta ccagacaacc ttagccaaac catttaccca ataaagtat aggcgataga |
| 960 | aattgaaacc tggcgcaata gatatagtac cgcaagggaa agatgaaaaa ttataaccaa |
| 1020 | gcataatata gcaaggacta accccctatac cttctgcata atgaattaac tagaaataac |
| 1080 | tttgcaagga gagccaaagc taagaccccc gaaaccagac gagctaccta agaacagcta |
| 1140 | aaagagcaca cccgtctatg tagcaaaata gtgggaagat ttataggtag aggcgacaaa |
| 1200 | cctaccgagc ctggtgatag ctggttgtcc aagatagaat cttagttcaa ctttaaattt |
| 1260 | gcccacagaa ccctctaaat ccccttgtaa atttaactgt tagtccaaag aggaacagct |
| 1320 | ctttggacac taggaaaaaa ccttgtagag agagtaaaaa atttaacacc catagtaggc |
| 1380 | ctaaaagcag ccaccaatta agaaagcgtt caagctcaac acccactacc taaaaaatcc |
| 1440 | caaacatata actgaactcc tcacacccaa ttggaccaat ctatcaccct atagaagaac |
| 1500 | taatgttagt ataagtaaca tgaaaacatt ctcctccgca taagcctgcg tcagattaaa |
| 1560 | acactgaact gacaattaac agcccaatat ctacaatcaa ccaacaagtc attattaccc |
| 1620 | tcactgtcaa cccaacacag gcatgctcat aaggaaaggt taaaaaaagt aaaaggaact |
| 1680 | cggcaaatct taccccgcct gtttaccaaa aacatcacct ctagcatcac cagtattaga |
| 1740 | ggcaccgcct gcccagtgac acatgtttaa cggccgcggt accctaaccg tgcaaaggta |
| 1800 | gcataatcac ttgttcctta aatagggacc tgtatgaatg gctccacgag ggttcagctg |
| 1860 | tctcttactt ttaaccagtg aaattgacct gcccgtgaag aggcgggcat aacacagcaa |
| 1920 | gacgagaaga ccctatggag ctttaattta ttaatgcaaa cagtacctaa caaacccaca |
| 1980 | ggtcctaaac taccaaacct gcattaaaaa tttcggttgg ggcgacctcg gagcagaacc |
| 2040 | caacctccga gcagtacatg ctaagacttc accagtcaaa gcgaactact atactcaatt |
| 2100 | gatccaataa cttgaccaac ggaacaagtt accctaggga taacagcgca atcctattct |
| 2160 | agagtccata tcaacaatag ggtttacgac ctcgatgttg gatcaggaca tcccgatggt |
| 2220 | gcagccgcta ttaaaggttc gtttgttcaa cgattaaagt cctacgtgat ctgagttcag |
| 2280 | accggagtaa tccaggtcgg tttctatcta ccttcaaatt cctccctgta cgaaaggaca |
| 2340 | agagaaataa ggcctacttc acaaagcgcc ttcccccgta aatgatatca tctcaactta |
| 2374 | gtattatacc cacacccacc caagaacagg gttt |

<210> SEQ ID NO 2
<211> LENGTH: 1679
<212> TYPE: DNA
<213> ORGANISM: Homo saiens
<400> SEQUENCE: 2

| 60 | ggggtcttag ctttggctct ccttgcaaag ttatttctag ttaattcatt atgcagaagg |
|---|---|
| 120 | tatagggggtt agtccttgct atattatgct tggttataat ttttcatctt tcccttgcgg |
| 180 | tgctaaacct agccccaaac ccactccacc ttactaccag acaaccttag ccaaaccatt |
| 240 | tacccaaata aagtataggc gatagaaatt gaaacctggc gcaatagata tagtaccgca |
| 300 | agggaaagat gaaaaattat aaccaagcat aatatagcaa ggactaaccc ctataccttc |

| | SEQUENCES |
|---|---|
| 360 | tgcataatga attaactaga aataactttg caaggagagc caaagctaag accccgaaa |
| 420 | ccagacgagc tacctaagaa cagctaaaag agcacacccg tctatgtagc aaaatagtgg |
| 480 | gaagatttat aggtagaggc gacaaaccta ccgagcctgg tgatagctgg ttgtccaaga |
| 540 | tagaatctta gttcaacttt aaatttgccc acagaaccct ctaaatcccc ttgtaaattt |
| 600 | aactgttagt ccaaagagga acagctcttt ggacactagg aaaaaaactt gtagagagag |
| 660 | taaaaaattt aacacccata gtaggcctaa aagcagccac caattaagaa agcgttcaag |
| 720 | ctcaacaccc actacctaaa aaatcccaaa catataactg aactcctcac acccaattgg |
| 780 | accaatctat caccctatag aagaactaat gttagtataa gtaacatgaa aacattctcc |
| 840 | tccgcataag cctgcgtcag attaaaacac tgaactgaca attaacagcc caatatctac |
| 900 | aatcaaccaa caagtcatta ttaccctcac tgtcaaccca acacaggcat gctcataagg |
| 960 | aaaggttaaa aaagtaaaa ggaactcggc aaatcttacc ccgcctgttt accaaaaaca |
| 1020 | tcacctctag catcaccagt attagaggca ccgcctgccc agtgacacat gtttaacggc |
| 1080 | cgcggtaccc taaccgtgca aaggtagcat aatcacttgt tccttaaata gggacctgta |
| 1140 | tgaatggctc cacgagggtt cagctgtctc ttactttaa ccagtgaaat tgacctgccc |
| 1200 | gtgaagaggc gggcataaca cagcaagacg agaagaccct atggagcttt aatttattaa |
| 1260 | tgcaaacagt acctaacaaa cccacaggtc ctaaactacc aaacctgcat taaaaatttc |
| 1320 | ggttggggcg acctcggagc agaacccaac ctccgagcag tacatgctaa gacttcacca |
| 1380 | gtcaaagcga actactatac tcaattgatc caataacttg accaacggaa caagttaccc |
| 1440 | tagggataac agcgcaatcc tattctagag tccatatcaa caatagggtt tacgacctcg |
| 1500 | atgttggatc aggacatccc aatggtgcag ccgctattaa aggttcgttt gttcaacgat |
| 1560 | taaagtccta cgtgatctga gttcagaccg gagtaatcca ggtcggtttc tatctacttc |
| 1620 | aaattcctcc ctgtacgaaa ggacaagaga aataaggcct acttcacaaa gcgccttccc |
| 1679 | ccgtaaatga tatcatctca acttagtatt atacccacac ccacccaaga cagggttt |

<210> SEQ ID NO 3
<211> LENGTH: 1635
<212> TYPE: DNA
<213> ORGANISM: Homo sapiens
<400> SEQUENCE: 3

| 60 | ggggtcttag ctttggctct ccttgcaaag ttatttctag ttaattcatt atgcagaagg |
|---|---|
| 120 | tatagggggtt agtccttgct aaacctagcc ccaaacccac tccaccttac taccagacaa |
| 180 | ccttagccaa accatttacc caaataaagt ataggcgata gaaattgaaa cctggcgcaa |
| 240 | tagatatagt accgcaaggg aaagatgaaa aattataacc aagcataata tagcaaggac |
| 300 | taaccctat accttctgca taatgaatta actagaaata actttgcaag gagagccaaa |
| 360 | gctaagaccc ccgaaaccag acgagctacc taagaacagc taaaagagca cccgtcta |
| 420 | tgtagcaaaa tagtgggaag atttataggt agaggcgaca aacctaccga gcctggtgat |
| 480 | agctggttgt ccaagataga atcttagttc aactttaaat tgcccacag aaccctctaa |
| 540 | atccccttgt aaatttaact gttagtccaa agaggaacag ctctttggac actaggaaaa |
| 600 | aaccttgtag agagtaaa aatttaaca cccatagtag gcctaaaagc agccaccaat |
| 660 | taagaaagcg ttcaagctca cacccacta cctaaaaaat cccaaacata taactgaact |
| 720 | cctcacaccc aattggacca atctatcacc ctatagaaga actaatgtta gtataagtaa |
| 780 | catgaaaaca ttctcctccg cataagcctg cgtcagatta aaacactgaa ctgacaatta |

| | SEQUENCES |
|---|---|
| 840 | acagcccaat atctacaatc aaccaacaag tcattattac cctcactgtc aacccaacac |
| 900 | aggcatgctc ataaggaaag gttaaaaaaa gtaaaaggaa ctcggcaaat cttaccccgc |
| 960 | ctgtttacca aaaacatcac ctctagcatc accagtatta gaggcaccgc ctgcccagtg |
| 1020 | acacatgttt aacggccgcg gtaccctaac cgtgcaaagg tagcataatc acttgttcct |
| 1080 | taaataggga cctgtatgaa tggctccacg agggttcagc tgtctcttac ttttaaccag |
| 1140 | tgaaattgac ctgcccgtga agaggcgggc ataacacagc aagacgagaa gaccctatgg |
| 1200 | agctttaatt tattaatgca aacagtacct aacaaaccca caggtcctaa actaccaaac |
| 1260 | ctgcattaaa aatttcggtt ggggcgacct cggagcagaa cccaacctcc gagcagtaca |
| 1320 | tgctaagact tcaccagtca aagcgaacta ctatactcaa ttgatccaat aacttgacca |
| 1380 | acggaacaag ttaccctagg gataacagcg caatcctatt ctagagtcca tatcaacaat |
| 1440 | agggtttacg acctcgatgt tggatcagga catcccaatg gtgcagccgc tattaaaggt |
| 1500 | tcgtttgttc aacgattaaa gtcctacgtg atctgagttc agaccggagt aatccaggtc |
| 1560 | ggtttctatc tacttcaaat tcctccctgt acgaaaggac aagagaaata ggcctactt |
| 1620 | cacaaagcgc cttcccccgt aaatgatatc atctcaactt agtattatac ccacacccac |
| 1635 | ccaagaacag ggttt |

<210> SEQ ID NO 4
<211> LENGTH: 1921
<212> TYPE: DNA
<213> ORGANISM: Homo sapiens
<400> SEQUENCE: 4

| 60 | aacctccgag cagtacatgc taagacttca ccagtcaaag cgaactacta tactcaattg |
|---|---|
| 120 | atccaataac ttgaccaacg gaacaagtta ccctagggat aacagcgcaa tcctattcta |
| 180 | gagtccatat caacaatagg gtttacgacc tcgatgttgg atcaggacat cccaatggtg |
| 240 | cagccgctat taaaggttcg tttgttcaac gattaaagtc ctacgtgatc tgagttcaga |
| 300 | ccggagtaat ccaggtcggt ttctatctac ttcaaattcc tccctgtacg aaaggacaag |
| 360 | agaaataagg cctacttcac aaagcgcctt cccccgtaaa tgatatcatc tcaacttagt |
| 420 | attataccct gttcttgggt gggtgtgggt ataatactaa gttgagatga tatcatttac |
| 480 | gggggaaggc gctttgtgaa gtaggcctta tttctcttgt cctttcgtac agggaggaat |
| 540 | ttgaagtaga tagaaaccga cctggattac tccggtctga actcagatca cgtaggactt |
| 600 | taatcgttga acaaacgaac ctttaatagc ggctgcacca tcgggatgtc ctgatccaac |
| 660 | atcgaggtcg taaaccctat tgttgatatg gactctagaa taggattgcg ctgttatccc |
| 720 | tagggtaact tgttccgttg gtcaagttat tggatcaatt gagtatagta gttcgctttg |
| 780 | actggtgaag tcttagcatg tactgctcgg aggttgggtt ctgctccgag gtcgccccaa |
| 840 | ccgaaatttt taatgcaggt ttggtagttt aggacctgtg ggtttgttag gtactgtttg |
| 900 | cattaataaa ttaaagctcc ataggggtctt ctcgtcttgc tgtgttatgc ccgcctcttc |
| 960 | acgggcaggt caatttcact ggttaaaagt aagagacagc tgaaccctcg tggagccatt |
| 1020 | catacaggtc cctatttaag gaacaagtga ttatgctacc tttgcacggt tagggtaccg |
| 1080 | cggccgttaa acatgtgtca ctgggcaggc ggtgcctcta atactggtga tgctagaggt |
| 1140 | gatgttttg gtaaacaggc ggggtaagat ttgccgagtt ccttttactt tttttaacct |
| 1200 | ttcctatga gcatgcctgt gttgggttga cagtgagggt aataatgact tgttggttga |
| 1260 | ttgtagatat tgggctgtta attgtcagtt cagtgtttta atctgacgca ggcttatgcg |

| | SEQUENCES |
|---|---|
| 1320 | gaggagaatg ttttcatgtt acttatacta acattagttc ttctataggg tgatagattg |
| 1380 | gtccaattgg gtgtgaggag ttcagttata tgtttgggat ttttttaggta gtgggtgttg |
| 1440 | agcttgaacg ctttcttaat tggtggctgc ttttaggcct actatgggtg ttaaattttt |
| 1500 | tactctctct acaaggtttt ttcctagtgt ccaaagagct gttcctcttt ggactaacag |
| 1560 | ttaaatttac aagggggattt agagggttct gtgggcaaat ttaaagttga actaagattc |
| 1620 | tatcttggac aaccagctat caccaggctc ggtaggtttg tcgcctctac ctataaatct |
| 1680 | tcccactatt ttgctacata gacgggtgtg ctcttttagc tgttcttagg tagctcgtct |
| 1740 | ggtttcgggg gtcttagctt tggctctcct tgcaaagtta tttctagtta attcattatg |
| 1800 | cagaaggtat aggggttagt ccttgctata ttatgcttgg ttataatttt tcatctttcc |
| 1860 | cttgcggtac tatatctatt gcgccaggtt tcaatttcta tcgcctatac tttatttggg |
| 1920 | taaatggttt ggctaaggtt gtctggtagt aaggtggagt gggtttgggg ctaggtttag |
| 1921 | c |

<210> SEQ ID NO 5
<211> LENGTH: 1744
<212> TYPE: DNA
<213> ORGANISM: Homo sapiens
<400> SEQUENCE: 5

| 60 | tagggataac agcgcaatcc tattctagag tccatatcaa caataggggtt tacgacctcg |
|---|---|
| 120 | atgttggatc aggacatccc gatggtgcag ccgctattaa aggttcgttt gttcaacgat |
| 180 | taaagtccta cgtgatctga gttcagaccg gagtaatcca ggtcggtttc tatctacctt |
| 240 | caaattcctc cctgttcttg ggtgggtgtg ggtataatac taagttgaga tgatatcatt |
| 300 | tacgggggaa ggcgcttttgt gaagtaggcc ttatttctct tgtcctttcg tacagggagg |
| 360 | aatttgaagt agatagaaac cgacctggat tactccggtc tgaactcaga tcacgtagga |
| 420 | ctttaatcgt tgaacaaacg aacctttaat agcggctgca ccatcgggat gtcctgatcc |
| 480 | aacatcgagg tcgtaaaccc tattgttgat atggactcta aataggatt gcgctgttat |
| 540 | ccctagggta acttgttccg ttggtcaagt tattggatca attgagtata gtagttcgct |
| 600 | ttgactggtg aagtcttagc atgtactgct cggaggttgg gttctgctcc gaggtcgccc |
| 660 | caaccgaaat ttttaatgca ggtttggtag tttaggacct gtgggtttgt taggtactgt |
| 720 | ttgcattaat aaattaaagc tccatagggt cttctcgtct tgctgtgtta tgcccgcctc |
| 780 | ttcacgggca ggtcaatttc actggttaaa agtaagagac agctgaaccc tcgtggagcc |
| 840 | attcatacag gtccctattt aaggaacaag tgattatgct acctttgcac ggttagggta |
| 900 | ccgcggccgt taaacatgtg tcactgggca ggcggtgcct ctaatactgg tgatgctaga |
| 960 | ggtgatgttt ttggtaaaca ggcggggtaa gatttgccga gttccttta ctttttttaa |
| 1020 | cctttcctta tgagcatgcc tgtgttgggt tgacagtgag ggtaataatg acttgttggt |
| 1080 | tgattgtaga tattgggctg ttaattgtca gttcagtgtt ttaatctgac gcaggcttat |
| 1140 | gcggaggaga atgttttcat gttacttata ctaacattag ttcttctata gggtgataga |
| 1200 | ttggtccaat tgggtgtgag gagttcagtt atatgtttgg gattttttag gtagtgggtg |
| 1260 | ttgagcttga acgctttctt aattggtggc tgcttttagg cctactatgg tgttaaatt |
| 1320 | ttttactctc tctacaaggt ttttcctag tgtccaaaga gctgttcctc tttggactaa |
| 1380 | cagttaaatt tacaagggga tttagagggt tctgtgggca aatttaaagt tgaactaaga |
| 1440 | ttctatcttg gacaaccagc tatcaccagg ctcggtaggt tgtcgcctc tacctataaa |

| | SEQUENCES |
|---|---|
| 1500 | tcttcccact attttgctac atagacgggt gtgctctttt agctgttctt aggtagctcg |
| 1560 | tctggtttcg ggggtcttag ctttggctct ccttgcaaag ttatttctag ttaattcatt |
| 1620 | atgcagaagg tatagggggtt agtccttgct atattatgct tggttataat ttttcatctt |
| 1680 | tcccttgcgg tactatatct attgcgccag gtttcaattt ctatcgccta tactttattt |
| 1740 | gggtaaatgg tttggctaag gttgtctggt agtaaggtgg agtgggtttg gggctaggtt |
| 1744 | tagc |
| <210> | SEQ ID NO 6 |
| <211> | LENGTH: 1854 |
| <212> | TYPE: DNA |
| <213> | ORGANISM: Homo sapiens |
| <400> | SEQUENCE: 6 |
| 60 | gaactcggca aatcttaccc cgcctgttta ccaaaaacat cacctctagc atcaccagta |
| 120 | ttagaggcac cgcctgccca gtgacacatg tttaacggcc gcggtaccct aaccgtgcaa |
| 180 | aggtagcata atcacttgtt ccttaaatag gacctgtat gaatggctcc acgagggttc |
| 240 | agctgtctct tacttttaac cagtgaaatt gacctgcccg tgaagaggcg ggcatgacac |
| 300 | agcaagacga gaagacccta tggagcttta atttattaat gcaaacagta cctaacaaac |
| 360 | cctgttcttg ggtgggtgtg ggtataatac taagttgaga tgatatcatt tacggggaa |
| 420 | ggcgctttgt gaagtaggcc ttatttctct tgtcctttcg tacagggagg aatttgaagt |
| 480 | agatagaaac cgacctggat tactccggtc tgaactcaga tcacgtagga ctttaatcgt |
| 540 | tgaacaaacg aacctttaat agcggctgca ccatcgggat gtcctgatcc aacatcgagg |
| 600 | tcgtaaaccc tattgttgat atggactcta gaataggatt gcgctgttat ccctagggta |
| 660 | acttgttccg ttggtcaagt tattggatca attgagtata gtagttcgct ttgactggtg |
| 720 | aagtcttagc atgtactgct cggaggttgg gttctgctcc gaggtcgccc caaccgaaat |
| 780 | ttttaatgca ggtttggtag tttaggacct gtgggtttgt taggtactgt ttgcattaat |
| 840 | aaattaaagc tccatagggt cttctcgtct tgctgtgtta tgcccgcctc ttcacgggca |
| 900 | ggtcaatttc actggttaaa agtaagagac agctgaaccc tcgtggagcc attcatacag |
| 960 | gtccctattt aaggaacaag tgattatgct acctttgcac ggttaggta ccgcggccgt |
| 1020 | taaacatgtg tcactgggca ggcggtgcct ctaatactgg tgatgctaga ggtgatgttt |
| 1080 | ttggtaaaca ggcggggtaa gatttgccga gttccttta cttttttaa cctttcctta |
| 1140 | tgagcatgcc tgtgttgggt tgacagtgag ggtaataatg acttgttggt tgattgtaga |
| 1200 | tattgggctg ttaattgtca gttcagtgtt ttaatctgac gcaggcttat gcggaggaga |
| 1260 | atgttttcat gttacttata ctaacattag ttcttctata gggtgataga ttggtccaat |
| 1320 | tgggtgtgag gagttcagtt atatgtttgg gattttttag gtagtgggtg ttgagcttga |
| 1380 | acgctttctt aattggtggc tgcttttagg cctactatgg gtgttaaatt ttttactctc |
| 1440 | tctacaaggt tttttcctag tgtccaaaga gctgttcctc tttggactaa cagttaaatt |
| 1500 | tacaagggga tttagagggt tctgtgggca aatttaaagt tgaactaaga ttctatcttg |
| 1560 | gacaaccagc tatcaccagg ctcggtaggt tgtcgcctc tacctataaa tcttcccact |
| 1620 | attttgctac atagacgggt gtgctctttt agctgttctt aggtagctcg tctggtttcg |
| 1680 | ggggtcttag ctttggctct ccttgcaaag ttatttctag ttaattcatt atgcagaagg |
| 1740 | tataggggtt agtccttgct atattatgct tggttataat ttttcatctt tcccttgcgg |
| 1800 | tactatatct attgcgccag gtttcaattt ctatcgccta tactttattt gggtaaatgg |

| SEQUENCES |
|---|

```
1854    tttggctaag gttgtctggt agtaaggtgg agtgggtttg gggctaggtt tagc

<210>   SEQ ID NO 7
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 7
        taggtttagc accgcaaggg                                          20

<210>   SEQ ID NO 8
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 8
        taggtttagc aaggactaac                                          20

<210>   SEQ ID NO 9
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 9
        ggggtaagat ttgccgag                                            18

<210>   SEQ ID NO 10
<211>   LENGTH: 22
<212>   TYPE: DNA
<213>   ORGANISM: Artificial Sequence
<220>   FEATURE:
<223>   OTHER INFORMATION: Antisense Oligonucleotide
<400>   SEQUENCE: 10
        atgctagagg tgatgttttt gg                                       22

<210>   SEQ ID NO 11
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 11
        cggtgcctct aatactgg                                            18

<210>   SEQ ID NO 12
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 12
        gttaaacatg tgtcactggg                                          20

<210>   SEQ ID NO 13
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 13
        ttgcacggtt agggtacc                                            18

<210>   SEQ ID NO 14
<211>   LENGTH: 21
<212>   TYPE: DNA
<213>   ORGANISM: Artificial Sequence
<220>   FEATURE:
<223>   OTHER INFORMATION: Antisense Oligonucleotide
<400>   SEQUENCE: 14
        ggaacaagtg attatgctac c                                        21

<210>   SEQ ID NO 15
<211>   LENGTH: 21
<212>   TYPE: DNA
```

|  SEQUENCES |
| --- |

```
<213>   ORGANISM: Artificial Sequence
<220>   FEATURE:
<223>   OTHER INFORMATION: Antisense Oligonucleotide
<400>   SEQUENCE: 15
        ggagccattc atacaggtcc c         21

<210>   SEQ ID NO 16
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 16
        agtaagagac agctgaaccc            20

<210>   SEQ ID NO 17
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 17
        ggcaggtcaa tttcactgg             19

<210>   SEQ ID NO 18
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 18
        gctgtgttat gcccgcctc             19

<210>   SEQ ID NO 19
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 19
        agctccatag ggtcttctc             19

<210>   SEQ ID NO 20
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 20
        gttaggtact gtttgcatta            20

<210>   SEQ ID NO 21
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 21
        aagtcttagc atgtactg              18

<210>   SEQ ID NO 22
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 22
        tagtagttcg ctttgactg             19

<210>   SEQ ID NO 23
<211>   LENGTH: 19
<212>   TYPE: DNA
<213>   ORGANISM: Artificial Sequence
<220>   FEATURE:
<223>   OTHER INFORMATION: OAntisense Oligonucleotide
<400>   SEQUENCE: 23
        caagttattg gatcaattg             19
```

```
                                  SEQUENCES
---------------------------------------------------------------------------

<210>   SEQ ID NO 24
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 24
        gggtaacttg ttccgttg                                               18

<210>   SEQ ID NO 25
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 25
        aataggattg cgctgtta                                               18

<210>   SEQ ID NO 26
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 26
        cctattgttg atatggac                                               18

<210>   SEQ ID NO 27
<211>   LENGTH: 17
<212>   TYPE: DNA
<213>   ORGANISM: Artificial Sequence
<220>   FEATURE:
<223>   OTHER INFORMATION: Antisense Oligonucleotide
<400>   SEQUENCE: 27
        ctgatccaac atcgagg                                                17

<210>   SEQ ID NO 28
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 28
        tagcggctgc accattgg                                               18

<210>   SEQ ID NO 29
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 29
        gttgaacaaa cgaacctttt                                             19

<210>   SEQ ID NO 30
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 30
        aactcagatc acgtaggac                                              19

<210>   SEQ ID NO 31
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 31
        cgacctggat tactccgg                                               18

<210>   SEQ ID NO 32
<211>   LENGTH: 18
<212>   TYPE: DNA
<213>   ORGANISM: Artificial Sequence
```

| SEQUENCES |
|---|
| <220> FEATURE:
<223> OTHER INFORMATION: Antisense Oligonucleotide
<400> SEQUENCE: 32
ggaatttgaa gtagatag                                         18

<210> SEQ ID NO 33
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 33
ctcttgtcct ttcgtacag                                        19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 34
ggcgctttgt gaagtagg                                         18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 35
gttgagatga tatcatttac gg                                    22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 36
cacccaccca agaacagg                                         18

<210> SEQ ID NO 37
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 37
caacttagta ttatacccac accca                                 25

<210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 38
tcccccgtaa atgattacat ct                                    22

<210> SEQ ID NO 39
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 39
gagaaataag gcctacttca caaag                                 25

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 40
caaattcctc cctgtacgaa ag                                    22 |

| SEQUENCES |
|---|

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 41
agtaatccag gtcggtttct atct                                              24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 42
aagtcctagc tgatctgagt tcag                                              24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 43
gctattaaag gttcgtttgt tcaac                                             25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide
<400> SEQUENCE: 44
tcccgatggt gcagcc                                                       16

<210> SEQ ID NO 45
<211> LENGTH: 22
<212> TYPE: DNA
<213> ORGANISM: Artificial Sequence
<220> FEATURE:
<223> OTHER INFORMATION: Antisense Oligonucleotide
<400> SEQUENCE: 45
ttacgacctc gatgttggat ca                                                22

<210> SEQ ID NO 46
<211> LENGTH: 25
<212> TYPE: DNA
<213> ORGANISM: Artificial Sequence
<220> FEATURE:
<223> OTHER INFORMATION: Antisense Oligonucleotide
<400> SEQUENCE: 46
atcctattct agagtccata tcaac                                             25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 47
aataggattg cgctgttatc ccta                                              24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 48
tagggataac agcgcatacc tatt                                              24

<210> SEQ ID NO 49
<211> LENGTH: 23
<212> TYPE: DNA
<213> ORGANISM: Artificial Sequence
<220> FEATURE:

```
                               SEQUENCES
<223>   OTHER INFORMATION: Antisense Oligonucleotide
<400>   SEQUENCE: 49
        ggaacaagtt accctaggga taa              23

<210>   SEQ ID NO 50
<211>   LENGTH: 23
<212>   TYPE: DNA
<213>   ORGANISM: Artificial Sequence
<220>   FEATURE:
<223>   OTHER INFORMATION: Antisense Oligonucleotide
<400>   SEQUENCE: 50
        ttgatccaat aacttgacca acg              23

<210>   SEQ ID NO 51
<211>   LENGTH: 21
<212>   TYPE: DNA
<213>   ORGANISM: Artificial Sequence
<220>   FEATURE:
<223>   OTHER INFORMATION: Antisense Oligonucleotide
<400>   SEQUENCE: 51
        acttcaccag tcaaagcgaa c                21

<210>   SEQ ID NO 52
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 52
        aacccaacct ccgagcag                    18

<210>   SEQ ID NO 53
<211>   LENGTH: 16
<212>   TYPE: DNA
<213>   ORGANISM: Artificial Sequence
<220>   FEATURE:
<223>   OTHER INFORMATION: Antisense Oligonucleotide
<400>   SEQUENCE: 53
        gttggggcga cctcgg                      16

<210>   SEQ ID NO 54
<211>   LENGTH: 22
<212>   TYPE: DNA
<213>   ORGANISM: Artificial Sequence
<220>   FEATURE:
<223>   OTHER INFORMATION: Antisense Oligonucleotide
<400>   SEQUENCE: 54
        aaactaccaa acctgcttaa aa               22

<210>   SEQ ID NO 55
<211>   LENGTH: 24
<212>   TYPE: DNA
<213>   ORGANISM: Artificial Sequence
<220>   FEATURE:
<223>   OTHER INFORMATION: Antisense Oligonucleotide
<400>   SEQUENCE: 55
        aaacagtacc taacaaaccc acag             24

<210>   SEQ ID NO 56
<211>   LENGTH: 25
<212>   TYPE: DNA
<213>   ORGANISM: Artificial Sequence
<220>   FEATURE:
<223>   OTHER INFORMATION: Antisense Oligonucleotide
<400>   SEQUENCE: 56
        gaccctatgg agctttaatt tatta            25

<210>   SEQ ID NO 57
<211>   LENGTH: 23
<212>   TYPE: DNA
<213>   ORGANISM: Artificial Sequence
<220>   FEATURE:
<223>   OTHER INFORMATION: Antisense Oligonucleotide
<400>   SEQUENCE: 57
        cataacacag caagacgaga aga              23

<210>   SEQ ID NO 58
```

| SEQUENCES |
|---|

```
<211>   LENGTH: 18
<212>   TYPE: DNA
<213>   ORGANISM: Artificial Sequence
<220>   FEATURE:
<223>   OTHER INFORMATION: Antisense Oligonucleotide
<400>   SEQUENCE: 58
        tgacctgccc gtgaagag                                              18

<210>   SEQ ID NO 59
<211>   LENGTH: 26
<212>   TYPE: DNA
<213>   ORGANISM: Artificial Sequence
<220>   FEATURE:
<223>   OTHER INFORMATION: Antisense Oligonucleotide
<400>   SEQUENCE: 59
        cagctgtctc ttacttttaa ccagtg                                     26

<210>   SEQ ID NO 60
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 60
        ctgtatgaat ggctccacga                                            20

<210>   SEQ ID NO 61
<211>   LENGTH: 26
<212>   TYPE: DNA
<213>   ORGANISM: Artificial Sequence
<220>   FEATURE:
<223>   OTHER INFORMATION: Antisense Oligonucleotide
<400>   SEQUENCE: 61
        agcataatca cttgttcctt aaatag                                     26

<210>   SEQ ID NO 62
<211>   LENGTH: 23
<212>   TYPE: DNA
<213>   ORGANISM: Artificial Sequence
<220>   FEATURE:
<223>   OTHER INFORMATION: Antisense Oligonucleotide
<400>   SEQUENCE: 62
        accgtgcaaa ggtagcataa tca                                        23

<210>   SEQ ID NO 63
<211>   LENGTH: 23
<212>   TYPE: DNA
<213>   ORGANISM: Artificial Sequence
<220>   FEATURE:
<223>   OTHER INFORMATION: Antisense Oligonucleotide
<400>   SEQUENCE: 63
        tgattatgct acctttgcac ggt                                        23

<210>   SEQ ID NO 64
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 64
        gtaccctaac cgtgcaaag                                             19

<210>   SEQ ID NO 65
<211>   LENGTH: 21
<212>   TYPE: DNA
<213>   ORGANISM: Artificial Sequence
<220>   FEATURE:
<223>   OTHER INFORMATION: Antisense Oligonucleotide
<400>   SEQUENCE: 65
        cctgcccagtgacacatgtt t                                           21

<210>   SEQ ID NO 66
<211>   LENGTH: 25
<212>   TYPE: DNA
<213>   ORGANISM: Artificial Sequence
<220>   FEATURE:
<223>   OTHER INFORMATION: Antisense Oligonucleotide
```

| SEQUENCES |
|---|

<400> SEQUENCE: 66
cacctctagc atcaccagta ttaga    25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 67
cttaccccgc ctgtttacca    20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide
<400> SEQUENCE: 68
aggttaaaaa aagtaaaagg aactcg    26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 69
cccaacacag gcatgctca    19

<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 70
accaacaagt cattattacc ctca    24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 71
tgacaattaa cagcccaata tcta    24

<210> SEQ ID NO 72
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 72
gcctgcgtca gattaaaaca c    21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide
<400> SEQUENCE: 73
gtaacatgaa aacattctcc tccg    24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide
<400> SEQUENCE: 74
tatcacccta tagaagaact aatgttag    28

<210> SEQ ID NO 75
<211> LENGTH: 21

| SEQUENCES |
|---|

```
<212>  TYPE: DNA
<213>  ORGANISM: Artificial Sequence
<220>  FEATURE:
<223>  OTHER INFORMATION: Antisense Oligonucleotide
<400>  SEQUENCE: 75
       ctgaactcct cacacccaat t                                           21

<210>  SEQ ID NO 76
<211>  LENGTH: 23
<212>  TYPE: DNA
<213>  ORGANISM: Artificial Sequence
<220>  FEATURE:
<223>  OTHER INFORMATION: Antisense Oligonucleotide
<400>  SEQUENCE: 76
       cactacctaa aaatcccaa aca                                          23

<210>  SEQ ID NO 77
<211>  LENGTH: 21
<212>  TYPE: DNA
<213>  ORGANISM: Artificial Sequence
<220>  FEATURE:
<223>  OTHER INFORMATION: Antisense Oligonucleotide
<400>  SEQUENCE: 77
       ttaagaaagc gttcaagctc a                                           21

<210>  SEQ ID NO 78
<211>  LENGTH: 21
<212>  TYPE: DNA
<213>  ORGANISM: Artificial Sequence
<220>  FEATURE:
<223>  OTHER INFORMATION: Antisense Oligonucleotide
<400>  SEQUENCE: 78
       catagtaggc ctaaaagcag c                                           21

<210>  SEQ ID NO 79
<211>  LENGTH: 26
<212>  TYPE: DNA
<213>  ORGANISM: Artificial Sequence
<220>  FEATURE:
<223>  OTHER INFORMATION: Antisense Oligonucleotide
<400>  SEQUENCE: 79
       aaaccttgta gagagagtaa aaaatt                                      26

<210>  SEQ ID NO 80
<211>  LENGTH: 24
<212>  TYPE: DNA
<213>  ORGANISM: Artificial Sequence
<220>  FEATURE:
<223>  OTHER INFORMATION: Antisense Oligonucleotide
<400>  SEQUENCE: 80
       aaagaggaac agctctttgg acac                                        24

<210>  SEQ ID NO 81
<211>  LENGTH: 24
<212>  TYPE: DNA
<213>  ORGANISM: Artificial Sequence
<220>  FEATURE:
<223>  OTHER INFORMATION: Antisense Oligonucleotide
<400>  SEQUENCE: 81
       aatccccttg taaatttaac tgtt                                        24

<210>  SEQ ID NO 82
<211>  LENGTH: 21
<212>  TYPE: DNA
<213>  ORGANISM: Artificial Sequence
<220>  FEATURE:
<223>  OTHER INFORMATION: Antisense Oligonucleotide
<400>  SEQUENCE: 82
       ctttaaattt gcccacagaa c                                           21

<210>  SEQ ID NO 83
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 83
```

-continued

| SEQUENCES |
|---|

```
            ggttgtccaa gatagaatct                                    20

<210>       SEQ ID NO 84
<211>       LENGTH: 19
<212>       TYPE: DNA
<213>       ORGANISM: Artificial Sequence
<220>       FEATURE:
<223>       OTHER INFORMATION: Antisense Oligonucleotide
<400>       SEQUENCE: 84
            acaaacctac cgagcctgg                                     19

<210>       SEQ ID NO 85
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 85
            aagatttata ggtagaggcg                                    20

<210>       SEQ ID NO 86
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 86
            cccgtctatg tagcaaaata                                    20

<210>       SEQ ID NO 87
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 87
            acctaagaac agctaaaaga                                    20

<210>       SEQ ID NO 88
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 88
            taagaccccc gaaaccagac                                    20

<210>       SEQ ID NO 89
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 89
            ataactttgc aaggagagcc                                    20

<210>       SEQ ID NO 90
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 90
            cttctgcata atgaattaac                                    20

<210>       SEQ ID NO 91
<211>       LENGTH: 20
<212>       TYPE: DNA
<213>       ORGANISM: Artificial Sequence
<220>       FEATURE:
<223>       OTHER INFORMATION: Antisense Oligonucleotide
<400>       SEQUENCE: 91
            atatagcaag gactaacccc                                    20

<210>       SEQ ID NO 92
<211>       LENGTH: 20
<212>       TYPE: DNA
```

| SEQUENCES |
|---|

```
<213>   ORGANISM: Artificial Sequence
<220>   FEATURE:
<223>   OTHER INFORMATION: Antisense Oligonucleotide
<400>   SEQUENCE: 92
        agatgaaaaa ttataaccaa          20

<210>   SEQ ID NO 93
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 93
        caatagatat agtaccgcaa          20

<210>   SEQ ID NO 94
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 94
        aggcgataga aattgaaacc          20

<210>   SEQ ID NO 95
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 95
        tagccaaacc atttacccaa          20

<210>   SEQ ID NO 96
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 96
        caccttacta ccagacaacc          20

<210>   SEQ ID NO 97
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 97
        ctaaacctag ccccaaacc           19

<210>   SEQ ID NO 98
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 98
        ctagcatcac cagtattaga          20

<210>   SEQ ID NO 99
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 99
        ttaccaaaaa catcacctct          20

<210>   SEQ ID NO 100
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 100
        gaactcggca aatcttaccc          20
```

| SEQUENCES |
|---|

```
<210>   SEQ ID NO 101
<211>   LENGTH: 20
<212>   TYPE: DNA
<213>   ORGANISM: Artificial Sequence
<220>   FEATURE:
<223>   OTHER INFORMATION: Sense Oligonucleotide
<400>   SEQUENCE: 101
        gggtaagatt tgccgagttc                                        20

<210>   SEQ ID NO 102
<211>   LENGTH: 21
<212>   TYPE: DNA
<213>   ORGANISM: Artificial Sequence
<220>   FEATURE:
<223>   OTHER INFORMATION: Antisense Oligonucleotide
<400>   SEQUENCE: 102
        gctcataagg aaaggttaaa a                                      21

<210>   SEQ ID NO 103
<211>   LENGTH: 17
<212>   TYPE: DNA
<213>   ORGANISM: Artificial Sequence
<220>   FEATURE:
<223>   OTHER INFORMATION: Antisense Oligonucleotide
<400>   SEQUENCE: 103
        gtcaacccaa cacaggc                                           17

<210>   SEQ ID NO 104
<211>   LENGTH: 21
<212>   TYPE: DNA
<213>   ORGANISM: Artificial Sequence
<220>   FEATURE:
<223>   OTHER INFORMATION: Antisense Oligonucleotide
<400>   SEQUENCE: 104
        accaacaagt cattattacc c                                      21

<210>   SEQ ID NO 105
<211>   LENGTH: 22
<212>   TYPE: DNA
<213>   ORGANISM: Artificial Sequence
<220>   FEATURE:
<223>   OTHER INFORMATION: Sense Oligonucleotide
<400>   SEQUENCE: 105
        ggttgattgt agatattggg ct                                     22

<210>   SEQ ID NO 106
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 106
        attaacagcc caatatctac                                        20

<210>   SEQ ID NO 107
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 107
        tgcgtcagat taaaacactg                                        20

<210>   SEQ ID NO 108
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 108
        aaaacattct cctccgcata                                        20

<210>   SEQ ID NO 109
<211>   LENGTH: 18
<212>   TYPE: DNA
<213>   ORGANISM: Artificial Sequence
```

| SEQUENCES |
|---|

```
<220>   FEATURE:
<223>   OTHER INFORMATION: Antisense Oligonucleotide
<400>   SEQUENCE: 109
        gttagtataa gtaacatg                                           18

<210>   SEQ ID NO 110
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 110
        tggaccaatc tatcaccct                                          19

<210>   SEQ ID NO 111
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 111
        acatataact gaactcctca                                         20

<210>   SEQ ID NO 112
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 112
        cacccactac ctaaaaaatc                                         20

<210>   SEQ ID NO 113
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 113
        caccaattaa gaaagcgttg                                         20

<210>   SEQ ID NO 114
<211>   LENGTH: 22
<212>   TYPE: DNA
<213>   ORGANISM: Artificial Sequence
<220>   FEATURE:
<223>   OTHER INFORMATION: Antisense Oligonucleotide
<400>   SEQUENCE: 114
        taggcctaaa agcagccacc aa                                      22

<210>   SEQ ID NO 115
<211>   LENGTH: 22
<212>   TYPE: DNA
<213>   ORGANISM: Artificial Sequence
<220>   FEATURE:
<223>   OTHER INFORMATION: Sense Oligonucleotide
<400>   SEQUENCE: 115
        ttggtggctg cttttaggcc ta                                      22

<210>   SEQ ID NO 116
<211>   LENGTH: 19
<212>   TYPE: DNA
<213>   ORGANISM: Artificial Sequence
<220>   FEATURE:
<223>   OTHER INFORMATION: Antisense Oligonucleotide
<400>   SEQUENCE: 116
        taacacccat agtaggcct                                          19

<210>   SEQ ID NO 117
<211>   LENGTH: 20
<212>   TYPE: DNA
<213>   ORGANISM: Artificial Sequence
<220>   FEATURE:
<223>   OTHER INFORMATION: Antisense Oligonucleotide
<400>   SEQUENCE: 117
        aaccttgtag agagagtaaa                                         20
```

| SEQUENCES |
|---|
| <210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 118
aacagctctt tggacactag 20

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 119
aactgttagt ccaaagag 18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 120
ctctaaatcc ccttgtaaa 19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 121
actttaaatt tgcccacag 19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 122
ggttgtccaa gatagaatc 19

<210> SEQ ID NO 123
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 123
acaaacctac cgagcctcc 19

<210> SEQ ID NO 124
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 124
atttataggt tagaggcg 18

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 125
atgtagcaaa atagtgggaa 20

<210> SEQ ID NO 126
<211> LENGTH: 21
<212> TYPE: DNA
<213> ORGANISM: Artificial Sequence
<220> FEATURE: |

| SEQUENCES |
|---|
| <223> OTHER INFORMATION: Antisense Oligonucleotide
<400> SEQUENCE: 126
taagaacagc taaaagagca c 21

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 127
cgaaaccaga cgagctac 18

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide
<400> SEQUENCE: 128
ggggtcttag ctttggctct cc 22

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 129
taactttgca aggagagcca 20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 130
accttctgca taatgaat 18

<210> SEQ ID NO 131
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 131
atatagcaag gactaaccc 19

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 132
gatgaaaaat tataaccaag 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 133
aatagatata gtaccgcaag 20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 134
cgatagaaat tgaaacc 17

<210> SEQ ID NO 135 |

| SEQUENCES |
|---|
| <211> LENGTH: 20
<212> TYPE: DNA
<213> ORGANISM: Artificial Sequence
<220> FEATURE:
<223> OTHER INFORMATION: Sense Oligonucleotide
<400> SEQUENCE: 135
tactttattt gggtaaatgg                                                20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 136
ccatttaccc aaataaagta                                                20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 137
ttagccaaac catttaccca                                                20

210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 138
aaggtggagt gggtttgggg c                                              21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 139
gctaaggttg tctggta                                                   17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 140
atcgcctata ctttatttgg                                                20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 141
atctattgcg ccaggtttca                                                20

<210> SEQ ID NO 142
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 142
ttttcatctt tcccttgcg                                                 19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide |

| SEQUENCES |
|---|
| <400> SEQUENCE: 143
tccttgctat attatgcttg    20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 144
cattatgcag aaggtatagg    20

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 145
tctccttgca aagttatt    18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 146
tttcgggggt cttagctttg    20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 147
ctgttcttag gtagctcg    18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 148
tgctacatag acgggtgtg    19

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 149
cctctaccta taaatcttcc    20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 150
gctatcacca ggctcgg    17

<210> SEQ ID NO 151
<211> LENGTH: 17
<212> TYPE: DNA
<213> ORGANISM: Artificial Sequence
<220> FEATURE:
<223> OTHER INFORMATION: Antisense Oligonucleotide
<400> SEQUENCE: 151
aagttgaact aagattc    17

<210> SEQ ID NO 152
<211> LENGTH: 20 |

| SEQUENCES |
| --- |

```
<212>  TYPE: DNA
<213>  ORGANISM: Artificial Sequence
<220>  FEATURE:
<223>  OTHER INFORMATION: Antisense Oligonucleotide
<400>  SEQUENCE: 152
       gagggttctg tgggcaaatt            20

<210>  SEQ ID NO 153
<211>  LENGTH: 19
<212>  TYPE: DNA
<213>  ORGANISM: Artificial Sequence
<220>  FEATURE:
<223>  OTHER INFORMATION: Antisense Oligonucleotide
<400>  SEQUENCE: 153
       acagttaaat ttacaaggg             19

<210>  SEQ ID NO 154
<211>  LENGTH: 19
<212>  TYPE: DNA
<213>  ORGANISM: Artificial Sequence
<220>  FEATURE:
<223>  OTHER INFORMATION: Antisense Oligonucleotide
<400>  SEQUENCE: 154
       gtgtccaaag agctgttcc             19

<210>  SEQ ID NO 155
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 155
       tactctctct acaaggtttt            20

<210>  SEQ ID NO 156
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 156
       taggcctact atgggtgtta            20

<210>  SEQ ID NO 157
<211>  LENGTH: 21
<212>  TYPE: DNA
<213>  ORGANISM: Artificial Sequence
<220>  FEATURE:
<223>  OTHER INFORMATION: Antisense Oligonucleotide
<400>  SEQUENCE: 157
       aacgctttct taattggtgg c          21

<210>  SEQ ID NO 158
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 158
       ttttaggtag tgggtgttga            20

<210>  SEQ ID NO 159
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 159
       ggagttcagt tatatgtttg            20

<210>  SEQ ID NO 160
<211>  LENGTH: 20
<212>  TYPE: DNA
<213>  ORGANISM: Artificial Sequence
<220>  FEATURE:
<223>  OTHER INFORMATION: Antisense Oligonucleotide
<400>  SEQUENCE: 160
```

-continued

| SEQUENCES |
|---| tgatagattg gtccaattgg 20

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 161
ctaacattag ttcttctata g 21

<210> SEQ ID NO 162
<211> LENGTH: 18
<212> TYPE: DNA
<213> ORGANISM: Artificial Sequence
<220> FEATURE:
<223> OTHER INFORMATION: Antisense Oligonucleotide
<400> SEQUENCE: 162
atgcggagga gaatgttt 18

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide
<400> SEQUENCE: 163
tcagtgtttt aatctgacg 19

<210> SEQ ID NO 164
<211> LENGTH: 21
<212> TYPE: DNA
<213> ORGANISM: Artificial Sequence
<220> FEATURE:
<223> OTHER INFORMATION: Antisense Oligonucleotide
<400> SEQUENCE: 164
gtagatattg ggctgttaatt 21

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide
<400> SEQUENCE: 165
gtgagggtaa taatgacttg 20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide
<400> SEQUENCE: 166
atgagcatgc ctgtgttggt 20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide
<400> SEQUENCE: 167
ggtaagattt gccgagttc 19

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide
<400> SEQUENCE: 168
tggtgatgct agaggtgatg 20

<210> SEQ ID NO 169
<211> LENGTH: 15
<212> TYPE: DNA

```
                                SEQUENCES
<213>   ORGANISM: Artificial Sequence
<220>   FEATURE:
<223>   OTHER INFORMATION: Oligonucleotide
<400>   SEQUENCE: 169
        gcggtgcctc taata                                              15

<210>   SEQ ID NO 170
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 170
        ggccgttaaa catgtgtcac                                         20

<210>   SEQ ID NO 171
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 171
        tgattatgct acctttgcac                                         20

<210>   SEQ ID NO 172
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 172
        ttaaggaaca agtgattatg                                         20

<210>   SEQ ID NO 173
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 173
        tggagccatt catacaggtc                                         20

<210>   SEQ ID NO 174
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 174
        aaaagtaaga gacagctgaa                                         20

<210>   SEQ ID NO 175
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 175
        cacgggcagg tcaatttcac                                         20

<210>   SEQ ID NO 176
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 176
        gtcttgctgt gttatgcccg                                         20

<210>   SEQ ID NO 177
<211>   LENGTH: 19
<212>   TYPE: DNA
<213>   ORGANISM: Artificial Sequence
<220>   FEATURE:
<223>   OTHER INFORMATION: Oligonucleotide
<400>   SEQUENCE: 177
        aattaaagct ccatagggt                                          19
```

-continued

| SEQUENCES |
|---|

```
<210>   SEQ ID NO 178
<211>   LENGTH: 21
<212>   TYPE: DNA
<213>   ORGANISM: Artificial Sequence
<220>   FEATURE:
<223>   OTHER INFORMATION: Oligonucleotide
<400>   SEQUENCE: 178
        gtttgttagg tactgtttgc a                                         21

<210>   SEQ ID NO 179
<211>   LENGTH: 19
<212>   TYPE: DNA
<213>   ORGANISM: Artificial Sequence
<220>   FEATURE:
<223>   OTHER INFORMATION: Oligonucleotide
<400>   SEQUENCE: 179
        aggtttggta gtttaggac                                            19

<210>   SEQ ID NO 180
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 180
        gccccaaccg aaatttttaa                                           20

<210>   SEQ ID NO 181
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 181
        ctcggaggtt gggttctgct                                           20

<210>   SEQ ID NO 182
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 182
        ctggtgaagt cttagcatgt                                           20

<210>   SEQ ID NO 183
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 183
        caattgagta tagtagttcg                                           20

<210>   SEQ ID NO 184
<211>   LENGTH: 19
<212>   TYPE: DNA
<213>   ORGANISM: Artificial Sequence
<220>   FEATURE:
<223>   OTHER INFORMATION: Oligonucleotide
<400>   SEQUENCE: 184
        tgttccgttg gtcaagtta                                            19

<210>   SEQ ID NO 185
<211>   LENGTH: 20
<212>   TYPE: DNA
<213>   ORGANISM: Artificial Sequence
<220>   FEATURE:
<223>   OTHER INFORMATION: Oligonucleotide
<400>   SEQUENCE: 185
        aataggattg cgctgttatc                                           20

<210>   SEQ ID NO 186
<211>   LENGTH: 20
<212>   TYPE: DNA
<213>   ORGANISM: Artificial Sequence
```

| SEQUENCES |
|---|
| <220> FEATURE:<br><223> OTHER INFORMATION: Oligonucleotide<br><400> SEQUENCE: 186<br>attgttgata tggactctag 20<br><br><210> SEQ ID NO 187<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 187<br>atccaacatc gaggtcgtaa 20<br><br><210> SEQ ID NO 188<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 188<br>gcggctgcac catcgggat 19<br><br><210> SEQ ID NO 189<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 189<br>ttgaacaaac gaacctttta 19<br><br><210> SEQ ID NO 190<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 190<br>aactcagatc acgtaggact 20<br><br><210> SEQ ID NO 191<br><211> LENGTH: 19<br><212> TYPE: DNA<br><213> ORGANISM: Artificial Sequence<br><220> FEATURE:<br><223> OTHER INFORMATION: Oligonucleotide<br><400> SEQUENCE: 191<br>aaaccgacct ggattactc 19<br><br><210> SEQ ID NO 192<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 192<br>agggaggaat ttgaaggtag 20<br><br><210> SEQ ID NO 193<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 193<br>ggccttattt ctcttgtcct 20<br><br><210> SEQ ID NO 194<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 194<br>ggaaggcgct ttgtgaagta 20 |

| SEQUENCES |
|---|
| <210> SEQ ID NO 195<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 195<br>aagttgagat gatatcattt 20 |
| <210> SEQ ID NO 196<br><211> LENGTH: 17<br><212> TYPE: DNA<br><213> ORGANISM: Artificial Sequence<br><220> FEATURE:<br><223> OTHER INFORMATION: Oligonucleotide<br><400> SEQUENCE: 196<br>cctgttcttg ggtgggt 17 |
| <210> SEQ ID NO 197<br><211> LENGTH: 18<br><212> TYPE: DNA<br><213> ORGANISM: Artificial Sequence<br><220> FEATURE:<br><223> OTHER INFORMATION: Oligonucleotide<br><400> SEQUENCE: 197<br>gtcctaaact accaaacc 18 |
| <210> SEQ ID NO 198<br><211> LENGTH: 20<br><212> TYPE: DNA<br><213> ORGANISM: Artificial Sequence<br><220> FEATURE:<br><223> OTHER INFORMATION: Oligonucleotide<br><400> SEQUENCE: 198<br>caccctctaa cctagagaag 20 |
| <210> SEQ ID NO 199<br><211> LENGTH: 18<br><212> TYPE: DNA<br><213> ORGANISM: Artificial Sequence<br><220> FEATURE:<br><223> OTHER INFORMATION: Oligonucleotide<br><400> SEQUENCE: 199<br>aggtggagtg gattgggg 18 |
| <210> SEQ ID NO 200<br><211> LENGTH: 2374<br><212> TYPE: RNA<br><213> ORGANISM: Homo sapiens<br><400> SEQUENCE: 200 |
| 60   ucuaauacug gugaugcuag aggugauguu uuugguaaac aggcggggua agauuugccg |
| 120  aguccuuuu acuuuuuua accuuuccuu augagcaugc cuguguuggg uugacaguga |
| 180  ggguaauaau gacuuguugg uugauuguag auauugggcu guuaauuguc aguucagugu |
| 240  uuuaaucuga cgcaggcuua ugcggaggag aauguuuuca uguuacuuau acuaacauua |
| 300  guucuucuau agggugauag auugguccaa uugggugugu ggaguucagu uauauguuug |
| 360  ggauuuuuua gguaguggu guugagcuug aacgcuuucu uaauuggugg cugcuuuuag |
| 420  gccuacuaug ggguguuaaau uuuuuacucu cucuacaagg uuuuuuccua guguccaaag |
| 480  agcuguuccu cuuuggacua acaguuaaau uuacaagggg auuuagaggg uucuguggc |
| 540  aaauuuaaag uugaacuaag auucuaucuu ggacaaccag cuauaccag gcucgguagg |
| 600  uuugucgccu cuaccuauaa aucucccac uauuuugcua cauagacggg ugugcucuuu |
| 660  uagcuguucu uagguagcuc gucuggduuc ggggucuua gcuuggcuc uccuugcaaa |
| 720  guuauuucua guuaauucau uaugcagaag guauagggu uagccuugc uauauuaugc |
| 780  uugguuauaa uuuucaucu uucccuugcg guacuauauc uauugcgcca gguucaauu |
| 840  ucuaucgccu auacuuuauu ugggauaaaug guuuggcuaa accuagcccc aaacccacuc |

| SEQUENCES | |
|---|---|
| 900 | caccuuacua ccagacaacc uuagccaaac cauuuaccca aauaaaguau aggcgauaga |
| 960 | aauugaaacc uggcgcaaua gauauaguac cgcaagggaa agaugaaaaa uuauaaccaa |
| 1020 | gcauaauaua gcaaggacua accccuauac cuucugcaua augaauuaac uagaaauaac |
| 1080 | uuugcaagga gagccaaagc uaagaccccc gaaaccagac gagcuaccua agaacagcua |
| 1140 | aaagagcaca cccgucuaug uagcaaaaua gugggaagau uuauagguag aggcgacaaa |
| 1200 | ccuaccgagc cuggugauag cugguuqucc aagauagaau cuuaguucaa cuuuaaauuu |
| 1260 | gcccacagaa cccucuaaau ccccuuguaa auuuaacugu uagaccaaag aggaacagcu |
| 1320 | cuuuggacac uaggaaaaaa ccuuguagag agaguaaaaa auuuaacacc cauaguaggc |
| 1380 | cuaaaagcag ccaccaauua agaaagcguu caagcucaac acccacuacc uaaaaaaucc |
| 1440 | caaacauaua acugaacucc ucacacccaa uuggaccaau cuaucacccu auagaagaac |
| 1500 | uaauguuagu auaaguaaca ugaaaacauu cuccuccgca uaagccugcg ucagauuaaa |
| 1560 | acacugaacu gacaauuaac agcccaauau cuacaaucaa ccaacaaguc auuauuaccc |
| 1620 | ucacgucaa cccaacacag gcaugcucau aaggaaaggu uaaaaaaagu aaaaggaacu |
| 1680 | cggcaaaucu accccgccu guuuaccaaa aacaucaccu cuagcaucac caguauuaga |
| 1740 | ggcaccgccu gcccagugac acauguuuaa cggccgcggu acccuaaccg ugcaaaggua |
| 1800 | gcauaaucac uuguuccuua aauagggacc uguaugaaug cuccacgag gguucagcug |
| 1860 | ucucuuacuu uuaaccagug aaauugaccu gcccgugaag aggcgggcau aacacagcaa |
| 1920 | gacgagaaga cccauaggag cuuuaauuua uuaaugcaaa caguaccuaa caaacccaca |
| 1980 | gguccuaaac uaccaaaccu gcauuaaaaa uuucgguugg ggcgaccucg gagcagaacc |
| 2040 | caaccuccga gcaguacaug cuaagacuuc accagucaaa gcgaacuacu auacucaauu |
| 2100 | gauccaauaa cuugaccaac ggaacaaguu acccuaggga uaacagcgca auccuauucu |
| 2160 | agaguccaua ucaacaauag gguuuacgac cucgauguug gaucaggaca ucccgauggu |
| 2220 | gcagccgcua uuaaagguuc guuuguucaa cgauuaaagu ccuacgugau cugaguucag |
| 2280 | accggaguaa uccaggucgg uuucuaucua ccuucaaauu ccucccugua cgaaaggaca |
| 2340 | agagaaauaa ggccuacuuc acaaagcgcc uucccccgua aaugauauca cucaacuua |
| 2374 | guauuauacc cacacccacc caagaacagg guuu |

<210> SEQ ID NO 201
<211> LENGTH: 1679
<212> TYPE: RNA
<213> ORGANISM: Homo saiens
<400> SEQUENCE: 201

| | |
|---|---|
| 60 | ggggucuuag cuuuggcucu ccuugcaaag uuauuucuag uuaauucauu augcagaagg |
| 120 | uauaggdggu aguccuugcu auauuaugcu ugguuauaau uuucaucuu ucccuugcgg |
| 180 | ugcuaaaccu agccccaaac ccacuccacc uuacuaccag acaaccuuag ccaaaccauu |
| 240 | uacccaaaua aaguauaggc gauagaaauu gaaaccuggc gcaauagaua uaguaccgca |
| 300 | agggaaagau gaaaauuau aaccaagcau aauauagcaa ggacuaaccc cuauaccuuc |
| 360 | ugcauaauga uuaacuaga aauaacuuug caaggagagc caaagcuaag accccgaaa |
| 420 | ccagacgagc uaccaagaa cagcuaaaag agcacacccg ucuauguagc aaaauagugg |
| 480 | gaagauuuau agguagaggc gacaaaccua ccgagccugg ugauagcugg uuguccaaga |
| 540 | uagaaucuua guucaacuuu aaauugccc acagacccu cuaaucccc uguaaauuuu |
| 600 | aacuguuagu ccaaagagga acagcucuuu ggacacuagg aaaaaaccuu guagagagag |

| SEQUENCES |
|---|
| 660 uaaaaaauuu aacacccaua guaggccuaa aagcagccac caauuaagaa agcguucaag |
| 720 cucaacaccc acuaccuaaa aaaucccaaa cauauaacug aaccucac acccaauugg |
| 780 accaaucuau cacccuauag aagaacuaau guuaguauaa guaacaugaa aacauucc |
| 840 uccgcauaag ccugcgucag auuaaaacac ugaacugaca auuaacagcc caauaucuac |
| 900 aaucaaccaa caagucauua uacccucac ugucaaccca acacaggcau gcucauaagg |
| 960 aaagguuaaa aaaaguaaaa ggaacucggc aaaucuuacc ccgccuguuu accaaaaaca |
| 1020 ucaccucuag caucaccagu auuagaggca ccgccugccc agugacacau guuaacggc |
| 1080 cgcgguaccc uaaccgugca aagguagcau aaucacuugu ccuuaaaua gggaccugua |
| 1140 ugaauggcuc cacgagggu cagcugucuc uuacuuuaa ccagugaaau ugaccugccc |
| 1200 gugaagaggc gggcauaaca cagcaagacg agaagacccu auggagcuuu aauuuauuaa |
| 1260 ugcaaacagu accuaacaaa cccacagguc cuaaacuacc aaaccugcau uaaaaauuuc |
| 1320 gguugggcg accucggagc agaacccaac cuccgagcag uacaugcuaa gacuucacca |
| 1380 gucaaagcga acuacuauac ucaauugauc caauaacuug accaacgaa caaguuaccc |
| 1440 uagggauaac agcgcaaucc uauucuagag uccauaucaa caauggguu uacgaccucg |
| 1500 auguuggauc aggacauccc aauggugcag ccgcuauuaa agguucguu guucaacgau |
| 1560 uaaaguccua cgugaucuga guucagaccg gaguaaucca ggucgguuuc uaucuacuuc |
| 1620 aaauuccucc cuguacgaaa ggacaagaga aauaaggccu acuucacaaa gcgccuuccc |
| 1679 ccguaaauga uaucaucuca acuuaguauu auacccacac ccacccaaga cagggguuu |
| <210> SEQ ID NO 202 |
| <211> LENGTH: 1635 |
| <212> TYPE: RNA |
| <213> ORGANISM: Homo sapiens |
| <400> SEQUENCE: 202 |
| 60 ggggucuuag cuuuggcucu ccuugcaaag uuauuucuag uuaauucauu augcagaagg |
| 120 uauaggggu aguccuugcu aaaccuagcc ccaaacccac uccaccuuac uaccagacaa |
| 180 ccuuagccaa accauuuacc caaauaaagu auaggcgaua gaaauugaaa ccuggcgcaa |
| 240 uagauauagu accgcaaggg aaagaugaaa aauuauaacc aagcauaaua uagcaaggac |
| 300 uaacccuau accuucugca uaaugaauua acuagaaaua acuuugcaag gagagccaaa |
| 360 gcuaagaccc ccgaaaccag acgagcuacc uaagaacagc uaaagagca caccgucua |
| 420 uguagcaaaa uagugggaag auuuauaggu agaggcgaca aaccuaccga gccggugau |
| 480 agcugguugu ccaagauaga aucuuaguuc aacuuuaaau uugcccacag aacccucuaa |
| 540 auccccuugu aaauuuaacu guuaguccaa agaggaacag cucuuuggac acuaggaaaa |
| 600 aaccuuguag agaguaaaa aaauuuaaca cccauaguag gccuaaaagc agccaccaau |
| 660 uaagaaagcg uucaagcuca acacccacua ccuaaaaaau cccaaacaua uaacugaacu |
| 720 ccucacacc aauuggacca aucuaucacc cuauagaaga acuaauguua guauaaguaa |
| 780 caugaaaaca uucccuccg cauaagccug cgucagauua aaacacugaa cugacaauua |
| 840 acagcccaau aucuacaauc aaccaacaag ucauuauuac ccucacuguc aacccaacac |
| 900 aggcaugcuc auaaggaaag guuaaaaaaa guaaaggaa cucggcaaau cuuacccgc |
| 960 cuguuuacca aaaacaucac cucuagcauc accaguauua gaggcaccgc cugcccagug |
| 1020 acacauguuu aacggccgcg guacccuaac cgugcaaagg uagcauaauc acuuguccu |
| 1080 uaaauaggga ccuguaugaa uggcuccacg aggguucagc ugucucuuac uuuuaaccag |

| SEQUENCES |
|---|
| 1140  ugaaauugac cugcccguga agaggcgggc auaacacagc aagacgagaa gacccuaugg |
| 1200  agcuuuaauu uauuaaugca aacaguaccu aacaaaccca cagguccuaa acuaccaaac |
| 1260  cugcauuaaa aauuucgguu ggggcgaccu cggagcagaa cccaaccucc gagcaguaca |
| 1320  ugcuaagacu ucaccaguca aagcgaacua cuauacucaa uugauccaau aacuugacca |
| 1380  acggaacaag uuacccuagg gauaacagcg caauccuauu cuagagucca uaucaacaau |
| 1440  aggguuuacg accucgaugu uggaucagga caucccaaug gugcagccgc uauuaaaggu |
| 1500  ucguuuguuc aacgauuaaa guccuacgug aucgaguuc agaccggagu aauccagguc |
| 1560  gguuucuauc uacuucaaau uccucccugu acgaaaggac aagagaaaua aggccuacuu |
| 1620  cacaaagcgc cuuccccgu aaaugauauc aucaacuu aguauuauac ccacacccac |
| 1635  ccaagaacag gguuu |

<210> SEQ ID NO 203
<211> LENGTH: 1921
<212> TYPE: RNA
<213> ORGANISM: Homo sapiens
<400> SEQUENCE: 203

| 60    aaccuccgag caguacaugc uaagacuuca ccagucaaag cgaacuacua uacucaauug |
|---|
| 120   auccaauaac uugaccaacg gaacaaguua cccuagggau aacagcgcaa uccuauucua |
| 180   gaguccauau caacaauagg guuuacgacc ucgauguugg aucaggacau cccaaugguug |
| 240   cagccgcuau uaagguucg uuuguuaaac gauuaaaguc cuacgugauc ugaguucaga |
| 300   ccggaguaau ccaggucggu ucuaucuac uucaaauucc ucccuguacg aaaggacaag |
| 360   agaaauaagg ccacuucac aaagcgccuu ccccguaaa ugauaucauc ucaacuuagu |
| 420   auuaucccu guucugggu gggugugggu auaauacuaa guugagauga uaucauuuac |
| 480   ggggaaggc gcuugugaa guaggccuua uuucucuugu ccuucguac agggaggaau |
| 540   uugaaguaga uagaaaccga ccuggauuac uccggucuga acucagauca cguaggacuu |
| 600   uaaucguuga caaacgaac cuuuaauagc ggcugcacca ucgggaugu cugauccaac |
| 660   aucgaggucg uaaacccuau uguugauaug gacucuagaa uaggauugc cuguuauccc |
| 720   uaggguaacu uguuccguug gucaaguuau uggaucaauu gaguauagua guucgcuuug |
| 780   acuggugaag ucuuagcaug uacugcucgg agguuggguu cugcuccgag gucgccccaa |
| 840   ccgaaauuuu uaaugcaggu uugguaguuu aggaccugug gguuuguuag guacuguuug |
| 900   cauuaauaaa uuaaagcucc uaagggucuu cucgucugc uguguuaugc ccgccucuuc |
| 960   acgggcaggu caauuucacu gguuaaaagu aagagacagc ugaacccucg uggagccauu |
| 1020  cauacagguc ccuauuuaag gaacaaguga uuaugcuacc uuugcacggu uagggauccg |
| 1080  cggccguuaa acauguguca cugggcaggc ggugccucua auacggguga ugcuagaggu |
| 1140  gauguuuug guaaacaggc ggguaagau uugccgaguu ccuuuuacuu uuuuuaaccu |
| 1200  uuccuuauga gcaugccugu guuggguuga cagugagggu aauaaugacu uguugguuga |
| 1260  uuguagauau ugggcuguua auugucaguu caguguuuua aucugacgca ggcuuaugcg |
| 1320  gaggagaaug uuuucauguu acuuauacua acauuaguuc uucuauaggu ugauagauug |
| 1380  guccaauugg gugugaggag uucaguuaua uguugggau uuuuagguga uggggguguug |
| 1440  agcuugaacg cuuucuuaau uggugggcugc uuuuaggccu acuaugggug uuaauuuuu |
| 1500  uacucucucu acaagguuuu uuccuagugu ccaaagagcu guccucuuu ggacuaacag |
| 1560  uuaaauuuac aaggggauuu agagggguucu gugggcaaau uuaaaguuga acuaagauuc |

SEQUENCES

| | |
|---|---|
| 1620 | uaucuuggac aaccagcuau caccaggcuc gguagguuug ucgccucuac cuauaaaucu |
| 1680 | ucccacuauu uugcuacaua dacgggugug cucuuuuagc uguucuuagg uagcucgucu |
| 1740 | gguuucgggg gucuuagcuu uggcucuccu ugcaaaguua uuucaguua auucauuaug |
| 1800 | cagaagguau aggggguuagu ccuugcuaua uuaugcuugg uuauaauuuu ucaucuuucc |
| 1860 | cuugcgguac uauaucuauu gcgccagguu ucaauuucua ucgccuauac uuuauuuggg |
| 1920 | uaaaugguuu ggcuaagguu gucgguagu aaggugagu gggguugggg cuagguuuag |
| 1921 | c |

<210> SEQ ID NO 204
<211> LENGTH: 1744
<212> TYPE: RNA
<213> ORGANISM: Homo sapiens
<400> SEQUENCE: 204

| | |
|---|---|
| 60 | uagggauaac agcgcaaucc uauucagag uccauaucaa caauagggu uacgaccucg |
| 120 | auguuggauc aggacauccc gauggugcag ccgcuauuaa agguucguuu guucaacgau |
| 180 | uaaaguccua cgugaucuga guucagaccg gaguaauucca ggucgguuuc uaucuaccuu |
| 240 | caaauuccuc ccuguucuug gguggggugu gguauaauac uaaguugaga ugauaucauu |
| 300 | uacgggggaa ggcgcuuugu gaaguaggcc uuauucucu uguccuuucg uacagggagg |
| 360 | aauuugaagu agauagaaac cgaccuggau uacuccgguc ugaacucaga ucacguagga |
| 420 | cuuuaaucgu ugaacaaacg aaccuuuaau agcggcugca ccaucgggau guccugaucc |
| 480 | aacaucgagg ucguaaaccc uauuguugau auggacucua gaauaggauu gcgcuguuau |
| 540 | cccuagggua acuuguuccg uuggucaagu uauuggauca auugaguaua guagguucgcu |
| 600 | uugacugguug aagcuuagc auguacugcu cggagguugg guucugcucc gaggucgccc |
| 660 | caaccgaaau uuuuaaugca gguugguag uuuaggaccu guggguuugu aagguacugu |
| 720 | uugcauuaau aaauuaaagc uccauagggu cuucgucucu ugcuguguua ugcccgccuc |
| 780 | uucacgggca ggucaauuuc acugguuaaa aguaagagac agcugaaccc ucgggagcc |
| 840 | auucauacag gucccuauuu aaggaacaag ugauuaugcu accuuugcac gguuagggua |
| 900 | ccgcggccgu uaaacauguug ucacgggca ggcggugccu cuaauacugg ugaugcuaga |
| 960 | ggugauguuu uugguaaaca ggcgggguaa gauuugccga guuccuuuua cuuuuuuaa |
| 1020 | ccuuuccuua ugagcaugcc uguguugggu ugacagugag gguaauaaug acuuguuggu |
| 1080 | ugauuguaga uauugggcug uuaaauguca guucaguguu uuaaucugac gcaggcuuau |
| 1140 | gcggaggaga auguuucau guuacuuaua cuaacauuag uucuucuaua gggugauaga |
| 1200 | uugguccaau ugggugugag gaguucaguu auauguuugg gauuuuuag guaguggugu |
| 1260 | uugagcuuga acgcuuucuu aauuggugg ucguuuuagg ccuacuaugg uguuaaauu |
| 1320 | uuuuacucuc ucuacaaggu uuuuccuag uguccaaaga gcuguccuc uuuggacuaa |
| 1380 | caguuaaauu uacaagggga uuuagagggu ucuguggggca aauuuaaagu ugaacuaaga |
| 1440 | uucuaucuug dacaaccagc uaucaccagg cucgguaggu uugucgccuc uaccuauaaa |
| 1500 | ucuucccacu auuuugcuac auagacgggu gugcucuuuu agcuguucu agguagcucg |
| 1560 | ucugguuucg ggggucuuag cuuuggcucu ccuugcaaag uuauuucuag uuaauucauu |
| 1620 | augcagaagg uauagggggu uagccuugcu auauuaugcu ugguuauaau uuucaucuu |
| 1680 | ucccugcgg uacuauaucu auugcgccag guucaauuu cuaucgccua uacuuuauuu |
| 1740 | ggguaaaugg uuuggcuaag guugucuggu aguaaggugg aguggguuug gggcuagguu |

SEQUENCES 1744  uagc

<210>  SEQ ID NO 205
<211>  LENGTH: 1854
<212>  TYPE: RNA
<213>  ORGANISM: Homo sapiens
<400>  SEQUENCE: 205

```
  60  gaacucggca aaucuuaccc cgccuguuua ccaaaaacau caccucuagc aucaccagua
 120  uuagaggcac cgccugccca gugacacaug uuuaacggcc gcgguacccu aaccgugcaa
 180  agguagcaua aucacuuguu ccuuaaauag ggaccuguau gaauggcucc acgaggguuc
 240  agcugucucu acuuuuaac cagugaaauu gaccugcccg ugaagaggcg ggcaugacac
 300  agcaagacga gaagacccua uggagcuuua auuauuaau gcaaacagua ccuaacaaac
 360  ccuguucuug ggugguguug gguauaauac uaaguugaga ugauaucauu uacggggggaa
 420  ggcgcuuugu gaaguaggcc uuauuucucu uguccuuucg uacagggagg aauuugaagu
 480  agauagaaac cgaccuggau uacuccgguc ugaacucaga ucacguagga cuuuaaucgu
 540  ugaacaaacg aaccuuuaau agcggcugca ccaucgggau guccugaucc aacaucgagg
 600  ucguaaaccc uauuguugau auggacucua gaauaggauu gcgcuguuau cccaggguua
 660  acuuguuccg uuggucaagu uauggauca auugaguaua guaguucgcu uugacgguggu
 720  aagucuuagc auguacugcu cggaggutugg guucugcucc gaggucgccc caaccgaaau
 780  uuuuaaugca gguuggguag uuuaggaccu guggguutugu uaggacugu uugcauuaau
 840  aaauuaaagc uccauagggu cuucucgucu ugcuguguua ugcccgcccuc uucacgggca
 900  ggucaauuuc acugguuaaa aaaagagac agcugaaccc ucguggagcc auucauacag
 960  gucccuauuu aaggaacaag ugauuaugcu accuugcac gguagggua ccgcggccgu
1020  uaaacaugug ucacugggca ggcggugccu cuaauacugg ugaugcuaga ggugauguuu
1080  uugguaaaaca ggcgggguaa gauuugccga guuccuuuua cuuuuuuaa ccuuuccuua
1140  ugagcaugcc uguguuggggu ugacagugag gguaauaaug acuguuggu ugauuguaga
1200  uauugggcug uuaauuguca guucagguguu uuaaucugac gcaggcuuau gcggaggaga
1260  auguuuucau guuacuuaua cuaacauuag uucuucuaua ggugauaga uuggccaau
1320  uggggugugag gaguucaguu auauguuugg gauuuuuuag guagugggug uugagcuuga
1380  acgcuuucuu aauuggugge ugcuuuuagg ccuacuaugg guguuaaauu uuuuacucuc
1440  ucuacaaggu uuuuccuag uguccaaaga gcuguccuc uuuggacuaa caguuaaauu
1500  uacaagggga uuuagagggu ucuguggggca aauuuaaagu ugaacuaaga uucuaucuug
1560  gacaaccagc uaucaccagg cucgguaggu uugucgccuc uaccuauaaa ucuucccacu
1620  auuuugcuac auagacgggu gugcucuuuu agcuguucuu agguagcucg ucugguuucg
1680  ggggucuuag cuuuggcucu ccuugcaaag uuauuucuag uuaauucauu augcagaagg
1740  uauaggggguu agccuugcu auauuaugcu ugguuauaau uuucaucuu ucccuugcgg
1800  uacuauaucu auugcgccag guucaauuu cuaucgccua acuuauuu ggguaaaugg
1854  uuuggcuaag guugucuggu aguaaggugg agugggguug gggcuagguu uagc
```

SEQUENCE LISTING

<160>  NUMBER OF SEQ ID NOS: 205

<210> SEQ ID NO 1
<211> LENGTH: 2374
<212> TYPE: DNA
<213> ORGANISM: Homo sapiens

<400> SEQUENCE: 1

| | | | | | |
|---|---|---|---|---|---|
| tctaatactg | gtgatgctag | aggtgatgtt | tttggtaaac | aggcggggta | agatttgccg | 60 |
| agttcctttt | acttttttta | acctttcctt | atgagcatgc | ctgtgttggg | ttgacagtga | 120 |
| gggtaataat | gacttgttgg | ttgattgtag | atattgggct | gttaattgtc | agttcagtgt | 180 |
| tttaatctga | cgcaggctta | tgcggaggag | aatgttttca | tgttacttat | actaacatta | 240 |
| gttcttctat | agggtgatag | attggtccaa | ttgggtgtga | ggagttcagt | tatatgtttg | 300 |
| ggatttttta | ggtagtgggt | gttgagcttg | aacgctttct | taattggtgg | ctgcttttag | 360 |
| gcctactatg | ggtgttaaat | tttttactct | ctctacaagg | ttttttccta | gtgtccaaag | 420 |
| agctgttcct | ctttggacta | acagttaaat | ttacaagggg | atttagaggg | ttctgtgggc | 480 |
| aaatttaaag | ttgaactaag | attctatctt | ggacaaccag | ctatcaccag | gctcggtagg | 540 |
| tttgtcgcct | ctacctataa | atcttccac | tattttgcta | catagacggg | tgtgctcttt | 600 |
| tagctgttct | taggtagctc | gtctggtttc | ggggtctta | gctttggctc | tccttgcaaa | 660 |
| gttatttcta | gttaattcat | tatgcagaag | gtatagggt | tagtccttgc | tatattatgc | 720 |
| ttggttataa | tttttcatct | ttcccttgcg | gtactatatc | tattgcgcca | ggtttcaatt | 780 |
| tctatcgcct | atactttatt | tgggtaaatg | gtttggctaa | acctagcccc | aaacccactc | 840 |
| caccttacta | ccagacaacc | ttagccaaac | catttaccca | aataaagtat | aggcgataga | 900 |
| aattgaaacc | tggcgcaata | gatatagtac | cgcaagggaa | agatgaaaaa | ttataaccaa | 960 |
| gcataatata | gcaaggacta | acccctatac | cttctgcata | atgaattaac | tagaaataac | 1020 |
| tttgcaagga | gagccaaagc | taagaccccc | gaaaccagac | gagctaccta | agaacagcta | 1080 |
| aaagagcaca | cccgtctatg | tagcaaaata | gtgggaagat | ttataggtag | aggcgacaaa | 1140 |
| cctaccgagc | ctggtgatag | ctggttgtcc | aagatagaat | cttagttcaa | ctttaaattt | 1200 |
| gcccacagaa | ccctctaaat | cccttgtaa | atttaactgt | tagtccaaag | aggaacagct | 1260 |
| ctttggacac | taggaaaaaa | ccttgtagag | agagtaaaaa | atttaacacc | catagtaggc | 1320 |
| ctaaaagcag | ccaccaatta | agaaagcgtt | caagctcaac | acccactacc | taaaaaatcc | 1380 |
| caaacatata | actgaactcc | tcacacccaa | ttggaccaat | ctatcaccct | atagaagaac | 1440 |
| taatgttagt | ataagtaaca | tgaaaacatt | ctcctccgca | taagcctgcg | tcagattaaa | 1500 |
| acactgaact | gacaattaac | agcccaatat | ctacaatcaa | ccaacaagtc | attattaccc | 1560 |
| tcactgtcaa | cccaacacag | gcatgctcat | aaggaaaggt | taaaaaaagt | aaaggaact | 1620 |
| cggcaaatct | taccccgcct | gtttaccaaa | aacatcacct | ctagcatcac | cagtattaga | 1680 |
| ggcaccgcct | gcccagtgac | acatgtttaa | cggccgcgt | accctaaccg | tgcaaaggta | 1740 |
| gcataatcac | ttgttccta | aatagggacc | tgtatgaatg | gctccacgag | ggttcagctg | 1800 |
| tctcttactt | ttaaccagtg | aaattgacct | gcccgtgaag | aggcgggcat | aacacagcaa | 1860 |
| gacgagaaga | ccctatggag | ctttaattta | ttaatgcaaa | cagtacctaa | caaacccaca | 1920 |
| ggtcctaaac | taccaaacct | gcattaaaaa | tttcggttgg | ggcgacctcg | gagcagaacc | 1980 |
| caacctccga | gcagtacatg | ctaagacttc | accagtcaaa | gcgaactact | atactcaatt | 2040 |
| gatccaataa | cttgaccaac | ggaacaagtt | accctaggga | taacagcgca | atcctattct | 2100 |
| agagtccata | tcaacaatag | ggtttacgac | ctcgatgttg | gatcaggaca | tcccgatggt | 2160 |

```
gcagccgcta ttaaaggttc gtttgttcaa cgattaaagt cctacgtgat ctgagttcag    2220
accggagtaa tccaggtcgg tttctatcta ccttcaaatt cctccctgta cgaaaggaca    2280
agagaaataa ggcctacttc acaaagcgcc ttccccgta aatgatatca tctcaactta    2340
gtattatacc cacacccacc caagaacagg gttt                                2374

<210> SEQ ID NO 2
<211> LENGTH: 1679
<212> TYPE: DNA
<213> ORGANISM: Homo sapiens

<400> SEQUENCE: 2
ggggtcttag ctttggctct ccttgcaaag ttatttctag ttaattcatt atgcagaagg      60
tataggggtt agtccttgct atattatgct tggttataat ttttcatctt tcccttgcgg     120
tgctaaacct agccccaaac ccactccacc ttactaccag acaaccttag ccaaaccatt     180
tacccaaata agtataggc gatagaaatt gaaacctggc gcaatagata tagtaccgca     240
agggaaagat gaaaaattat aaccaagcat aatatagcaa ggactaaccc ctataccttc     300
tgcataatga attaactaga ataactttg caaggagagc caaagctaag accccgaaa      360 ccagacgagc tacctaagaa cagctaaaag agcacacccg tctatgtagc aaaatagtgg     420
gaagatttat aggtagaggc gacaaaccta ccgagcctgg tgatagctgg ttgtccaaga    480
tagaatctta gttcaacttt aaatttgccc acagaaccct ctaaatcccc ttgtaaattt     540
aactgttagt ccaaagagga acagctcttt ggacactagg aaaaaaccctt gtagagagag     600 taaaaaattt aacacccata gtaggcctaa aagcagccac caattaagaa agcgttcaag    660
ctcaacaccc actacctaaa aaatcccaaa catataactg aactcctcac acccaattgg     720
accaatctat caccctatag aagaactaat gttagtataa gtaacatgaa acattctcc     780 tccgcataag cctgcgtcag attaaaacac tgaactgaca attaacagcc caatatctac    840
aatcaaccaa caagtcatta ttaccctcac tgtcaaccca acacaggcat gctcataagg    900
aaaggttaaa aaaagtaaaa ggaactcggc aaatcttacc ccgcctgttt accaaaaaca    960
tcacctctag catcaccagt attagaggca ccgcctgccc agtgacacat gtttaacggc    1020
cgcggtaccc taaccgtgca aaggtagcat aatcacttgt tccttaaata gggacctgta    1080
tgaatggctc cacgagggtt cagctgtctc ttacttttaa ccagtgaaat tgacctgccc    1140
gtgaagaggc gggcataaca cagcaagacg agaagaccct atggagcttt aatttattaa    1200
tgcaaacagt acctaacaaa cccacaggtc ctaaactacc aaacctgcat taaaaatttc    1260
ggttggggcg acctcggagc agaacccaac ctccgagcag tacatgctaa gacttcacca    1320
gtcaaagcga actactatac tcaattgatc caataacttg accaacggaa caagttaccc    1380
tagggataac agcgcaatcc tattctagag tccatatcaa caatagggtt tacgacctcg    1440
atgttggatc aggacatccc aatggtgcag ccgctattaa aggttcgttt gttcaacgat    1500
taaagtccta cgtgatctga gttcagaccg gagtaatcca ggtcggtttc tatctacttc    1560
aaattcctcc ctgtacgaaa ggacaagaga aataaggcct acttcacaaa gcgccttccc    1620
ccgtaaatga tatcatctca acttagtatt atacccacac ccacccaaga acagggttt    1679

<210> SEQ ID NO 3
<211> LENGTH: 1635
<212> TYPE: DNA
<213> ORGANISM: Homo sapiens
```

```
<400> SEQUENCE: 3
ggggtcttag ctttggctct ccttgcaaag ttatttctag ttaattcatt atgcagaagg    60
tataggggtt agtccttgct aaacctagcc ccaaacccac tccaccttac taccagacaa   120
ccttagccaa accatttacc caaataaagt ataggcgata gaaattgaaa cctggcgcaa   180
tagatatagt accgcaaggg aaagatgaaa aattataacc aagcataata tagcaaggac   240
taacccctat accttctgca taatgaatta actagaaata actttgcaag gagagccaaa   300
gctaagaccc ccgaaaccag acgagctacc taagaacagc taaaagagca cacccgtcta   360
tgtagcaaaa tagtgggaag atttataggt agaggcgaca aacctaccga gcctggtgat   420
agctggttgt ccaagataga atcttagttc aactttaaat ttgcccacag aaccctctaa   480
atccccttgt aaatttaact gttagtccaa agaggaacag ctctttggac actaggaaaa   540
aaccttgtag agagagtaaa aaatttaaca cccatagtag gcctaaaagc agccaccaat   600
taagaaagcg ttcaagctca cacccacta cctaaaaaat cccaaacata taactgaact   660
cctcacaccc aattggacca atctatcacc ctatagaaga actaatgtta gtataagtaa   720
catgaaaaca ttctcctccg cataagcctg cgtcagatta aaacactgaa ctgacaatta   780
acagcccaat atctacaatc aaccaacaag tcattattac cctcactgtc aacccaacac   840
aggcatgctc ataaggaaag gttaaaaaaa gtaaaggaa ctcggcaaat cttaccccgc   900
ctgtttacca aaaacatcac ctctagcatc accagtatta gaggcaccgc ctgcccagtg   960
acacatgttt aacggccgcg gtaccctaac cgtgcaaagg tagcataatc acttgttcct  1020 taaatagggaa cctgtatgaa tggctccacg agggttcagc tgtctcttac ttttaaccag  1080
tgaaattgac ctgcccgtga agaggcgggc ataacacagc aagacgagaa gacccctatgg 1140 agctttaatt tattaatgca aacagtacct aacaaaccca caggtcctaa actaccaaac  1200
ctgcattaaa aatttcggtt ggggcgacct cggagcagaa cccaacctcc gagcagtaca  1260
tgctaagact tcaccagtca aagcgaacta ctatactcaa ttgatccaat aacttgacca  1320
acggaacaag ttaccctagg ataacagcg caatcctatt ctagagtcca tatcaacaat  1380
agggtttacg acctcgatgt tggatcagga catcccaatg gtgcagccgc tattaaaggt  1440
tcgtttgttc aacgattaaa gtcctacgtg atctgagttc agaccggagt aatccaggtc  1500
ggtttctatc tacttcaaat tcctcccgt acgaaaggac aagagaaata aggcctactt  1560
cacaaagcgc cttccccgt aaatgatatc atctcaactt agtattatac ccacacccac  1620
ccaagaacag ggttt                                                   1635

<210> SEQ ID NO 4
<211> LENGTH: 1921
<212> TYPE: DNA
<213> ORGANISM: Homo sapiens

<400> SEQUENCE: 4
aacctccgag cagtacatgc taagacttca ccagtcaaag cgaactacta tactcaattg    60
atccaataac ttgaccaacg gaacaagtta ccctagggat aacagcgcaa tcctattcta   120
gagtccatat caacaatagg gtttacgacc tcgatgttgg atcaggacat cccaatggtg   180
cagccgctat taaaggttcg tttgttcaac gattaaagtc ctacgtgatc tgagttcaga   240
ccggagtaat ccaggtcggt ttctatctac ttcaaattcc tcccgtacg aaaggacaag   300 agaaataagg cctacttcac aaagcgcctt ccccgtaaa tgatatcatc tcaacttagt   360
attataccct gttcttgggt gggtgtgggt ataatactaa gttgagatga tatcatttac   420
```

```
ggggggaaggc gctttgtgaa gtaggcctta tttctcttgt cctttcgtac agggaggaat    480
ttgaagtaga tagaaaccga cctggattac tccggtctga actcagatca cgtaggactt    540
taatcgttga acaaacgaac ctttaatagc ggctgcacca tcgggatgtc ctgatccaac    600
atcgaggtcg taaaccctat tgttgatatg gactctagaa taggattgcg ctgttatccc    660
tagggtaact tgttccgttg gtcaagttat tggatcaatt gagtatagta gttcgctttg    720
actggtgaag tcttagcatg tactgctcgg aggttgggtt ctgctccgag gtcgccccaa    780
ccgaaatttt taatgcaggt ttggtagttt aggacctgtg ggtttgttag gtactgtttg    840
cattaataaa ttaaagctcc atagggtctt ctcgtcttgc tgtgttatgc ccgcctcttc    900
acgggcaggt caatttcact ggttaaaagt aagagacagc tgaaccctcg tggagccatt    960
catacaggtc cctatttaag gaacaagtga ttatgctacc tttgcacggt tagggtaccg   1020
cggccgttaa acatgtgtca ctgggcaggc ggtgcctcta atactggtga tgctagaggt   1080
gatgtttttg gtaaacaggc ggggtaagat ttgccgagtt cctttacttt ttttaacct    1140 ttccttatga gcatgcctgt gttgggttga cagtgagggt aataatgact tgttggttga   1200
ttgtagatat tgggctgtta attgtcagtt cagtgtttta atctgacgca ggcttatgcg   1260
gaggagaatg ttttcatgtt acttatacta acattagttc ttctataggg tgatagattg   1320
gtccaattgg gtgtgaggag ttcagttata tgtttgggat tttttaggta gtgggtgttg   1380
agcttgaacg ctttcttaat tggtggctgc ttttaggcct actatgggtg ttaaattttt   1440
tactctctct acaaggtttt ttcctagtgt ccaaagagct gttcctcttt ggactaacag   1500
ttaaatttac aaggggatt agagggttct gtgggcaaat ttaaagttga actaagattc    1560
tatcttggac aaccagctat caccaggctc ggtaggtttg tcgcctctac ctataaatct   1620
tcccactatt ttgctacata gacgggtgtg ctcttttagc tgttcttagg tagctcgtct   1680
ggtttcgggg gtcttagctt tggctctcct tgcaaagtta tttctagtta attcattatg   1740
cagaaggtat aggggttagt ccttgctata ttatgcttgg ttataatttt tcatctttcc   1800
cttgcggtac tatatctatt gcgccaggtt tcaatttcta tcgcctatac tttatttggg   1860
taaatggttt ggctaaggtt gtctggtagt aaggtggagt gggtttgggg ctaggtttag   1920
c                                                                  1921
```

<210> SEQ ID NO 5
<211> LENGTH: 1744
<212> TYPE: DNA
<213> ORGANISM: Homo sapiens

<400> SEQUENCE: 5

```
tagggataac agcgcaatcc tattctagag tccatatcaa caatagggtt tacgacctcg     60
atgttggatc aggacatccc gatggtgcag ccgctattaa aggttcgttt gttcaacgat    120
taaagtccta cgtgatctga gttcagaccg gagtaatcca ggtcggtttc tatctacctt    180
caaattcctc cctgttcttg ggtgggtgtg gtataatac taagttgaga tgatatcatt     240
tacgggggaa ggcgcttgt gaagtaggcc ttatttctct tgtcctttcg tacagggagg     300
aatttgaagt agatagaaac cgacctggat tactccggtc tgaactcaga tcacgtagga    360
ctttaatcgt tgaacaaacg aacctttaat agcggctgca ccatcgggat gtcctgatcc    420
aacatcgagg tcgtaaaccc tattgttgat atggactcta gaataggatt gcgctgttat    480
ccctagggta acttgttccg ttggtcaagt tattggatca attgagtata gtagttcgct    540
```

```
ttgactggtg aagtcttagc atgtactgct cggaggttgg gttctgctcc gaggtcgccc    600
caaccgaaat ttttaatgca ggtttggtag tttaggacct gtgggtttgt taggtactgt    660
ttgcattaat aaattaaagc tccatagggt cttctcgtct tgctgtgtta tgcccgcctc    720
ttcacgggca ggtcaatttc actggttaaa agtaagagac agctgaaccc tcgtggagcc    780
attcatacag gtccctattt aaggaacaag tgattatgct acctttgcac ggttagggta    840
ccgcggccgt taaacatgtg tcactgggca ggcggtgcct ctaatactgg tgatgctaga    900
ggtgatgttt ttggtaaaca ggcggggtaa gatttgccga gttccttta ctttttttaa    960 cctttcctta tgagcatgcc tgtgttgggt tgacagtgag ggtaataatg acttgttggt   1020
tgattgtaga tattgggctg ttaattgtca gttcagtgtt ttaatctgac gcaggcttat   1080
gcggaggaga atgttttcat gttacttata ctaacattag ttcttctata gggtgataga   1140
ttggtccaat tgggtgtgag gagttcagtt atatgtttgg gattttttag gtagtgggtg   1200
ttgagcttga acgcttcctt aattggtggc tgcttttagg cctactatgg gtgttaaatt   1260
ttttactctc tctacaaggt ttttcctag tgtccaaaga gctgttcctc tttggactaa    1320
cagttaaatt tacaagggga tttagagggt tctgtgggca aatttaaagt tgaactaaga   1380
ttctatcttg gacaaccagc tatcaccagg ctcggtaggt ttgtcgcctc tacctataaa   1440
tcttcccact attttgctac atagacgggt gtgctctttt agctgttctt aggtagctcg   1500
tctggtttcg ggggtcttag cttggctct ccttgcaaag ttattctag ttaattcatt    1560 atgcagaagg tatagggggtt agtccttgct atattatgct tggttataat ttttcatctt   1620
tcccttgcgg tactatatct attgcgccag gtttcaattt ctatcgccta tactttattt   1680
gggtaaatgg tttggctaag gttgtctggt agtaaggtgg agtgggtttg gggctaggtt   1740
tagc                                                                1744

<210> SEQ ID NO 6
<211> LENGTH: 1854
<212> TYPE: DNA
<213> ORGANISM: Homo sapiens

<400> SEQUENCE: 6
gaactcggca atcttaccccc cgcctgttta ccaaaaacat cacctctagc atcaccagta     60
ttagaggcac cgcctgccca gtgacacatg tttaacggcc gcggtaccct aaccgtgcaa    120
aggtagcata atcacttgtt ccttaaatag ggacctgtat gaatggctcc acgagggttc    180
agctgtctct tacttttaac cagtgaaatt gacctgcccg tgaagaggcg ggcatgacac    240
agcaagacga aagaccccta tggagcttta atttattaat gcaaacagta cctaacaaac    300
cctgttcttg ggtgggtgtg gtataatac taagttgaga tgatatcatt tacgggggaa    360
ggcgctttgt gaagtaggcc ttatttctct tgtccttttcg tacagggagg aatttgaagt    420
agatagaaac cgacctggat tactccggtc tgaactcaga tcacgtagga ctttaatcgt    480
tgaacaaacg aaccttaat agcggctgca ccatcgggat gtcctgatcc aacatcgagg    540
tcgtaaaccc tattgttgat atggactcta gaataggatt gcgctgttat ccctagggta    600
acttgttccg ttggtcaagt tattggatca attgagtata gtagttcgct ttgactggtg    660
aagtcttagc atgtactgct cggaggttgg gttctgctcc gaggtcgccc caaccgaaat    720
ttttaatgca ggtttggtag tttaggacct gtgggtttgt taggtactgt ttgcattaat    780
aaattaaagc tccatagggt cttctcgtct tgctgtgtta tgcccgcctc ttcacgggca    840
ggtcaatttc actggttaaa agtaagagac agctgaaccc tcgtggagcc attcatacag    900
```

```
gtccctattt aaggaacaag tgattatgct acctttgcac ggttagggta ccgcggccgt    960
taaacatgtg tcactgggca ggcggtgcct ctaatactgg tgatgctaga ggtgatgttt   1020
ttggtaaaca ggcggggtaa gatttgccga gttccttta cttttttaa cctttcctta    1080 tgagcatgcc tgtgttgggt tgacagtgag ggtaataatg acttgttggt tgattgtaga   1140
tattgggctg ttaattgtca gttcagtgtt ttaatctgac gcaggcttat gcggaggaga   1200
atgttttcat gttacttata ctaacattag ttcttctata gggtgataga ttggtccaat   1260
tgggtgtgag gagttcagtt atatgtttgg gattttttag gtagtgggtg ttgagcttga   1320
acgctttctt aattggtggc tgcttttagg cctactatgg gtgttaaatt ttttactctc   1380
tctacaaggt ttttcctag tgtccaaaga gctgttcctc tttggactaa cagttaaatt    1440
tacaagggga tttagagggt tctgtgggca aatttaaagt tgaactaaga ttctatcttg   1500
gacaaccagc tatcaccagg ctcggtaggt ttgtcgcctc tacctataaa tcttcccact   1560
attttgctac atagacgggt gtgctctttt agctgttctt aggtagctcg tctggtttcg   1620
ggggtcttag ctttggctct ccttgcaaag ttatttctag ttaattcatt atgcagaagg   1680
tataggggtt agtccttgct atattatgct tggttataat ttttcatctt tcccttgcgg   1740
tactatatct attgcgccag gtttcaattt ctatcgccta actttatttt gggtaaatgg   1800
tttggctaag gttgtctggt agtaaggtgg agtgggtttg gggctaggtt tagc          1854

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
taggtttagc accgcaaggg                                                   20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
taggtttagc aaggactaac                                                   20

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 9
ggggtaagat ttgccgag                                                     18

<210> SEQ ID NO 10
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 10
```
atgctagagg tgatgttttt gg                                            22

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
cggtgcctct aatactgg                                                 18

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
gttaaacatg tgtcactggg                                               20

<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 13
ttgcacggtt agggtacc                                                 18

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 14
ggaacaagtg attatgctac c                                             21

<210> SEQ ID NO 15
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 15
ggagccattc atacaggtcc c                                             21

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
agtaagagac agctgaaccc                                               20

<210> SEQ ID NO 17
<211> LENGTH: 19
<212> TYPE: DNA
<213> ORGANISM: Artificial Sequence

```
<220> FEATURE:
<223> OTHER INFORMATION: Antisense Oligonucleotide

<400> SEQUENCE: 17
ggcaggtcaa tttcactgg                                                   19

<210> SEQ ID NO 18
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 18
gctgtgttat gcccgcctc                                                   19

<210> SEQ ID NO 19
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 19
agctccatag ggtcttctc                                                   19

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttaggtact gtttgcatta                                                  20

<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 21
aagtcttagc atgtactg                                                    18

<210> SEQ ID NO 22
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 22
tagtagttcg ctttgactg                                                   19

<210> SEQ ID NO 23
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 23
caagttattg gatcaattg                                                   19
```

```
<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 24
gggtaacttg ttccgttg                                             18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 25
aataggattg cgctgtta                                             18

<210> SEQ ID NO 26
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 26
cctattgttg atatggac                                             18

<210> SEQ ID NO 27
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 27
ctgatccaac atcgagg                                              17

<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 28
tagcggctgc accattgg                                             18

<210> SEQ ID NO 29
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 29
gttgaacaaa cgaaccttt                                            19

<210> SEQ ID NO 30
<211> LENGTH: 19
<212> TYPE: DNA
<213> ORGANISM: Artificial Sequence
<220> FEATURE:
<223> OTHER INFORMATION: Antisense Oligonucleotide
```

```
<400> SEQUENCE: 30
aactcagatc acgtaggac                                                19

<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 31
cgacctggat tactccgg                                                 18

<210> SEQ ID NO 32
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 32
ggaatttgaa gtagatag                                                 18

<210> SEQ ID NO 33
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 33
ctcttgtcct ttcgtacag                                                19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 34
ggcgctttgt gaagtagg                                                 18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 35
gttgagatga tatcatttac gg                                            22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 36
cacccaccca agaacagg                                                 18

<210> SEQ ID NO 37
```

<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 37
caacttagta ttatacccac accca                                           25

<210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 38
tcccccgtaa atgattacat ct                                              22

<210> SEQ ID NO 39
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 39
gagaaataag gcctacttca caaag                                           25

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 40
caaattcctc cctgtacgaa ag                                              22

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 41
agtaatccag gtcggtttct atct                                            24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 42
aagtcctagc tgatctgagt tcag                                            24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 43
gctattaaag gttcgtttgt tcaac                                              25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 44
tcccgatggt gcagcc                                                        16

<210> SEQ ID NO 45
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 45
ttacgacctc gatgttggat ca                                                 22

<210> SEQ ID NO 46
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 46
atcctattct agagtccata tcaac                                              25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 47
aataggattg cgctgttatc ccta                                               24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 48
tagggataac agcgcatacc tatt                                               24

<210> SEQ ID NO 49
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 49
ggaacaagtt accctaggga taa                                                23

<210> SEQ ID NO 50
<211> LENGTH: 23
<212> TYPE: DNA

```
<213> ORGANISM: Artificial Sequence
<220> FEATURE:
<223> OTHER INFORMATION: Antisense Oligonucleotide

<400> SEQUENCE: 50
ttgatccaat aacttgacca acg                                          23

<210> SEQ ID NO 51
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 51
acttcaccag tcaaagcgaa c                                            21

<210> SEQ ID NO 52
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 52
aacccaacct ccgagcag                                                18

<210> SEQ ID NO 53
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 53
gttggggcga cctcgg                                                  16

<210> SEQ ID NO 54
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 54
aaactaccaa acctgcttaa aa                                           22

<210> SEQ ID NO 55
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 55
aaacagtacc taacaaaccc acag                                         24

<210> SEQ ID NO 56
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 56
gaccctatgg agctttaatt tatta                                        25
```

<210> SEQ ID NO 57
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 57
cataacacag caagacgaga aga                                          23

<210> SEQ ID NO 58
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 58
tgacctgccc gtgaagag                                                18

<210> SEQ ID NO 59
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 59
cagctgtctc ttactttta ccagtg                                        26

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctgtatgaat ggctccacga                                              20

<210> SEQ ID NO 61
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 61
agcataatca cttgttcctt aaatag                                       26

<210> SEQ ID NO 62
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 62
accgtgcaaa ggtagcataa tca                                          23

<210> SEQ ID NO 63
<211> LENGTH: 23
<212> TYPE: DNA
<213> ORGANISM: Artificial Sequence
<220> FEATURE:

<223> OTHER INFORMATION: Antisense Oligonucleotide

<400> SEQUENCE: 63
tgattatgct acctttgcac ggt                                              23

<210> SEQ ID NO 64
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 64
gtaccctaac cgtgcaaag                                                   19

<210> SEQ ID NO 65
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 65
cctgcccagt gacacatgtt t                                                21

<210> SEQ ID NO 66
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 66
cacctctagc atcaccagta ttaga                                            25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cttaccccgc ctgtttacca                                                  20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 68
aggttaaaaa aagtaaaagg aactcg                                           26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 69
cccaacacag gcatgctca                                                   19

```
<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 70
accaacaagt cattattacc ctca                                          24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 71
tgacaattaa cagcccaata tcta                                          24

<210> SEQ ID NO 72
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 72
gcctgcgtca gattaaaaca c                                             21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 73
gtaacatgaa aacattctcc tccg                                          24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide

<400> SEQUENCE: 74
tatcacccta tagaagaact aatgttag                                      28

<210> SEQ ID NO 75
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 75
ctgaactcct cacacccaat t                                             21

<210> SEQ ID NO 76
<211> LENGTH: 23
<212> TYPE: DNA
<213> ORGANISM: Artificial Sequence
<220> FEATURE:
<223> OTHER INFORMATION: Antisense Oligonucleotide
```

```
<400> SEQUENCE: 76
cactacctaa aaaatcccaa aca                                              23

<210> SEQ ID NO 77
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 77
ttaagaaagc gttcaagctc a                                                21

<210> SEQ ID NO 78
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 78
catagtaggc ctaaaagcag c                                                21

<210> SEQ ID NO 79
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 79
aaaccttgta gagagagtaa aaaatt                                           26

<210> SEQ ID NO 80
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 80
aaagaggaac agctctttgg acac                                             24

<210> SEQ ID NO 81
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 81
aatccccttg taaatttaac tgtt                                             24

<210> SEQ ID NO 82
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 82
ctttaaattt gcccacagaa c                                                21

<210> SEQ ID NO 83
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 83
ggttgtccaa gatagaatct                                                  20

<210> SEQ ID NO 84
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 84
acaaacctac cgagcctgg                                                   19

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
aagatttata ggtagaggcg                                                  20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cccgtctatg tagcaaaata                                                  20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
acctaagaac agctaaaaga                                                  20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
taagaccccc gaaaccagac                                                  20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
```

```
ataactttgc aaggagagcc                                                        20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cttctgcata atgaattaac                                                        20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
atatagcaag gactaacccc                                                        20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agatgaaaaa ttataaccaa                                                        20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
caatagatat agtaccgcaa                                                        20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aggcgataga aattgaaacc                                                        20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tagccaaacc atttacccaa                                                        20

<210> SEQ ID NO 96
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 96
caccttacta ccagacaacc                                                  20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 97
ctaaacctag ccccaaacc                                                   19

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctagcatcac cagtattaga                                                  20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttaccaaaaa catcacctct                                                  20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gaactcggca aatcttaccc                                                  20

<210> SEQ ID NO 101
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 101
gggtaagatt tgccgagttc                                                  20

<210> SEQ ID NO 102
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 102
gctcataagg aaaggttaaa a                                                21
```

<210> SEQ ID NO 103
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 103
gtcaacccaa cacaggc                                                17

<210> SEQ ID NO 104
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 104
accaacaagt cattattacc c                                           21

<210> SEQ ID NO 105
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 105
ggttgattgt agatattggg ct                                          22

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
attaacagcc caatatctac                                             20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tgcgtcagat taaaacactg                                             20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
aaaacattct cctccgcata                                             20

<210> SEQ ID NO 109
<211> LENGTH: 18
<212> TYPE: DNA
<213> ORGANISM: Artificial Sequence
<220> FEATURE:
<223> OTHER INFORMATION: Antisense Oligonucleotide

```
<400> SEQUENCE: 109
gttagtataa gtaacatg                                                     18

<210> SEQ ID NO 110
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 110
tggaccaatc tatcaccct                                                    19

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
acatataact gaactcctca                                                   20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cacccactac ctaaaaaatc                                                   20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
caccaattaa gaaagcgttg                                                   20

<210> SEQ ID NO 114
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 114
taggcctaaa agcagccacc aa                                                22

<210> SEQ ID NO 115
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 115
ttggtggctg cttttaggcc ta                                                22

<210> SEQ ID NO 116
```

```
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 116
taacacccat agtaggcct                                              19

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
aaccttgtag agagagtaaa                                             20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
aacagctctt tggacactag                                             20

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 119
aactgttagt ccaaagag                                               18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 120
ctctaaatcc ccttgtaaa                                              19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 121
actttaaatt tgcccacag                                              19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 122
```

```
ggttgtccaa gatagaatc                                              19
```

<210> SEQ ID NO 123
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 123

```
acaaacctac cgagcctcc                                              19
```

<210> SEQ ID NO 124
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 124

```
atttataggt tagaggcg                                               18
```

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125

```
atgtagcaaa atagtgggaa                                             20
```

<210> SEQ ID NO 126
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 126

```
taagaacagc taaaagagca c                                           21
```

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 127

```
cgaaaccaga cgagctac                                               18
```

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 128

```
ggggtcttag ctttggctct cc                                          22
```

<210> SEQ ID NO 129
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 129
taactttgca aggagagcca                                               20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 130
accttctgca taatgaat                                                 18

<210> SEQ ID NO 131
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 131
atatagcaag gactaaccc                                                19

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gatgaaaaat tataaccaag                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
aatagatata gtaccgcaag                                               20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 134
cgatagaaat tgaaacc                                                  17

<210> SEQ ID NO 135
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 135
tactttattt gggtaaatgg                                               20
```

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ccatttaccc aaataaagta                                          20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ttagccaaac catttaccca                                          20

<210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 138
aaggtggagt gggtttgggg c                                        21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 139
gctaaggttg tctggta                                             17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
atcgcctata ctttatttgg                                          20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atctattgcg ccaggtttca                                          20

<210> SEQ ID NO 142
<211> LENGTH: 19
<212> TYPE: DNA
<213> ORGANISM: Artificial Sequence
<220> FEATURE:

<223> OTHER INFORMATION: Antisense Oligonucleotide

<400> SEQUENCE: 142
ttttcatctt tcccttgcg                                    19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tccttgctat attatgcttg                                   20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
cattatgcag aaggtatagg                                   20

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 145
tctccttgca aagttatt                                     18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
tttcgggggt cttagctttg                                   20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 147
ctgttcttag gtagctcg                                     18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 148
tgctacatag acgggtgtg                                    19

```
<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cctctaccta taaatcttcc                                            20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 150
gctatcacca ggctcgg                                               17

<210> SEQ ID NO 151
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 151
aagttgaact aagattc                                               17

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
gagggttctg tgggcaaatt                                            20

<210> SEQ ID NO 153
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 153
acagttaaat ttacaaggg                                             19

<210> SEQ ID NO 154
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 154
gtgtccaaag agctgttcc                                             19

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 155
tactctctct acaaggtttt                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
taggcctact atgggtgtta                                              20

<210> SEQ ID NO 157
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 157
aacgctttct taattggtgg c                                            21

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ttttaggtag tgggtgttga                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ggagttcagt tatatgtttg                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tgatagattg gtccaattgg                                              20

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 161
ctaacattag ttcttctata g                                            21

<210> SEQ ID NO 162
<211> LENGTH: 18
```

```
<212> TYPE: DNA
<213> ORGANISM: Artificial Sequence
<220> FEATURE:
<223> OTHER INFORMATION: Antisense Oligonucleotide

<400> SEQUENCE: 162
atgcggagga gaatgttt                                              18

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 163
tcagtgtttt aatctgacg                                             19

<210> SEQ ID NO 164
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 164
gtagatattg ggctgttaat t                                          21

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
gtgagggtaa taatgacttg                                            20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
atgagcatgc ctgtgttggt                                            20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide

<400> SEQUENCE: 167
ggtaagattt gccgagttc                                             19

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
```
tggtgatgct agaggtgatg                                          20

<210> SEQ ID NO 169
<211> LENGTH: 15
<212> TYPE: DNA
<213> ORGANISM: Artificial Sequence
<220> FEATURE:
<223> OTHER INFORMATION: Oligonucleotide

<400> SEQUENCE: 169
gcggtgcctc taata                                               15

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide

<400> SEQUENCE: 170
ggccgttaaa catgtgtcac                                          20

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide

<400> SEQUENCE: 171
tgattatgct acctttgcac                                          20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide

<400> SEQUENCE: 172
ttaaggaaca agtgattatg                                          20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide

<400> SEQUENCE: 173
tggagccatt catacaggtc                                          20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
aaaagtaaga gacagctgaa                                          20

<210> SEQ ID NO 175
<211> LENGTH: 20
<212> TYPE: DNA
<213> ORGANISM: Artificial Sequence

```
<220> FEATURE:
<223> OTHER INFORMATION: Oligonucleotide

<400> SEQUENCE: 175
cacgggcagg tcaatttcac                                              20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
gtcttgctgt gttatgcccg                                              20

<210> SEQ ID NO 177
<211> LENGTH: 19
<212> TYPE: DNA
<213> ORGANISM: Artificial Sequence
<220> FEATURE:
<223> OTHER INFORMATION: Oligonucleotide

<400> SEQUENCE: 177
aattaaagct ccatagggt                                               19

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
gtttgttagg tactgtttgc a                                            21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide

<400> SEQUENCE: 179
aggtttggta gtttaggac                                               19

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide

<400> SEQUENCE: 180
gccccaaccg aaattttaa                                               20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
ctcggaggtt gggttctgct                                              20
```

```
<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
ctggtgaagt cttagcatgt                                                 20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
caattgagta tagtagttcg                                                 20

<210> SEQ ID NO 184
<211> LENGTH: 19
<212> TYPE: DNA
<213> ORGANISM: Artificial Sequence
<220> FEATURE:
<223> OTHER INFORMATION: Oligonucleotide

<400> SEQUENCE: 184
tgttccgttg gtcaagtta                                                  19

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
aataggattg cgctgttatc                                                 20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186
attgttgata tggactctag                                                 20

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide

<400> SEQUENCE: 187
atccaacatc gaggtcgtaa                                                 20

<210> SEQ ID NO 188
<211> LENGTH: 19
<212> TYPE: DNA
<213> ORGANISM: Artificial Sequence
<220> FEATURE:
<223> OTHER INFORMATION: Oligonucleotide
```

```
<400> SEQUENCE: 188
gcggctgcac catcgggat                                              19

<210> SEQ ID NO 189
<211> LENGTH: 19
<212> TYPE: DNA
<213> ORGANISM: Artificial Sequence
<220> FEATURE:
<223> OTHER INFORMATION: Oligonucleotide

<400> SEQUENCE: 189
ttgaacaaac gaacccttta                                             19

<210> SEQ ID NO 190
<211> LENGTH: 20
<212> TYPE: DNA
<213> ORGANISM: Artificial Sequence
<220> FEATURE:
<223> OTHER INFORMATION: Oligonucleotide

<400> SEQUENCE: 190
aactcagatc acgtaggact                                             20

<210> SEQ ID NO 191
<211> LENGTH: 19
<212> TYPE: DNA
<213> ORGANISM: Artificial Sequence
<220> FEATURE:
<223> OTHER INFORMATION: Oligonucleotide

<400> SEQUENCE: 191
aaaccgacct ggattactc                                              19

<210> SEQ ID NO 192
<211> LENGTH: 20
<212> TYPE: DNA
<213> ORGANISM: Artificial Sequence
<220> FEATURE:
<223> OTHER INFORMATION: Oligonucleotide

<400> SEQUENCE: 192
agggaggaat ttgaaggtag                                             20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide

<400> SEQUENCE: 193
ggccttattt ctcttgtcct                                             20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide

<400> SEQUENCE: 194
ggaaggcgct ttgtgaagta                                             20

<210> SEQ ID NO 195
```

<211> LENGTH: 20
<212> TYPE: DNA
<213> ORGANISM: Artificial Sequence
<220> FEATURE:
<223> OTHER INFORMATION: Oligonucleotide

<400> SEQUENCE: 195
aagttgagat gatatcattt 20

<210> SEQ ID NO 196
<211> LENGTH: 17
<212> TYPE: DNA
<213> ORGANISM: Artificial Sequence
<220> FEATURE:
<223> OTHER INFORMATION: Oligonucleotide

<400> SEQUENCE: 196
cctgttcttg ggtgggt 17

<210> SEQ ID NO 197
<211> LENGTH: 18
<212> TYPE: DNA
<213> ORGANISM: Artificial Sequence
<220> FEATURE:
<223> OTHER INFORMATION: Oligonucleotide

<400> SEQUENCE: 197
gtcctaaact accaaacc 18

<210> SEQ ID NO 198
<211> LENGTH: 20
<212> TYPE: DNA
<213> ORGANISM: Artificial Sequence
<220> FEATURE:
<223> OTHER INFORMATION: Oligonucleotide

<400> SEQUENCE: 198
caccctctaa cctagagaag 20

<210> SEQ ID NO 199
<211> LENGTH: 18
<212> TYPE: DNA
<213> ORGANISM: Artificial Sequence
<220> FEATURE:
<223> OTHER INFORMATION: Oligonucleotide

<400> SEQUENCE: 199
aggtggagtg gattgggg 18

<210> SEQ ID NO 200
<211> LENGTH: 2374
<212> TYPE: RNA
<213> ORGANISM: Homo sapiens

<400> SEQUENCE: 200
ucuaauacug gugaugcuag aggugauguu uuugguaaac aggcggggua agauuugccg 60
aguuccuuuu acuuuuuuua accuuuccuu augagcaugc cuguguuggg uugacaguga 120
ggguaauaau gacuuguugg uugauuguag auauugggcu guuaauuguc aguucagugu 180
uuuaaucuga cgcaggcuua ugcggaggag aauguuuuca uguuacuuau acuaacauua 240
guucuucuau agggugauag auugguccaa uuggguguga ggaguucagu uauauguuug 300
ggauuuuuua gguagugggu guugagcuug aacgcuuucu uaauuggugg cugcuuuuag 360
gccuacuaug gguguuaaau uuuuuacucu cucuacaagg uuuuuuccua guguccaaag 420

```
agcuguuccu cuuuggacua acaguuaaau uuacaagggg auuuagaggg uucugugggc    480
aaauuuaaag uugaacuaag auucuaucuu ggacaaccag cuaucaccag gcucgguagg    540
uuugucgccu cuaccauaa aucuucccac uauuuugcua cauagacggg ugugcucuuu    600 uagcuguuc uagguagcuc gucugguuuc ggggucuua gcuuggcuc ccuugcaaa       660 guuauuucua guuaauucau uaugcagaag guauagggu uagccuugc uauauuaugc    720 uugguuauaa uuuucaucu uucccuugcg guacuauauc uauugcgcca gguucaauu     780 ucuaucgccu auacuuuauu uggguaaaug guuggcuaa accagcccc aaacccacuc     840 caccuuacua ccagacaacc uuagccaaac cauuuaccca aauaaaguau aggcgauaga   900
aauugaaacc uggcgcaaua gauauaguac cgcaagggaa agaugaaaaa uuauaaccaa   960
gcauaauaua gcaaggacua accccuauac cuucugcaua augaauuaac uagaauuaac  1020
uuugcaagga gagccaaagc uaagacccc gaaaccagac gagcuaccua agaacagcua   1080
aaagagcaca cccgucuaug uagcaaaaua guggaagau uuauagguag aggcgacaaa   1140
ccuaccgagc cuggugauag cugguugucc aagauagaau cuuaguucaa cuuuaaauuu   1200
gcccacagaa cccucuaaau ccccuuguaa auuuaacugu uaguccaaag aggaacagcu   1260
cuuuggacac uaggaaaaaa ccuuguagag agaguaaaaa auuuaacacc cauaguaggc   1320
cuaaaagcag ccaccaauua agaaaagcguu caagcucaac acccacuacc uaaaaaaucc   1380
caaacauaua acugaacucc ucacacccaa uuggaccaau cuaucacccu auagaagaac   1440
uaauguuagu auaaguaaca ugaaaacauu cuccuccgca uaagccugcg ucagauuaaa   1500
acacugaacu gacaauuaac agcccaauau cuacaaucaa ccaacaaguc auuauuaccc   1560
ucacugucaa cccaacacag gcaugcucau aaggaaaggu uaaaaaagu aaaaggaacu    1620 cggcaaaucu uaccccgccu guuuaccaaa aacaucaccu uagcaucac caguauuaga    1680 ggcaccgccu gcccagugac acauguuuaa cggccgcggu acccuaaccg ugcaaaggua   1740
gcauaaucac uuguuccuua auagggaccc uguaugaaug gcuccacgag gguucagcug   1800
ucucuuacuu uuaaccagug aaauugaccu gcccgugaag aggcgggcau aacacagcaa   1860
gacgagaaga cccuauggag cuuuaauuua uuaaugcaaa caguaccuaa caaacccaca   1920
gguccuaaac uaccaaaccu gcauuaaaaa uuucgguugg ggcgaccucg gagcagaacc   1980
caaccuccga gcaguacaug cuaagacuuc accagcaaa gcgaacuacu auacucaauu   2040
gauccaauaa cuugaccaac ggaacaaguu acccuaggga uaacagcgca auccuauucu   2100
agaguccaua ucaacaauag gguuuacgac cucgauguug gaucaggaca ucccgauggu   2160
gcagccgcua uuaaagguuc guuguucaa cgauuaaagu ccuacgugau cugaguucag   2220
accggaguaa uccaggucgg uuucuaucua ccuucaaauu ccuccuguaa cgaaaggaca   2280
agagaaauaa ggccuacuuc acaaagcgcc uuccccgua aaugauauca ucucaacuua    2340 guauuuuaucc cacacccacc caagaacagg guuu                              2374
```

<210> SEQ ID NO 201
<211> LENGTH: 1679
<212> TYPE: RNA
<213> ORGANISM: Homo sapiens

<400> SEQUENCE: 201

```
gggucuuag cuuggcucu ccuugcaaag uuauuucuag uuaauucauu augcagaagg      60 uauaggggu aguccuugcu auauuaugcu ugguuauaau uuucaucuu ucccuugcgg     120
```

```
ugcuaaaccu agccccaaac ccacuccacc uuacuaccag acaaccuuag ccaaaccauu      180
uacccaaaua aaguauaggc gauagaaauu gaaaccuggc gcaauagaua uaguaccgca      240
agggaaagau gaaaaauuau aaccaagcau aauauagcaa ggacuacccc cuauaccuuc      300
ugcauaauga auuaacuaga aauaacuuug caaggagagc caaagcuaag accccgaaa       360 ccagacgagc uaccuaagaa cagcuaaaag agcacacccg ucuauguagc aaaauagugg      420
gaagauuuau agguagaggc gacaaaccua ccgagccugg ugauagcugg uuguccaaga      480
uagaaucuua guucaacuuu aaauuugccc acagaacccu cuaaucccc uuguaaauuu       540 aacuguuagu ccaaagagga acagcucuuu ggacacuagg aaaaaaccuu guagagagag      600 uaaaaauuu aacacccaua guaggccuaa aagcagccac caauuaagaa agcguucaag       660
cucaacaccc acuaccuaaa aaaucccaaa cauauaacug aacuccucac acccaauugg      720
accaaucuau cacccuauag aagaacuaau guuaguauaa guaacaugaa acauucucc       780 uccgcauaag ccugcgucag auuaaaacac ugaacugaca auuaacagcc caauaucuac      840
aaucaaccaa caagucauua uuccccucac ugucaaccca acacaggcau gcucauaagg      900
aaagguuaaa aaaaguaaaa ggaacucggc aaaucuuacc ccgccuguuu accaaaaaca      960
ucaccucuag caucaccagu auuagaggca ccgccugccc agugacacau guuuaacggc     1020
cgcgguaccc uaaccgugca aaggagcau aaucacuugu ccuuaaaua gggaccugua      1080 ugaauggcuc cacgaggguu cagcugucuc uuacuuuuaa ccagugaaau ugaccugccc     1140
gugaagaggc gggcauaaca cagcaagacg agaagacccu auggagcuuu aauuuauuaa     1200
ugcaaacagu accaacaaa cccacagguc cuaaacuacc aaaccugcau uaaaauuuc       1260 gguuggggcg accucggagc agaacccaac cuccgagcag uacaugcuaa gacuucacca     1320
gucaaagcga acuacuauac ucaauugauc caauaacuug accaacggaa caaguuaccc     1380
uagggauaac agcgcaaucc uauucuagag uccauaucaa caauagggu uacgaccucg     1440 auguuggauc aggacauccc aauggugcag ccgcuauuaa agguucguuu guucaacgau     1500
uaaaguccua cgugaucuga guucagaccg gaguaaucca ggucgguuuc uaucuacuuc     1560
aaauuccucc cuguacgaaa ggacaagaga aauaaggccu acuucacaaa gcgccuuccc     1620
ccguaaauga uaucaucuca acuuaguauu auaccacac ccacccaaga acaggguuu      1679
```

<210> SEQ ID NO 202
<211> LENGTH: 1635
<212> TYPE: RNA
<213> ORGANISM: Homo sapiens

<400> SEQUENCE: 202

```
ggggucuuag cuuuggcucu ccuugcaaag uuauuucuag uuaauucauu augcagaagg       60 uauaggggu aguccuugcu aaaccuagcc ccaaacccac uccaccuuac uaccagacaa      120
ccuuagccaa accauuuacc caaauaaagu auaggcgaua gaaauugaaa ccuggcgcaa      180
uagauauagu accgcaaggg aaagaugaaa aauuauaacc aagcauaaua uagcaaggac      240 uaacccuau accuucugca uaugaauua acuagaaaua acuuugcaag gagagccaaa       300
gcuaagaccc ccgaaaccag acgagcuacc uaagaacagc uaaaagagca cacccgcucua     360 uguagcaaaa uaggggaag auuuauaggu agaggcgaca aaccaccga gccuggugau       420 agcugguugu ccaagauaga aucuaguuc aacuuuaaau uugcccacag aacccucuaa     480
aucccccugu aaauuuaacu guuaguccaa agaggaacag cucuuuggac acuaggaaaa     540
aaccuuguag agaguaaaa aauuuaaca cccauaguag gccuaaaagc agccaccaau       600
```

| | |
|---|---|
| uaagaaagcg uucaagcuca acacccacua ccuaaaaaau cccaaacaua uaacugaacu | 660 |
| ccucacaccc aauuggacca aucuaucacc cuauagaaga acuaauguua guauaaguaa | 720 |
| caugaaaaca uucuccuccg cauaagccug cgucagauua aaacacugaa cugacaauua | 780 |
| acagcccaau aucuacaauc aaccaacaag ucauuauuac ccucacuguc aacccaacac | 840 |
| aggcaugcuc auaaggaaag guuaaaaaaa guaaaggaa cucggcaaau cuuaccccgc | 900 |
| cuguuuacca aaaacaucac cucuagcauc accaguauua gaggcaccgc cugcccagug | 960 |
| acacauguuu aacggccgcg uacccuaac cgugcaaagg uagcauaauc acuguuccu | 1020 |
| uaaauaggga ccuguaugaa uggcuccacg aggguucagc ugucucuuac uuuuaaccag | 1080 |
| ugaaauugac cugcccguga agaggcgggc auaacacagc aagacgagaa gacccuaugg | 1140 |
| agcuuuaauu uauuaaugca aacaguaccu aacaaaccca cagguccuaa acuaccaaac | 1200 |
| cugcauuaaa aauuucgguu ggggcgaccu cggagcagaa cccaaccucc gagcaguaca | 1260 |
| ugcuaagacu ucaccaguca aagcgaacua cuauacucaa uugauccaau aacuugacca | 1320 |
| acggaacaag uuacccuagg gauaacagcg caauccuauu cuagagucca uaucaacaau | 1380 |
| aggguuuacg accucgaugu uggaucagga caucccaaug gugcagccgc uauuaaaggu | 1440 |
| ucguuuguuc aacgauuaaa guccuacgug aucugaguuc agaccggagu aauccagguc | 1500 |
| gguuucuauc uacuucaaau uccucccugu acgaaaggac aagagaaaua aggccuacuu | 1560 |
| cacaaagcgc cuuccccgu aaaugauauc aucucaacuu aguauuauac ccacacccac | 1620 |
| ccaagaacag gguuu | 1635 |

<210> SEQ ID NO 203
<211> LENGTH: 1921
<212> TYPE: RNA
<213> ORGANISM: Homo sapiens

<400> SEQUENCE: 203

| | |
|---|---|
| aaccuccgag caguacaugc uaagacuuca ccagucaaag cgaacuacua cucaauug | 60 |
| auccaauaac uugaccaacg gaacaaguua cccuagggau aacagcgcaa uccuauucua | 120 |
| gauccauau caacaauagg guuuacgacc ucgauguugg aucaggacau cccaauggug | 180 |
| cagccgcuau aaagguucg uuuguucaac gauuaaaguc cuacgugauc ugaguucaga | 240 |
| ccggaguaau ccaggucggu uucuaucuac uucaaauucc ucccguacg aaaggacaag | 300 |
| agaaauaagg ccuacuucac aaagcgccuu ccccguaaa ugauaucauc aacuuagu | 360 |
| auuauacccu gucuggggu ggguguggu auaauacuaa guugagauga uaucauuuac | 420 |
| ggggaaggc gcuugugaa guaggccuua uuucucuugu ccuucguac agggaggaau | 480 |
| uugaaguaga uagaaaccga ccuggauuac uccggcucga acuacgauca cguaggacuu | 540 |
| uaaucguuga acaaacgaac cuuuaauagc ggcugcacca ucggaugguc cugauccaac | 600 |
| aucgaggucu uaaacccuau uguugauaug acucuagaa uaggauugcg cuguuauccc | 660 |
| uagggguaacu uguuccguug gucaaguuau uggaucaauu gaguauagua guucgcuuug | 720 |
| acuggugaag ucuuagcaug uacugcucgg agguuggguu cugcuccgag gucgccccaa | 780 |
| ccgaaauuuu uaaugcaggu uuggaguuu aggaccugug gguuguuag guacuguuug | 840 |
| cauuaauaaa uuaaagcucc uaggggucuu ucgucuugc ugguuaugc ccgccucuuc | 900 |
| acgggcaggu caauucacu gguuaaaagu aagagacagc ugaacccucg uggagccauu | 960 |
| caaucaggvc ccuauuuaag gaacaaguga uuaugcuacc uuugcacggu uagggauaccg | 1020 |

| | |
|---|---|
| cggccguuaa acaugucuca cugggcaggc ggugccucua auacuggga ugcuagaggu | 1080 |
| gauguuuug guaaacaggc ggggguaagau uugccgaguu ccuuuuacuu uuuuaaccu | 1140 |
| uuccuuauga gcaugccugu guugggugga cagugagggu aauaaugacu uguugguuga | 1200 |
| uuguagauau ugggcuguua auugucaguu caguguuuua aucgacgca ggcuuaugcg | 1260 |
| gaggagaaug uuucauguu acuuauacua acauuaguuc uucuauaggg ugauagauug | 1320 |
| guccaauugg gugugaggag uucaguuaua uguuuggau uuuuaggua gggguguug | 1380 |
| agcuugaacg cuuucuuaau ugguggcugc uuuuaggccu acaugggug uuaaauuuuu | 1440 |
| uacucucucu acaagguuuu uuccuagugu ccaaagagcu guccucuuu ggacuaacag | 1500 |
| uuaaauuuac aaggggauuu agagggucu ugggcaaau uuaaguuga acuaagauuc | 1560 |
| uaucuuggac aaccagcuau caccaggcuc gguagguuug ucgccucuac cuauaaaucu | 1620 |
| ucccacuauu uugcuacaua gacgggugug cucuuuuagc uguucuuagg uagcucgucu | 1680 |
| gguucggggg gucuuagccu uggcucuccu ugcaaaguua uuucuaguua auucauuaug | 1740 |
| cagaagguau agggguuagu ccuugcuaua uuaugcuugg uuauaauuuu ucaucuuucc | 1800 |
| cuugcgguac auaucuauu gcgccagguu ucaauuucua ucgccuauac uuuauuggg | 1860 |
| uaaaugguuu ggcuaagguu gucugguagu aagguggagu ggguuggggg cuagguuuag | 1920 |
| c | 1921 |

<210> SEQ ID NO 204
<211> LENGTH: 1744
<212> TYPE: RNA
<213> ORGANISM: Homo sapiens

<400> SEQUENCE: 204

| | |
|---|---|
| uagggauaac agcgcaaucc uauucuagag uccauaucaa caauaggguu uacgaccucg | 60 |
| auguuggauc aggacauccc gauggugcag ccgcuauuaa agguucguuu guucaacgau | 120 |
| uaaaguccua cgugaucuga guucagaccg gaguaaucca ggucguuuc uaucuaccuu | 180 |
| caaauuccuc ccguucuug gguggugug gguauaauac uaaguugaga ugauaucauu | 240 |
| uacgggggaa ggcgcuuugu gaaguaggcc uuauuucucu guccuuucg uacagggagg | 300 |
| aauuugaagu agauagaaac cgaccuggau uacuccgguc ugaacucaga ucacguagga | 360 |
| cuuuaaucgu ugaacaaacg aaccuuuaau agcggcugca ccaucgggau guccugaucc | 420 |
| aacaucgagg ucguaaaccc uauuguugau auggacucua gaauaggau gcgcuguuau | 480 |
| cccuagggua acuguuccg uuggucaagu uauuggauca auugaguaua guaguucgcu | 540 |
| uugacuggug aagcuuagc auguacugcu cggagguugg guucugcucc ggagucgccc | 600 |
| caaccgaaau uuuuaaugca gguugguag uuuaggaccu guggguuugu uagguacugu | 660 |
| uugcauuaau aaauuaaagc uccauagggu cuucucgucu ugcuguguua ugccgccuc | 720 |
| uucacgggca ggucaauuuc acugguuaaa aguaagagac agcugaaccc ucgugggagcc | 780 |
| auucauacag gucccuauuu aaggaacaag ugauuaugcu accuuugcac gguuagggua | 840 |
| ccgcggccgu uaaacaugug ucacugggca ggcggugccu cuaauacugg ugaugcuaga | 900 |
| ggugauguuu uugguaaaca ggcggggua gauuugccga guuccuuuua cuuuuuuaa | 960 |
| ccuuuccuua ugagcaugcc uguguggu ugacagugag gguaauaaug acuguuggu | 1020 |
| ugauuguaga uaugggcug uuaauuguca guucagguguu uuaaucgac gcaggcuuau | 1080 |
| gcggaggaga auguuucau guuacuuaua cuaacauuag uucuucuaua gggugauaga | 1140 |
| uuggguccaau uggggugugag gaguucaguu auauguuugg gauuuuuag guaguggug | 1200 |

```
uugagcuuga acgcuuucuu aauugguggc ugcuuuuagg ccuacuaugg uguuaaauu      1260
uuuuacucuc ucuacaaggu uuuuuccuag uguccaaaga gcuguuccuc uuuggacuaa      1320
caguuaaauu uacaaggggga uuuagagggu ucugugggca aauuuaaagu ugaacuaaga    1380
uucuaucuug gacaaccagc uaucaccagg cucgguaggu uugucgccuc uaccauaaa      1440
ucuucccacu auuuugcuac auagacgggu gugcucuuuu agcuguucuu agguagcucg      1500
ucugguuucg gggucuuag cuuuggcucu ccuugcaaag uuauuucuag uuaauucauu      1560
augcagaagg uauaggggguu aguccuugcu auauuaugcu ugguuauaau uuucaucuu      1620
ucccuugcgg uacauauaucu auugcgccag guuucaauuu cuaucgccua acuuuauuu     1680
ggguaaaugg uuuggcuaag guugucuggu aguaaggugg aguggguuug gggcuagguu    1740
uagc                                                                  1744
```

<210> SEQ ID NO 205
<211> LENGTH: 1854
<212> TYPE: RNA
<213> ORGANISM: Homo sapiens

<400> SEQUENCE: 205

```
gaacucggca aaucuuaccc cgccuguuua ccaaaaacau caccucuagc aucaccagua      60
uuagaggcac cgccugccca gugacacaug uuuaacggcc gcgguacccu aaccgugcaa    120
agguagcaua aucacuuguu ccuuaaauag ggaccuguau gaauggcucc acgaggguuc    180
agcugucucu acuuuuaac cagugaaauu gaccugcccg ugaagaggcg ggcaugacac      240
agcaagacga gaagacccua uggagcuuua auuuauuaau gcaaacagua ccuaacaaac     300
ccuguucuug ggugggugug gguauaaauac uaaguugaga ugauaucauu uacgggggaa    360
ggcgcuuugu gaaguaggcc uuauuucucu uguccuuucg uacagggagg aauuugaagu    420
agauagaaac cgaccuggau uacuccgguc ugaacucaga ucacuaggga cuuuaaucgu    480
ugaacaaacg aaccuuuaau agcggcugca ccaucgggau guccugaucc aacaucgagg    540
ucguaaaccc uauuguugau aauggacucua gaauaggauu gcgcuguaua cccuagggua   600
acuuguuccg uugguucaagu uauuggauca auugaguaua uaguucgcu uugacugggug   660
aagucuuagc auguacugcu cggaagguugg uucugcucc gaggucgccc caaccgaaau    720
uuuuaaugca gguuugguag uuuaggaccu guggguuugu uagguacugu uugcauuaau    780
aaauuaaagc uccauagggu cuucucgucu ugcuguguua ugccggccuc uucacgggca    840
ggucaauuuc acugguuuaaa aguaagagac agcugaaccc ucguggagcc auucauacag   900
gucccuauuu aaggaacaag ugauuaugcu accuuugcac gguuagggua ccgcggccgu   960
uaaacaugu ucacugggca ggcggugccu cuaauacugg ugaugcuaga ggugauguu     1020
uugguaaaca ggcggggguaa gauuugccga guccuuuuua cuuuuuuuaa ccuuuccuua   1080
ugagcaugcc uguguggguu ugacagugag gguaauaaug acuuguuggu ugauuguaga    1140
uauuggggcug uuaauugca guucagugu uuaaucugac gcaggcuuau gcggaggaga    1200
auguuucau guuacuuaua cuaacauuag uucuucuaua ggguguaaga uuggccaau    1260
ugggugugag gaguucaguu auauguuugg gauuuuuag guaguggggug uugagcuuga    1320
acgcuuucuu aauugguggc ugcuuuuagg ccuacuaugg uguuaaauu uuuuacucuc    1380
ucuacaaggu uuuuccuag uguccaaaga gcguuccuc uuuggacuaa caguuaaauu     1440
uacaaggggga uuuagagggu ucugugggca aauuuaaagu ugaacuaaga uucuaucuug   1500
```

-continued

| | | | | | | |
|---|---|---|---|---|---|---|
| gacaaccagc | uaucaccagg | cucgguaggu | uugucgccuc | uaccuauaaa | ucuucccacu | 1560 |
| auuuugcuac | auagacgggu | gugcucuuuu | agcuguucuu | agguagcucg | ucugguuucg | 1620 |
| ggggucuuag | cuuuggcucu | ccuugcaaag | uuauuucuag | uuaauucauu | augcagaagg | 1680 |
| uauaggggu | aguccuugcu | auauuaugcu | ugguuauaau | uuuucaucuu | ucccuugcgg | 1740 |
| uacuauaucu | auugcgccag | guuucaauuu | cuaucgccua | uacuuuauuu | ggguaaaugg | 1800 |
| uuuggcuaag | guugucuggu | aguaaggugg | aguggguuug | gggcuagguu | uagc | 1854 |

What is claimed is:

1. A method for treating or suppressing metastatic cancer in an individual comprising administering to the individual an effective amount of one or more oligonucleotide complementary to a human non-coding chimeric mitochondrial RNA molecule comprising:
   a. an antisense 16S mitochondrial ribosomal RNA covalently linked at its 5' end to the 3' end of a polynucleotide with an inverted repeat sequence or
   b. a sense 16S mitochondrial ribosomal RNA covalently linked at its 5' end to the 3' end of a polynucleotide with an inverted repeat sequence,
   wherein the one or more oligonucleotide is able to hybridize with the chimeric mitochondrial RNA molecules to form a stable duplex,
   wherein the metastatic cancer is selected from the group consisting of bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, and thyroid cancer, and
   wherein the individual has been previously treated for cancer with a therapy.

2. The method of claim 1, wherein the individual has been previously treated for cancer with a therapy comprising chemotherapy, radiation therapy, surgery, or combinations thereof.

3. The method of claim 2, wherein the individual has been previously treated for cancer with a therapy and said therapy is surgery.

4. The method of claim 1, wherein the one or more oligonucleotide is complementary to the antisense 16S mitochondrial ribosomal RNA molecule encoded by a nucleotide sequence selected from the group consisting of SEQ ID NO: 203, SEQ ID NO: 204, SEQ ID NO: 205.

5. The method of claim 1, wherein the one or more oligonucleotide comprises a nucleotide sequence selected from the group consisting of SEQ ID NOs: 7-198.

6. The method of claim 1, wherein the one or more oligonucleotide comprises a nucleotide sequence selected from the group consisting of SEQ ID NOs: 36, 54, 61, 65, 70, 74, 76, 79, 81, 88, 197, and 198.

7. The method of claim 6, wherein the metastatic cancer is selected from the group consisting of bladder cancer, cervical cancer, colon cancer, ovarian cancer, melanoma, and renal cancer.

8. The method of claim 7, wherein the one or more oligonucleotide comprises a nucleotide sequence of SEQ ID NO:36.

9. The method of claim 7, wherein the one or more oligonucleotide comprises a nucleotide sequence of SEQ ID NO: 54.

10. The method of claim 7, wherein the one or more oligonucleotide comprises a nucleotide sequence of SEQ ID NO: 61.

11. The method of claim 7, wherein the one or more oligonucleotide comprises a nucleotide sequence of SEQ ID NO: 65.

12. The method of claim 7, wherein the one or more oligonucleotide comprises a nucleotide sequence of SEQ ID NO: 70.

13. The method of claim 7, wherein the one or more oligonucleotide comprises a nucleotide sequence of SEQ ID NO: 74.

14. The method of claim 7, wherein the one or more oligonucleotide comprises a nucleotide sequence of SEQ ID NO: 76.

15. The method of claim 7, wherein the one or more oligonucleotide comprises a nucleotide sequence of SEQ ID NO: 79.

16. The method of claim 7, wherein the one or more oligonucleotide comprises a nucleotide sequence of SEQ ID NO: 81.

17. The method of claim 7, wherein the one or more oligonucleotide comprises a nucleotide sequence of SEQ ID NO: 88.

18. The method of claim 7, wherein the one or more oligonucleotide comprises a nucleotide sequence of SEQ ID NO: 197.

19. The method of claim 7, wherein the one or more oligonucleotide comprises a nucleotide sequence of SEQ ID NO: 198.

* * * * *